US012633379B2

(12) United States Patent
Ideker et al.

(10) Patent No.: US 12,633,379 B2
(45) Date of Patent: May 19, 2026

(54) VISIBLE NEURAL NETWORK FRAMEWORK

(71) Applicant: THE REGENTS OF THE UNIVERSITY OF CALIFORNIA, Oakland, CA (US)

(72) Inventors: Trey Ideker, San Diego, CA (US); Jisoo Park, San Diego, CA (US); Brent Kuenzi, San Diego, CA (US); Jianzhu Ma, West Lafayette, IN (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 553 days.

(21) Appl. No.: 18/247,711

(22) PCT Filed: Oct. 25, 2021

(86) PCT No.: PCT/US2021/056515

§ 371 (c)(1),
(2) Date: Apr. 3, 2023

(87) PCT Pub. No.: WO2022/087540

PCT Pub. Date: Apr. 28, 2022

(65) Prior Publication Data

US 2025/0273300 A1      Aug. 28, 2025

Related U.S. Application Data

(60) Provisional application No. 63/104,957, filed on Oct. 23, 2020.

(51) Int. Cl.
G16B 40/20      (2019.01)
G06N 3/045      (2023.01)
(Continued)

(52) U.S. Cl.
CPC ............. G16B 40/20 (2019.02); G06N 3/045 (2023.01); G16B 20/20 (2019.02); G16H 20/10 (2018.01); G16H 50/20 (2018.01)

(58) Field of Classification Search
CPC ........ G16B 40/20; G16B 20/20; G16B 15/30; G06N 3/045; G16H 20/10; G16H 50/20; G16H 10/20; G16H 50/70
See application file for complete search history.

(56) References Cited

U.S. PATENT DOCUMENTS

| 6,526,168 B1 * | 2/2003 | Ornes | G06F 18/40 |
| | | | 706/31 |
| 2003/0190603 A1 * | 10/2003 | Larder | G16B 20/20 |
| | | | 435/5 |

(Continued)

OTHER PUBLICATIONS

International Search Report and the Written Opinion for International Application No. PCT/US2021/056515, mailed Jan. 28, 2022, 14 pages.
Suganuma, et al., "A genetic programming approach to designing convolutional neural network architectures", Proceedings of the genetic and evolutionary computation converence, 2017, Aug. 11, 2017; Retrieved on Dec. 27, 2021 from https://arxiv.org/pdf/1704.00764.pdf.

(Continued)

*Primary Examiner* — Pei Yong Weng
(74) *Attorney, Agent, or Firm* — Eversheds-Sutherland (US) LLP

(57) ABSTRACT

Most drugs entering clinical trials fail, often related to an incomplete understanding of the mechanisms governing drug response. Machine learning techniques hold immense promise for better drug response predictions, but most have not reached clinical practice due to their lack of interpretability and their focus on monotherapies. Systems and methods described herein relate to DrugCell, an interpretable deep learning model of human cancer cells trained on the responses of 1,235 tumor cell lines to 684 drugs. Tumor genotypes induce states on cellular subsystems which are integrated with drug structure to predict response to therapy and, simultaneously, learn biological mechanisms underlying the drug response. DrugCell predictions are accurate in cell lines and also stratify clinical outcomes. Analysis of DrugCell mechanisms leads directly to design of synergistic (Continued)

drug combinations, which can be validate systematically. DrugCell provides a blueprint for constructing interpretable models for predictive medicine.

40 Claims, 46 Drawing Sheets

(51) Int. Cl.
G16B 20/20 (2019.01)
G16H 20/10 (2018.01)
G16H 50/20 (2018.01)

(56) References Cited

U.S. PATENT DOCUMENTS

| | | | | |
|---|---|---|---|---|
| 2005/0277149 | A1* | 12/2005 | Friend .................. | G01N 33/574 |
| | | | | 435/455 |
| 2008/0306980 | A1* | 12/2008 | Brunner ................. | G16B 40/20 |
| | | | | 707/999.102 |
| 2010/0205214 | A1* | 8/2010 | Fliri ....................... | G16C 20/62 |
| | | | | 707/E17.014 |
| 2019/0304566 | A1* | 10/2019 | Narain ...................... | A61P 9/04 |

* cited by examiner

Select Accurately
Predicted Compounds

Identify Subsystems
Mediating Drug
Response

Dual gene KOs to Validate Top Subsystem
Importance Using CRISPR/Cas9

25 Compounds in
Deep Synergy Database
$D_1$

Select
Subsystems

RLIPP Analysis

Top 5

Bottom 5

$D_2$    Synergistic
Partner Drugs

Non-Synergistic
Partner Drugs    $D'_2$

Assess Synergy
$(D_1, D_2)$, $(D_1, D'_2)$

1500

1

VISIBLE NEURAL NETWORK FRAMEWORK

CROSS REFERENCE TO RELATED APPLICATIONS

This application is a U.S. National Phase Application of PCT Application No. PCT/US2021/056515, filed on Oct. 25, 2021, which claims priority benefit of U.S. Provisional Application No. 63/104,957, filed Oct. 23, 2020, the entire contents of which are incorporated herein by reference.

GOVERNMENT SPONSORSHIP

This invention was made with government support under CA212456, CA209891, GM103504 and ES014811 awarded by the National Institutes of Health. The government has certain rights in the invention.

TECHNICAL FIELD

The present invention relates to a visible neural network framework.

BACKGROUND

DrugCell is a visible deep learning framework that is interpretable, unlike other conventional black-box models. A model implemented using the framework predicts the response of a genotypically defined cancer to any therapeutic agent. DrugCell model's interpretation provides the biological rationale for its prediction which can be used to design effective combination therapies.

DrugCell is unique in that it is interpretable whereas most deep learning models are black-box models that have no discernable link between input and output. DrugCell has the advantage over these black-box models, in that it couples the inner workings of the deep learning model to the hierarchical structure of human cell biology, allowing for response predictions for any drug in any cancer and intelligent design of effective combination therapies. DrugCell also offers the advantage in that it is transferable to human cancer patients and has demonstrated preliminary efficacy in guiding clinical treatment decisions. While other models have been developed to predict drug response, none do so by simulating cancer cells nor can they suggest effective combination therapies. These other existing models include DeepProfile, models by Cortés-Ciriano et al., and Iorio et al.

Each year dozens of new therapies enter clinical trials for the potential treatment of various types of cancer, but fewer than 4% will ultimately gain approval by the US Food and Drug Administration (Wong et al., 2019). Although many factors contribute to this challenge, a major failure is in understanding how or why a particular cancer responds to therapy. The problem becomes particularly acute for cancers that are not associated with strong targetable genetic drivers (e.g. BCR-ABL fusion, EGFR mutation or EMIL4-ALK translocation), since cancers without these known drivers lack clear biomarkers with which to stratify drug response. A better basic understanding of the molecular pathways governing drug sensitivity would help greatly in determining which patients should be treated and with which drugs.

There has recently been a great deal of interest in applying advances in artificial intelligence, including machine learning and deep learning, to classic problems in biomedicine (Topol, 2019). While popular applications include disease diagnosis from biomedical images and interpretation of electronic medical records (Esteva et al., 2019; Rajkomar et al., 2019; Wainberg et al., 2018), machine learning models are also of high interest in predicting drug responses (Barretina et al., 2012; Costello et al., 2014; Garnett et al., 2012; Iorio et al., 2016; Zeng et al., 2019). In a typical application, the model uses the 'omics profile of a cell line or tissue sample as input to predict the 50% inhibitory concentration (IC50) of a drug. For example, Iorio et al. (2016) built elastic net models to predict drug IC50 of cancer cell lines given their profiles of gene mutations and expression levels; a range of predictive accuracy is observed, depending on the compound. Using the same data set, Cortes-Ciriano et al., (2016) show that predictive performance could in some cases be improved using a random forest model linked to a measure of statistical confidence in each prediction. Deep neural networks (Baptista et al., 2020; Chiu et al., 2019; Menden et al., 2013; Sakellaropoulos et al., 2019) and variational autoencoders (Rampášek et al., 2019) have also been applied to drug response prediction, with significant performance gains noted depending on the drug and disease context.

Owing to the significant molecular heterogeneity observed across tumors, there are often many different molecular features and feature combinations that can lead a model to predict a particular drug response. What these features are, and whether they are distinct or functionally interrelated, can be very difficult to interpret however. The reason is that most machine learning models are "black boxes", optimized for prediction accuracy without knowledge of or attention to the biological mechanisms underlying predicted outcomes (Ching et al., 2018). To address these difficulties, model interpretation is now a rapidly growing subfield within machine learning, with a growing arsenal of approaches for achieving models with not only high predictive accuracy, but also high descriptive accuracy (Murdoch et al., 2019). One major strategy has been to use prior knowledge or data to add structure to the model, which can then be interpreted. Applied to genomics, such a strategy has been used to recast the thousands of measured molecular features of a tumor as states on a much smaller number of functional modules (Cortes-Ciriano et al., 2016; Yang et al., 2019). For example, a recent study mapped raw molecular measurements to a set of pre-defined metabolic pathways drawn from prior knowledge bases; states of these pathways predict antibiotic resistance in *Escherichia coli*, with particular pathway features emerging as candidate mechanisms of resistance (Yang et al., 2019). Organization of molecular features into predictive modules can also be accomplished using prior data as opposed to literature-curated knowledge. Such an approach was recently exemplified by DeepProfile, which analyzed a large collection of leukemia expression profiles to extract a low-dimensional representation of these data as a set of functional gene modules; these modules are then used as interpretable features for drug response prediction (Dincer et al., 2018). Apart from model-based approaches, a second major strategy to increase model interpretability has been to perform post-hoc analysis of model features or feature weights to interpret the underlying drug response mechanisms (Chiu et al., 2019; Iorio et al., 2016; Murdoch et al., 2019). For example, the weights assigned to each input gene by a black box neural network model are subjected to gene set enrichment analysis (Subramanian et al., 2005) to identify pathways regulating the predicted drug response (Sakellaropoulos et al., 2019). These pathways, however, were not used during modeling or validated experimentally.

To more explicitly link the structure of a machine learning model to cellular functions, a visible neural network (VNN) was developed to simulate a simple eukaryotic cell, *Saccharomyces cerevisiae* (Ma et al., 2018; Yu et al., 2018). This model, called DCell, was made mechanistically interpretable, or "visible", by directly mapping the neurons (e.g., artificial neurons or nodes) of a deep neural network into a large hierarchy of known and putative molecular components and pathways. DCell is able to accurately predict the impact of genetic mutations on cellular growth response and, simultaneously, identify the most relevant molecular pathways driving those predictions. Building from this paradigm, a visible neural network that simulates the response of human cancer cells to therapeutic chemical compounds is described herein. DrugCell couples the inner workings of the model to the hierarchical structure of human cell biology, allowing for response predictions for any drug in any cancer and intelligent design of effective combination therapies.

SUMMARY OF THE INVENTION

The disclosure provides a system, termed DrugCell, as a neural network with two branches. The first branch is a visible neural network modeling the hierarchical organization of molecular subsystems in a human cell, drawn from the biological processes documented in the Gene Ontology database. Each of these subsystems, from those involving small protein complexes to larger signaling pathways to overarching cellular functions, was assigned a bank of artificial neurons to represent the state of that subsystem. Connectivity of neurons was set to mirror the biological hierarchy, so that neurons accept inputs only from those of child subsystems and send outputs only to those of parent systems, with connection weights determined during training. The input layer of the hierarchy mapped to the mutation status of genes. The second branch of DrugCell was artificial neural network (ANN) embedding the Morgan fingerprint of a drug, a canonical vector representation of the chemical structure. Outputs from the two branches of the model, the VNN embedding cell genotype and the ANN embedding drug structure, were combined in a single layer of neurons, which were then integrated to generate the response of a given genotype to a particular treatment.

The invention provides DrugCell being used as part of a Molecular Tumor Board. Patients' cancer mutations are input into DrugCell, and the clinicians will receive a rank list of potential therapies suggested to be effective in each patient. Additionally, a report will be generated that will provide the reasons for selecting these therapies so that effective combination therapy can be agreed on by the Molecular Tumor Board based on the recommendations by DrugCell.

BRIEF DESCRIPTION OF THE DRAWINGS

FIG. 1A shows that DrugCell uses a modular neural network design that combines conventional artificial neural networks (ANN) with a visible neural network (VNN) to make drug response predictions. FIG. 1B shows binary encodings of individual genotypes are processed through a VNN with architecture guided by a hierarchy of cell subsystems, with multiple neurons assigned per subsystem.

FIG. 1C shows compound chemical structures are processed through an ANN using the Morgan fingerprint as input features.

FIG. 2A shows predicted versus actual drug responses across all (cell line, drug) pairs studied. Box plots show the 25th, 50th, and 75th percentiles of values in each bin; whiskers show maximum and minimum values. FIG. 2B shows scatterplots of the predictive performance (Spearman rho between actual and predicted drug response across 684 drugs) of DrugCell versus three alternative models: FIG. 2B shows an elastic net. FIG. 2C shows a matched black-box neural network. FIG. 2D shows a tissue-only black-box neural network. Points represent individual drugs; points above the diagonal represent drugs better predicted by DrugCell. FIG. 2E shows a waterfall plot of predictive performance for each drug in the dataset (y axis), ranked from highest to lowest (x axis). "High confidence" drugs are highlighted in red (rho>0.5). The inset shows the performance for the top 10 best predicted drugs.

FIGS. 3A-3D show genotype embeddings of each cell line, showing the first two principal components (PC). Points are cell lines, with colors indicating specific drug responses or genetic markers according to the panel. FIGS. 3A and 3C show that green denotes cell lines harboring mutations in BRAF or in EGFR, BRAF, or LKB1, respectively. Gray denotes cell lines without mutations in these genes. FIGS. 3B and 3D show blue-to-red gradient represents the response to selumetinib or JQ-1, respectively. Gray denotes cell lines not tested against that drug. FIG. 3E shows drug structure embedding. Points are drugs, with colors indicating drug target classes. FIG. 3G shows a waterfall plot of top 5% of subsystems (x axis) important for paclitaxel response by RLIPP score (y axis). Subsystems capturing metabolic pathways are highlighted in red. FIG. 3H shows a visualization of select subsystems highlighted in FIG. 3G, comprising a sub-hierarchy of the full DrugCell model. Red is used to trace the branches of the hierarchy related specifically to regulation of glycolysis. FIG. 3I shows a response to CAMP subsystem embedding. Points are cell lines, blue-to-red gradient represents response to paclitaxel. FIG. 3J shows a boxplot of the relative cell viability of treatment with DMSO, paclitaxel, 2-deoxyglucose (2-DG), or the combination at the indicated concentrations in A427 cells. Data are representative of drug treatments performed in biological and technical triplicates. The boxes represent the interquartile range (IQR) bisected by the median, whiskers represent the maximum and minimum range of the data that do not exceed 1.5 times the IQR. ***$p<0.0001$ from a t test.

FIGS. 4A-4H show a systematic validation of identified mechanisms of sensitivity using CRISPR/Cas9. FIG. 4A shows a workflow of systematic analysis using CRISPR/Cas9. FIG. 4B shows a heatmap of the area under the fitness curves for 176 cancer genes in combination with MAP2K1, PARP1, and TP53. FIGS. 4C-4E show bar plots of the KLIPP scores of the top five subsystems for (FIG. 4C) trametinib, (FIG. 4D)) olaparib, and (FIG. 4E) nutlin-3. FIGS. 4F-4H show boxplots of the area under the fitness curve following CRISPR/Cas9-mediated knockout of (FIG. 4F) MAP2K1, (FIG. 4G) PARP1, and (FIG. 4H) TP53 in combination with highly weighted genes within the top five subsystems identified by DrugCell for each parent drug compared with random. Select genes are labeled. The boxes represent the IQR bisected by the median, and whiskers represent the maximum and minimum range of the data that do not exceed 1.5 times the IQR. *p<0.05 from a t test, NS denotes not significant.

FIG. 5A shows a parallel pathway theory of drug synergy, in which a pathway 2 is targeted by the mechanism of action (MoA) of drug A, and synergy is achieved by simultaneously targeting parallel pathway 1 with drug B. FIG. 5B shows logic learned by DrugCell for drug A, in which pathway 1 arises as a predicted mechanism of the VNN. FIG. 5C shows workflow demonstrating systematic design and assessment of pairwise combinations of drugs. FIG. 5D shows boxplots of DeepSynergy synergy scores for predicted drug combinations, predicted non-synergistic combinations, and random combinations. The boxes represent the IQR bisected by the median, and whiskers represent the maximum and minimum range of the data that do not exceed 1.5 times the IQR. *p<0.0001. FIG. 5E shows representative subsystems used by DrugCell to simulate etoposide sensitivity (red nodes), along with a negative control branch (white node). RLIPP scores are displayed inside each node. Subsystem names are abbreviated. FIG. 5F shows bee swarm plot of the Loewe synergy scores observed upon combination of etoposide with MK2206, PD325901, or bortezomib. Drug combinations were chosen based on subsystems identified in (FIG. 5E). Red dotted line indicates the mean of all Loewe synergy scores in the dataset. *p<0.0001. * without bars represent t test against the synergy score distribution of the full dataset (FIG. 13), or bortezomib negative control, as indicated. Red points are cell lines for which synergy is observed. Blue points are cell lines for which antagonism is observed. FIG. 5G shows boxplots of the relative cell growth of A549 cells following CRISPR/Cas9-mediated knockout of MAP2K1, PIK3CA, or APC (negative control) in combination with TOP2 or a non-targeting control (NT). Data are reflective of two independent transductions. *p<0.0001, *p<0.1, **p<0.01. (FIG. 5H) Boolean logic circuit approximating how the mutational status of genes in the PI3K and ERK subsystems is translated to an etoposide response by DrugCell. FIG. 5I shows a truth table showing translation of PI3K and ERK states to a binary drug response output. The percentage of observed sensitive versus resistant cells for each state is shown. Dotted line indicates baseline percentage of etoposide-resistant samples among all cell lines. FIG. 5J show odds ratios of etoposide response prediction for DrugCell, the ERK and PI3K logic functions from (FIG. 5H), and individual genes from (FIG. 5H). Percentages of cell lines with an alteration to that biomarker are also shown. Odds ratios are against a background of cell lines that are wild type with respect to this circuit.

FIG. 6A shows a flowchart of analysis procedure. FIG. 6B shows an ROC curve of DrugCell performance in distinguishing effective from ineffective drug combinations. FIG. 6 C shows an error matrix for point indicated in (FIG. 6B) demonstrating best performance of DrugCell against the PDX dataset. FIG. 6D shows survival curves for drug combinations predicted to be effective by DrugCell (true positives) showing a significant improvement in progression-free survival. FIG. 6E shows survival curves for drug combinations predicted to be ineffective by DrugCell (true negatives) showing a lack of improvement in progression-free survival. p values indicate significance by log rank test. ***p<0.0001, NS indicates not significant.

FIGS. 7A-7C show survival curves for DrugCell (+) and Drug-Cell (−) patients treated with CDK4/6 or mTOR inhibitors in any line of therapy. The p value indicates significance by log rank test. (FIGS. 7B, 7C) Important subsystems used by DrugCell to simulate (FIG. 7B) mTOR or (Figure C) CDK4/6 inhibitor sensitivity. Dotted line abbreviates parent subsystems at subsequent layers of the hierarchy. RLIPP scores are displayed inside each node. FIG. 7D shows a scatterplot of the absolute (x axis) and percentage (y axis) difference in mutation frequencies of genes between DrugCell (+) and DrugCell (−) patients. Red points represent genes mutated more frequently in DrugCell (+) patients. Blue points represent genes mutated more frequently in DrugCell (−) patients. Point size is proportional to overall mutation frequency in the patient population. FIG. 7E shows survival curves for AKT1-mutant and wild-type patients treated with CDK4/6 or mTOR inhibitors in any line of therapy. The p value indicates significance by log rank test.

FIG. 8A shows a circle packing diagram of a subsystem hierarchy used to structure the DrugCell VNN. Circles represent subsystems, and circles contained in larger circles indicate child-parent (or child-ancestor) subsystem relationship. The largest circle represents the entire collection of subsystems at the root of the hierarchy. Select large subsystems are labeled. FIG. 8B shows numbers of neurons present in each layer of the subsystem hierarchy. FIG. 8C shows distribution of drug response values across all drugs and cancer cell lines. AUC=normalized Area Under dose response Curve (0=complete cell killing, 1=no effect). FIG. 8D) shows number of cell lines of each tissue type represented in the training data. FIG. 8E shows histogram of the number of mutations per cell line used for model training. FIG. 8F shows histogram of the number of compounds with each distinct number of activated bits, a measure of structural complexity. FIG. 8G shows histogram of the number of molecular fragments contained within each bit of the molecular bit vector.

FIG. 9A shows a heatmap showing the Pearson correlation of the predicted drug responses across cell lines for each pair of 203 high-confidence drugs. Both rows and columns are hierarchically clustered based on the observed (rather than predicted) drug responses; note the clustering pattern of these training data is maintained in the DrugCell predictions. The high confidence drug set is defined in FIG. 2C. Outlined cluster solely contains MAPK pathway inhibitors. FIG. 9B shows scatterplot comparing the predictive performance of individual drugs to the number of drug-cell pairs available for training. FIG. 9C shows scatterplot comparing the predictive performance of individual drugs to the structural complexity of the compound (number of activated bits). FIG. 9D shows scatterplot comparing the predictive performance of individual drugs to the standard deviation of the observed compound responses across all cell lines. FIG. 9E shows histogram of the predictive performance of DrugCell across individual cell lines. FIG. 9F shows histogram of the predictive performance of DrugCell across individual tissue types.

FIG. 10A shows for each subsystem in DrugCell, computed Spearman correlations between the predicted subsystem activity and the corresponding activity measured by RPPA (red histogram, STAR Methods). Random (blue) shows the equivalent correlations for random sets of proteins. FIG. 10B shows example subsystem embedding for Regulation of MAPK cascade. The x and y axes plot the two principal components (PCs) from this embedding that are most significantly associated with RPPA activity. Points are cell lines. Color corresponds to the measured RPPA activity, calculated as the sum of protein abundance and phosphorylation values of proteins in the subsystem. RPPA protein values are normalized across all proteins on the array, with the median value set to 0). Also shown is the Spearman rho of the subsystem activity as predicted by the DrugCell PCs vs. the actual value measured by RPPA. FIG. 10C shows scatterplot of the activating phosphorylation status of ERK1/2 compared to the subsystem activity from FIG. 10D. Spearman rho is displayed. FIGS. 10D-10F show subsystem embeddings of Proteolysis (FIG. 10D), Regulation of PI3K signaling (FIG. 10E), and Cell cycle arrest subsystems (FIG. 10F). Display items as in panel B. Some subsystem names are abbreviated.

FIG. 11A shows scatterplot of the structural similarity of each compound in the dataset (Tanimoto similarity) compared to their Euclidean distance in the chemical structure embedding. FIGS. 11B-11D show drug structure embedding. Points are individual drugs, with blue-yellow gradient denoting the membrane permeability (Log P) (FIG. 11B), compound solubility (Ali Log S) (FIG. 11C), or the number of Lipinski violations (FIG. 11D).

FIGS. 12A-12D show analysis of mechanisms mediating paclitaxel sensitivity, related to FIG. 3. FIG. 12A shows beeswarm plot of the Loewe synergy score observed upon combination of bortezomib with paclitaxel. Red dotted line indicates the mean of all Loewe synergy scores in the dataset. Red points are cell lines for which positive synergy is observed. Blue points are cell lines for which antagonism (negative synergy) is observed. FIG. 12B shows heatmap of the mRNA expression levels of the top 125 genes (rows) differentially expressed between 25 paclitaxel sensitive and 25 resistant cell lines (columns). FIG. 12C shows gene Ontology enrichment of these 125 differentially expressed genes. Top 15 most significant GO terms are displayed (hypergeometric test). Terms corresponding to subsystems that were also within the top 100 of highest importance (RLIPP score) to DrugCell are highlighted in red. FIG. 12D shows beeswarm plot of the Loewe synergy score observed upon combination of veliparib, niraparib or temozolomide with paclitaxel. Drug combinations were chosen based on the DNA replication and Response to ionizing radiation terms identified in FIG. 12C. Red dotted line indicates the mean of all Loewe synergy scores in the dataset (FIG. 13). Red points are cell lines for which positive synergy is observed. Blue points are cell lines for which antagonism (negative synergy) is observed.

FIG. 14A shows scatterplot of drug response values from this study versus those from a previously published analysis of CTRPv2 (Seashore-Ludlow et al., 2015). FIG. 14B shows DrugCell predictive performance as a function of the number of neurons per subsystem. Predictive performance is assessed for each drug individually as the Spearman correlation between predicted and actual drug responses (y axis). Performance is summarized (violin plots)

for 684 drugs across the four tested models (x axis). Inner box plots as in panel A. Based on these results, DrugCell was constructed with 6 neurons per subsystem (purple greyscales).

Figure 15:
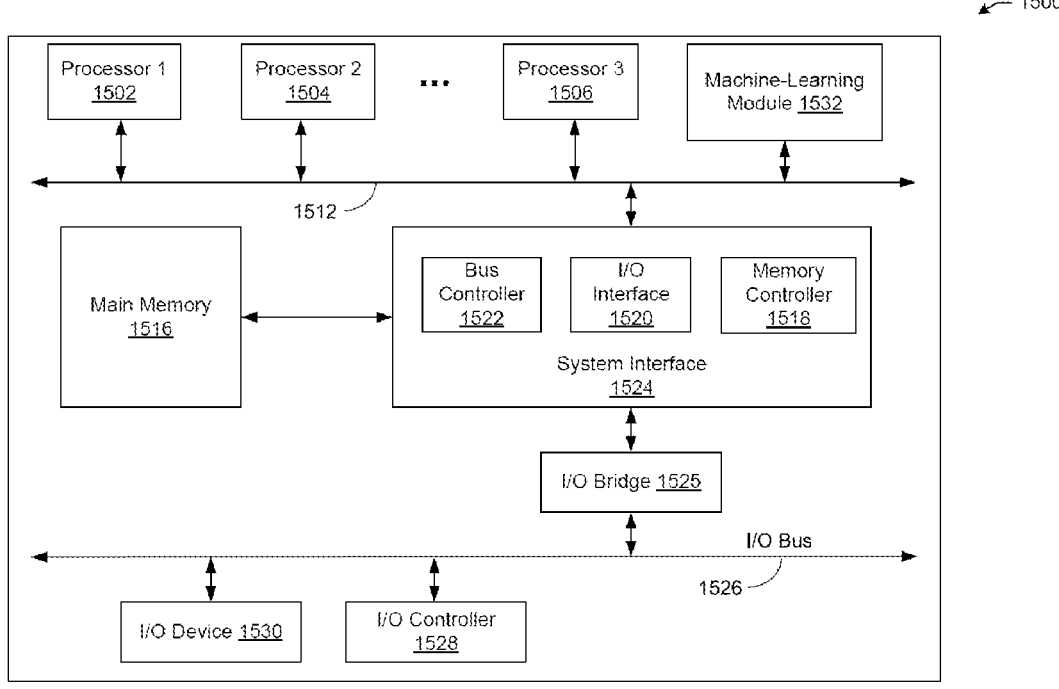

FIG. 15 is a block diagram illustrating an example of a computing device or computer system 1500, which may be used to train DrugCell, predict or infer using DrugCell, and more.

DETAILED DESCRIPTION

All publications, patents, and patent applications mentioned in this specification are herein incorporated by reference to the same extent as if each individual publication, patent, or patent application was specifically and individually indicated to be incorporated by reference.

Unless defined otherwise, all technical and scientific terms and any acronyms used herein have the same meanings as commonly understood by one of ordinary skill in the art in the field of the invention. Although any methods and materials similar or equivalent to those described herein can be used in the practice of the present invention, the exemplary methods, devices, and materials are described herein.

In embodiments, a first aspect of the invention provides a system for predicting one or more effects of administration of a compound to a living tissue of a subject. In embodiments, the system may comprise one or more processors and memory storing execution instructions that, as a result of execution by the one or more processors, cause the one or more processors to implement various functionality relating to predicting one or more effects of the administration of a compound to a living tissue of a subject.

In embodiments, the functionality may comprise steps to: determine genotype information of the living tissue, provide the genotype information to a first portion of one or more neural networks, wherein the first portion comprises a visible neural network (VNN), wherein the VNN further comprises: a plurality of neurons are organized into a plurality of subsystems that corresponds to known or putative molecular subsystems; and a plurality of connections, wherein a connection between a first subsystem and a second subsystem of the VNN corresponds to a known or putative molecular pathway, wherein a weight of the connection is determined during training of the one or more neural networks and corresponds to how predictive the connection is to a drug response; receive, from the VNN, a first embedding vector representing cell genotype information; provide a molecular fingerprint of the compound to a second portion of the one or more neural networks, wherein the second portion comprises an artificial neural network (ANN) that determines canonical vector representations of compounds; receive, from the ANN, a second embedding vector representing compound structure information of the compound; and provide the first embedding vector and the second embedding vector to a third portion of the one or more neural networks, wherein the third portion comprises one or more layers of neurons trained to predict a response of the compound based on the genotype information; and receive, from the third portion, a prediction of whether the subject will respond to the administration of the compound.

In embodiments, the Relative Local Improvement in Predictive Power metric (RLIPP) scoring is used to identify subsystems of the plurality of subsystems that are most predictive of a response to the compound.

In embodiments, the third portion of the one or more neural networks comprises a single layer of neurons that are integrated to generate a predicted effect of a given genotype to the compound.

In embodiments, the mutation statuses of a plurality of genes.

In embodiments, the
  predication predicts the effects of the compound on a genotypically defined cancer tissue.

In embodiments, the system implements further functionality to present a graphical interface comprising a visualization of the plurality of subsystems mediating the response.

In embodiments, the visualization provides an indication one or more metabolic pathways.

In embodiments, the compound comprise a chemotherapeutic, a targeted therapy, or a combination thereof.

In embodiments, the VNN is organized into a plurality of layers; a first layer of the plurality of layers that receives the genotype information represents genes; and one or more subsequent layers of the plurality of layers represent molecular subsystems of greater complexity and/or scale.

In embodiments, wherein the VNN comprises six layers.

In embodiments, wherein the ANN comprises a fully connected network.

In embodiments, wherein the third portion of the one or more neural networks comprises a single layer of neurons that integrates the first embedding and second embedding to generate the prediction of whether the subject will respond to the administration of the compound.

In embodiments, a second aspect of the invention provides a method for predicting one or more effects of administration of a compound to a living tissue of a subject, comprising: determining genotype information of the living tissue; providing the genotype information to a first portion of one or more neural networks, wherein the first portion comprises a visible neural network (VNN), wherein the VNN further comprises: a plurality of neurons are organized into a plurality of subsystems that corresponds to known or putative molecular subsystems; and a plurality of connections, wherein a connection between a first subsystem and a second subsystem of the VNN corresponds to a known or putative molecular pathway, wherein a weight of the connection is determined during training of the one or more neural networks and corresponds to how predictive the connection is to a drug response; receiving, from the VNN, a first embedding vector representing cell genotype information; providing a molecular fingerprint of the compound to a second portion of the one or more neural networks, wherein the second portion comprises an artificial neural network (ANN) that determines canonical vector representations of compounds: receiving, from the ANN, a second embedding vector representing compound structure information of the compound; and providing the first embedding vector and the second embedding vector to a third portion of the one or more neural networks, wherein the third portion comprises one or more layers of neurons trained to predict a response of the compound based on the genotype information; and receiving, from the third portion, a prediction of whether the subject will respond to the administration of the compound.

In embodiments, Relative Local Improvement in Predictive Power metric (RLIPP) scoring is used to identify subsystems of the plurality of subsystems that are most predictive of a response to the compound.

In embodiments, the third portion of the one or more neural networks comprises a single layer of neurons that are integrated to generate a predicted effect of a given genotype to the compound.

In embodiments, the genotype information comprises mutation statuses of a plurality of genes.

In embodiments, predication predicts the effects of the compound on a genotypically defined cancer tissue.

In embodiments, the method further comprises presenting a graphical interface comprising a visualization of the plurality of subsystems mediating the response.

In embodiments, the visualization provides an indication one or more metabolic pathways.

In embodiments, the compound comprise a chemotherapeutic, a targeted therapy, or a combination thereof.

In embodiments, the VNN is organized into a plurality of layers; a first layer of the plurality of layers that receives the genotype information represents genes; and one or more subsequent layers of the plurality of layers represent molecular subsystems of greater complexity and/or scale.

In embodiments, the VNN comprises six layers.

In embodiments, the ANN comprises a fully connected network.

In embodiments, the third portion of the one or more neural networks comprises a single layer of neurons that integrates the first embedding and second embedding to generate the prediction of whether the subject will respond to the administration of the compound.

In embodiments, a third aspect of the invention provides a method for combinatorial drug design, comprising: determining one or more subsystems mediating sensitivity of a living tissue to a first drug based at least in part on one or more neural networks comprising a visible neural network (VNN) that models the living tissue and an artificial neural network (ANN) that models the first drug: wherein the VNN comprises: a plurality of nodes are organized into a plurality of subsystems that corresponds to known or putative molecular subsystems; and a plurality of connections, wherein a connection between a first subsystem and a second subsystem of the VNN corresponds to a known or putative molecular pathway, wherein a weight of the connection is determined during training of the one or more neural networks and corresponds to how predictive the connection is to a drug response: wherein the ANN comprises a plurality of layers that are trained to determine structure information of the first drug; determining a set of genes based on membership in at least a portion of the one or more subsystems; determining a set of secondary drugs that target at least one of the set of target genes; and determining, based at least in part on the VNN and the ANN, at least one synergistic combination of the first drug and a second drug selected from the set of secondary drugs, wherein the at least one synergistic combination has greater predicted effectiveness than the first drug alone and the second drug alone.

In embodiments, the at least one synergistic combination further comprises a third drug selected from the set of secondary drugs, and the at least one synergistic combination has greater predicted effectiveness than the third drug alone.

In embodiments, the method further comprises: determining Relative Local Improvement in Predictive Power metric (RLIPP) scores for the plurality of subsystems; ranking the plurality of subsystems based on the RLIPP scores; and selecting the one or more subsystems as highest-ranking subsystems based on the RLIPP scores.

In embodiments, the first drug alone is determined to have a first effectiveness that is less than a threshold, indicating a resistance to the first drug alone; and the at least one synergistic combination is determined to have a second effectiveness that is greater than the threshold, indicating a sensitivity to the at least one synergistic combination.

In embodiments, the first drug comprise a chemotherapeutic, a targeted therapy, or a combination thereof.

In embodiments, the VNN is organized into a plurality of layers; a first layer of the plurality of layers receives genotype information of the living tissue and represents genes; and one or more subsequent layers of the plurality of layers represent molecular subsystems of greater complexity and/or scale.

In embodiments, wherein the VNN comprises six layers.

In embodiments, wherein the ANN comprises a fully connected network.

In embodiments, a fourth aspect of the invention provides a method for training one or more neural networks to predict a response of a living tissue to a compound using one or more neural networks, wherein the one or more neural networks comprises a first portion, a second portion, and a third portion, further wherein: the first portion of the one or more neural networks comprises a visible neural network (VNN) trained to determine a first embedding vector representing cell genotype information of the living tissue, wherein the VNN further comprises: a plurality of nodes are organized into a plurality of subsystems that corresponds to known or putative molecular subsystems; and a plurality of connections, wherein a connection between a first subsystem and a second subsystem of the VNN corresponds to a known or putative molecular pathway; the second portion comprises an artificial neural network (ANN) that is trained to determine a second embedding vector representing structure information of the compound from a molecular fingerprint of the compound; and the third portion comprises at least one layer of neurons that receive the first embedding vector and the second embedding vectors and generate the predicted response.

In embodiments, the genotype information comprises mutation statuses of a plurality of genes.

In embodiments, the training comprises: determining a Boolean logic circuit comprising a plurality of gates that approximates how the mutational status of the plurality of genes affects the predicted response.

In embodiments, the training comprises: determining weights of the plurality of connections based on how predictive a respective connection of the plurality is to the predicted response.

In embodiments, the compound comprise a chemotherapeutic, a targeted therapy, or a combination thereof.

In embodiments, the VNN is organized into a plurality of layers; a first layer of the plurality of layers that receives the genotype information represents genes; and one or more subsequent layers of the plurality of layers represent molecular subsystems of greater complexity and/or scale.

In embodiments, the VNN comprises six layers.

In embodiments, the ANN comprises a fully connected network.

In embodiments, the invention provides methods for preventing or treating a disease or condition in a subject comprising administering to a subject in need thereof with an effective amount of a compound or composition predicted by the system and methods herein.

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, $2^{nd}$ ed. (Sambrook et al., 1989); Oligonucleotide Synthesis (M. J. Gait, ed., 1984); Animal Cell Culture (R. I. Freshney, ed., 1987); Methods in Enzymology (Academic Press, Inc.); Current Protocols in Molecular Biology (F. M. Ausubel et al., eds., 1987, and periodic updates); PCR: The Polymerase Chain Reaction (Mullis et al., eds., 1994); Remington, The Science and Practice of Pharmacy, $20^{th}$ ed., (Lippincott, Williams & Wilkins 2003), and Remington, The Science and Practice of Pharmacy, $22^{th}$ ed., (Pharmaceutical Press and Philadelphia College of Pharmacy at University of the Sciences 2012).

As used herein, the terms "comprises," "comprising," "includes," "including," "has," "having," "contains", "containing," "characterized by," or any other variation thereof, are intended to encompass a non-exclusive inclusion, subject to any limitation explicitly indicated otherwise, of the recited components. For example, a fusion protein, a pharmaceutical composition, and/or a method that "comprises" a list of elements (e.g., components, features, or steps) is not necessarily limited to only those elements (or components or steps), but may include other elements (or components or steps) not expressly listed or inherent to the fusion protein, pharmaceutical composition and/or method.

As used herein, the transitional phrases "consists of" and "consisting of" exclude any element, step, or component not specified. For example, "consists of" or "consisting of" used in a claim would limit the claim to the components, materials or steps specifically recited in the claim except for impurities ordinarily associated therewith (i.e., impurities within a given component). When the phrase "consists of" or "consisting of" appears in a clause of the body of a claim, rather than immediately following the preamble, the phrase "consists of" or "consisting of" limits only the elements (or components or steps) set forth in that clause; other elements (or components) are not excluded from the claim as a whole.

As used herein, the transitional phrases "consists essentially of" and "consisting essentially of" are used to define a fusion protein, pharmaceutical composition, and/or method that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

The term "and/or" when used in a list of two or more items, means that any one of the listed items can be employed by itself or in combination with any one or more of the listed items. For example, the expression "A and/or B" is intended to mean either or both of A and B, i.e. A alone, B alone or A and B in combination. The expression "A, B and/or C" is intended to mean A alone, B alone, C alone, A and B in combination, A and C in combination, B and C in combination or A, B, and C in combination.

It is understood that aspects and embodiments of the invention described herein include "consisting" and/or "consisting essentially of" aspects and embodiments.

It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range. Values or ranges may be also be expressed herein as "about," from "about" one particular value, and/or to "about" another particular value. When such values or ranges are expressed, other embodiments disclosed include the specific value recited, from the one particular value, and/or to the other particular value. Similarly, when values are expressed as approximations, by use of the antecedent "about," it will be understood that the particular value forms another embodiment. It will be further understood that there are a number of values disclosed therein, and that each value is also herein disclosed as "about" that particular value in addition to the value itself. In embodiments, "about" can be used to mean, for example, within 10% of the recited value, within 5% of the recited value, or within 2% of the recited value.

As used herein, "patient" or "subject" means a human or animal subject to be treated.

As used herein the term "pharmaceutical composition" refers to pharmaceutically acceptable compositions, wherein the composition comprises a pharmaceutically active agent, and in some embodiments further comprises a pharmaceutically acceptable carrier. In some embodiments, the pharmaceutical composition may be a combination of pharmaceutically active agents and carriers.

The term "combination" refers to either a fixed combination in one dosage unit form, or a kit of parts for the combined administration where one or more active compounds and a combination partner (e.g., another drug as explained below, also referred to as "therapeutic agent" or "co-agent") may be administered independently at the same time or separately within time intervals. In some circumstances, the combination partners show a cooperative. e.g., synergistic effect. The terms "co-administration" or "combined administration" or the like as utilized herein are meant to encompass administration of the selected combination partner to a single subject in need thereof (e.g., a patient), and are intended to include treatment regimens in which the agents are not necessarily administered by the same route of administration or at the same time. The term "pharmaceutical combination" as used herein means a product that results from the mixing or combining of more than one active ingredient and includes both fixed and non-fixed combinations of the active ingredients. The term "fixed combination" means that the active ingredients, e.g., a compound and a combination partner, are both administered to a patient simultaneously in the form of a single entity or dosage. The term "non-fixed combination" means that the active ingredients, e.g., a compound and a combination partner, are both administered to a patient as separate entities either simultaneously, concurrently or sequentially with no specific time limits, wherein such administration provides therapeutically effective levels of the two compounds in the body of the patient. The latter also applies to cocktail therapy, e.g., the administration of three or more active ingredients.

As used herein the term "pharmaceutically acceptable" means approved by a regulatory agency of the Federal or a state government or listed in the U.S. Pharmacopoeia, other generally recognized pharmacopoeia in addition to other formulations that are safe for use in animals, and more particularly in humans and/or non-human mammals.

As used herein the term "pharmaceutically acceptable carrier" refers to an excipient, diluent, preservative, solubilizer, emulsifier, adjuvant, and/or vehicle with which demethylation compound(s), is administered. Such carriers may be sterile liquids, such as water and oils, including those of petroleum, animal, vegetable or synthetic origin, such as peanut oil, soybean oil, mineral oil, sesame oil and the like, polyethylene glycols, glycerine, propylene glycol or other synthetic solvents. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose may also be a carrier. Methods for producing compositions in combination with carriers are known to those of skill in the art. In some embodiments, the language "pharmaceutically acceptable carrier" is intended to include any and all solvents, dispersion media, coatings, isotonic and absorption delaying agents, and the like, compatible with pharmaceutical administration. The use of such media and agents for pharmaceutically active substances is well known in the art. See, e.g., Remington, The Science and Practice of Pharmacy, 20th ed., (Lippincott, Williams & Wilkins 2003). Except insofar as any conventional media or agent is incompatible with the active compound, such use in the compositions is contemplated.

As used herein, "therapeutically effective amount" refers to an amount of a pharmaceutically active compound(s) that is sufficient to treat or ameliorate, or in some manner reduce the symptoms associated with diseases and medical conditions. When used with reference to a method, the method is sufficiently effective to treat or ameliorate, or in some manner reduce the symptoms associated with diseases or conditions. For example, an effective amount in reference to diseases is that amount which is sufficient to block or prevent onset; or if disease pathology has begun, to palliate, ameliorate, stabilize, reverse or slow progression of the disease, or otherwise reduce pathological consequences of the disease. In any case, an effective amount may be given in single or divided doses.

As used herein, the terms "treat," "treatment," or "treating" embraces at least an amelioration of the symptoms associated with diseases in the patient, where amelioration is used in a broad sense to refer to at least a reduction in the magnitude of a parameter, e.g. a symptom associated with the disease or condition being treated. As such, "treatment" also includes situations where the disease, disorder, or pathological condition, or at least symptoms associated therewith, are completely inhibited (e.g. prevented from happening) or stopped (e.g. terminated) such that the patient no longer suffers from the condition, or at least the symptoms that characterize the condition.

As used herein, and unless otherwise specified, the terms "prevent," "preventing" and "prevention" refer to the prevention of the onset, recurrence or spread of a disease or disorder, or of one or more symptoms thereof. In certain embodiments, the terms refer to the treatment with or administration of a compound or dosage form provided herein, with or without one or more other additional active agent(s), prior to the onset of symptoms, particularly to subjects at risk of disease or disorders provided herein. The terms encompass the inhibition or reduction of a symptom of the particular disease. In certain embodiments, subjects with familial history of a disease are potential candidates for preventive regimens. In certain embodiments, subjects who have a history of recurring symptoms are also potential candidates for prevention. In this regard, the term "prevention" may be interchangeably used with the term "prophylactic treatment."

As used herein, and unless otherwise specified, a "prophylactically effective amount" of a compound is an amount sufficient to prevent a disease or disorder, or prevent its recurrence. A prophylactically effective amount of a compound means an amount of therapeutic agent, alone or in combination with one or more other agent(s), which provides a prophylactic benefit in the prevention of the disease. The term "prophylactically effective amount" can encompass an amount that improves overall prophylaxis or enhances the prophylactic efficacy of another prophylactic agent. As used herein, and unless otherwise specified, the term "subject" is defined herein to include animals such as mammals, including, but not limited to, primates (e.g., humans), cows, sheep, goats, horses, dogs, cats, rabbits, rats, mice, and the like. In specific embodiments, the subject is a human. The terms "subject" and "patient" are used interchangeably herein in reference, for example, to a mammalian subject, such as a human.

EXAMPLES

Results

Figure 1A:
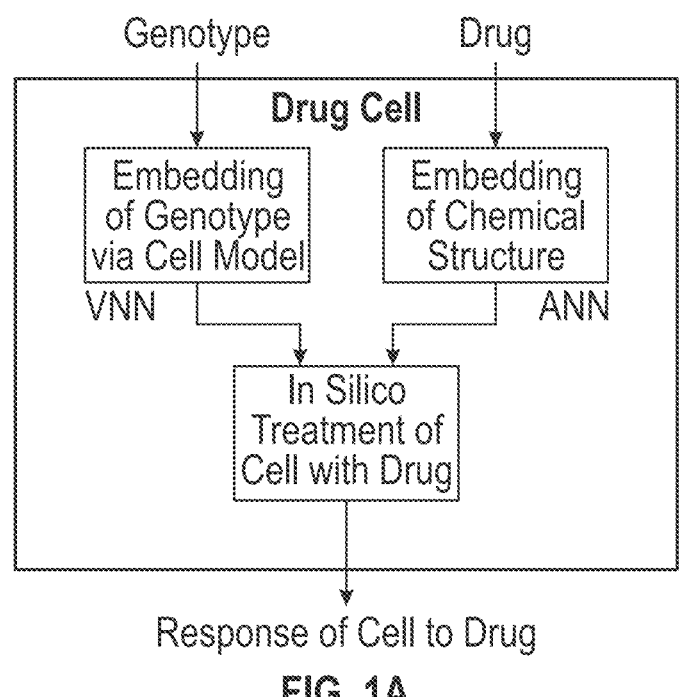
FIGS. 1A-1C show a DrugCell design.
Figure 1B:
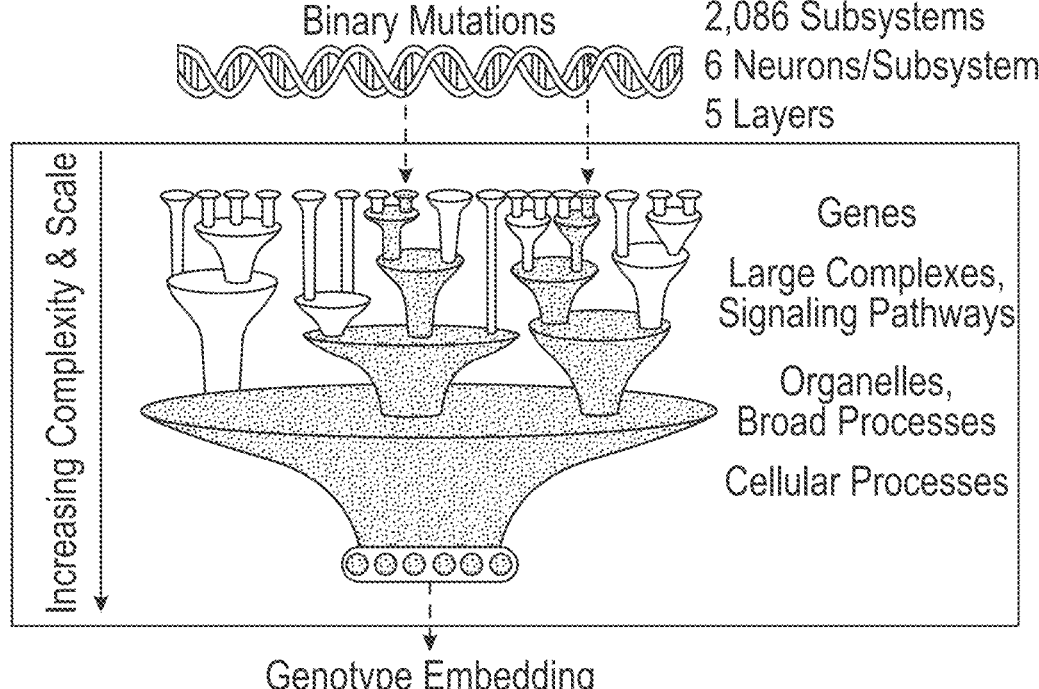
Figure 1C:
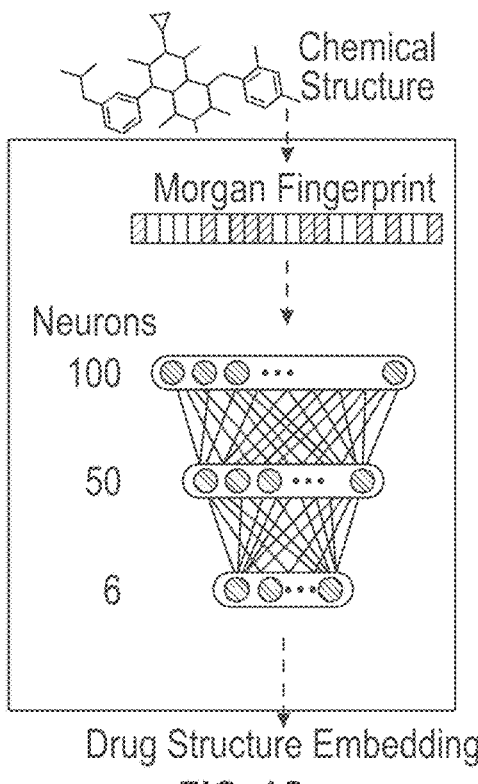
Figure 8A:
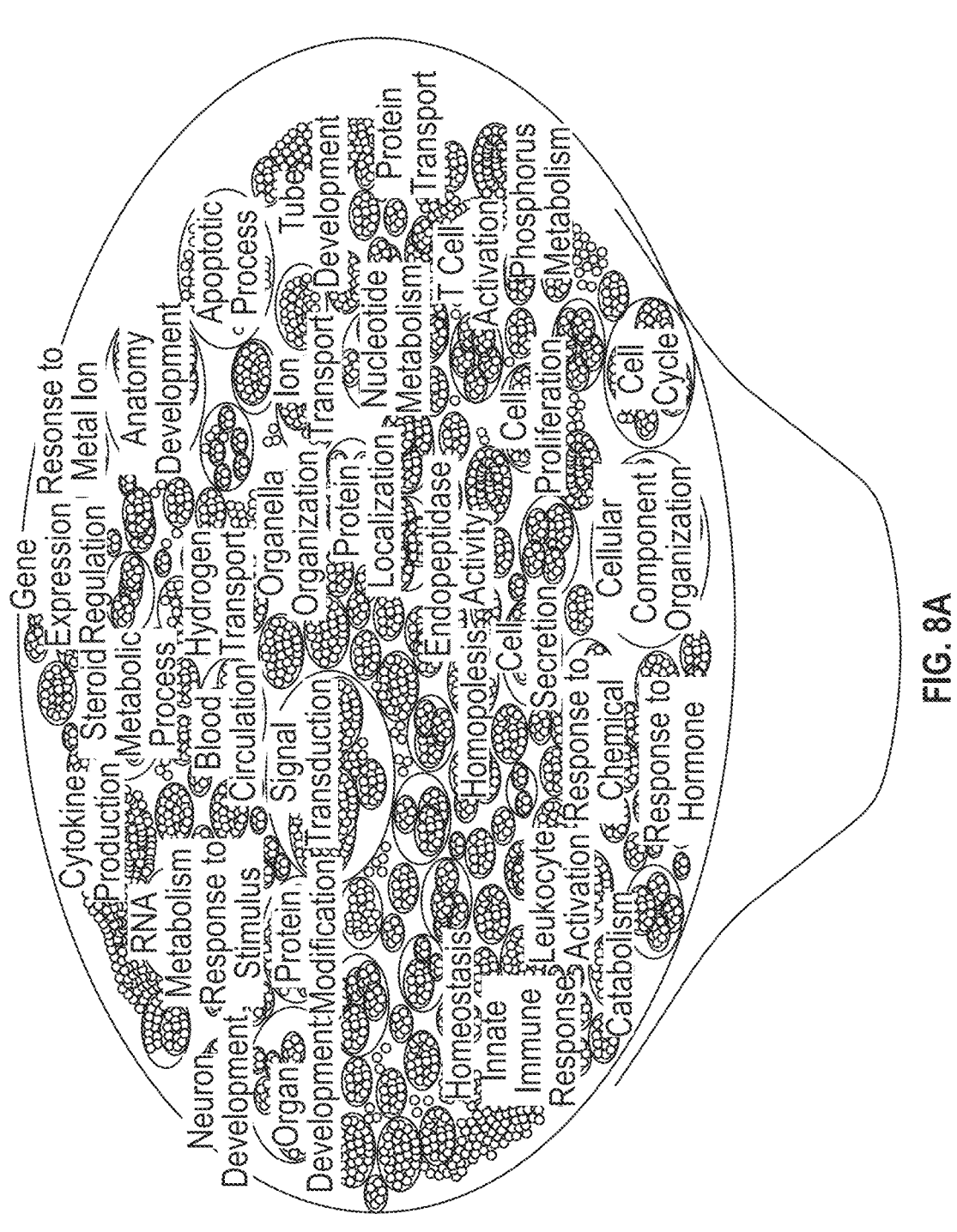
FIGS. 8A-8G show a characterization of DrugCell structure and training data, related to FIG. 1.
Figure 8B:
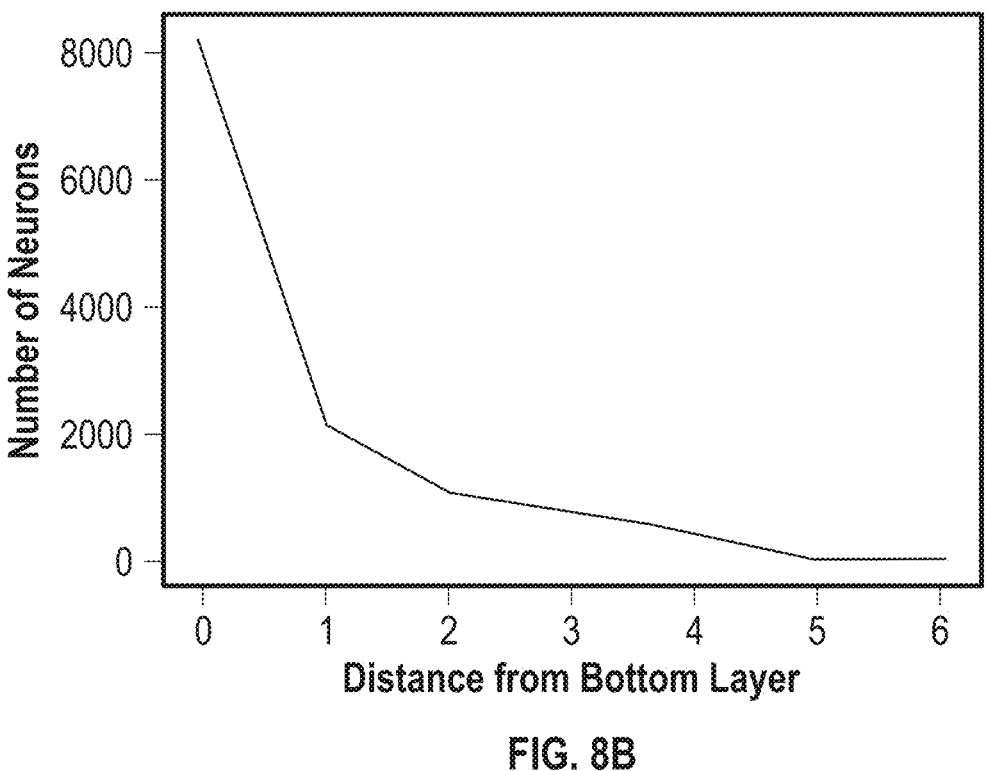

Design and training of an interpretable neural network of drug response. The cellular drug response is a complex phenomenon that depends on both biological and chemical factors (Turner et al., 2015). Current black-box models of drug response that use both these factors have begun to reach the limits of predictive performance (Table S1). In at least one embodiment, a model described herein is designed to that maintain this high level of predictive capability while gaining mechanistic interpretability of the model predictions. DrugCell was created as a neural network with two branches that captures both determinants of drug response in an interpretable model, (FIG. 1A, STAR Methods). The first branch was a VNN modeling the hierarchical organization of molecular subsystems in a human cell, drawn from 2,086 biological processes documented in the Gene Ontology database (Ashburner et al., 2000) FIG. 8A). Each of these subsystems, from those involving small protein complexes (e.g., β-catenin destruction complex) to larger signaling pathways (e.g., MAPK signaling pathway) to overarching cellular functions (e.g., glycolysis), was assigned a bank of artificial neurons to represent the state of that subsystem (FIG. 1B). Connectivity of neurons was set to mirror the biological hierarchy, so that neurons accept inputs only from those of child subsystems and send outputs only to those of parent systems, with connection weights determined during training. The use of multiple neurons per subsystem (here six, see STAR Methods) allowed cellular subsystems to be multifunctional, with distinct states able to adopt a range of values along multiple dimensions (Copley, 2012). The input layer of the hierarchy mapped to the mutation status of genes. The six neurons at the VNN output, corresponding to the root of the hierarchy, represented the embedded state of the whole cell based on its genotype (FIG. 1B). In total, the VNN used 12,516 neurons distributed hierarchically across 6 distinct layers (STAR Methods FIG. 8B). A VNN may be customized to have different numbers of layers—for example, 2, 3, 4, 5, 6, 7, 8, 9, 10, 15, etc. In some embodiments, the number of distinct layers of the VNN may be user-selectable. The second branch of DrugCell was an artificial neural network (ANN) embedding the Morgan fingerprint of a drug, a canonical vector representation of chemical structure (FIG. 1C, STAR Methods) (Rogers and Hahn, 2010). Outputs from the two branches of the model, the VNN embedding cell genotype and the ANN embedding drug structure, were combined in a single layer of neurons, which were then integrated to generate the response of a given genotype to a particular treatment (FIG. 1A).

Figure 8C:
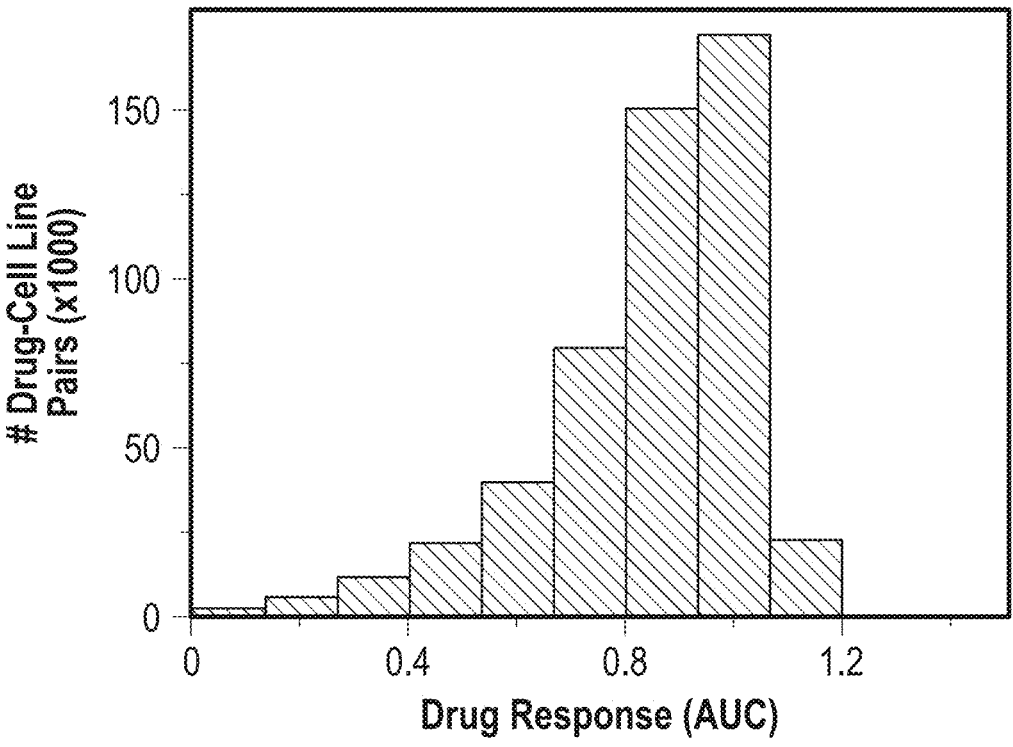
Figure 8D:
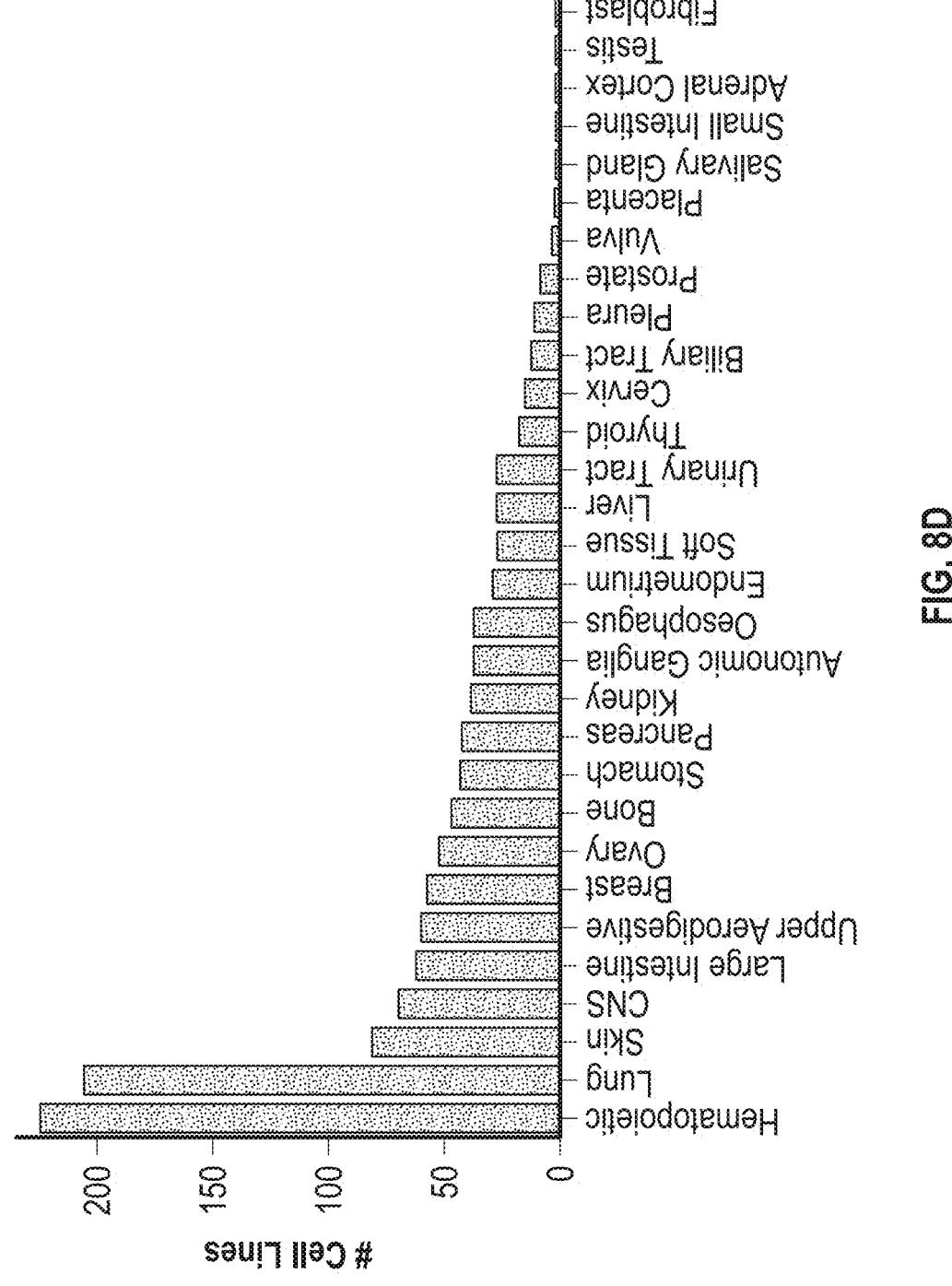
Figure 8E:
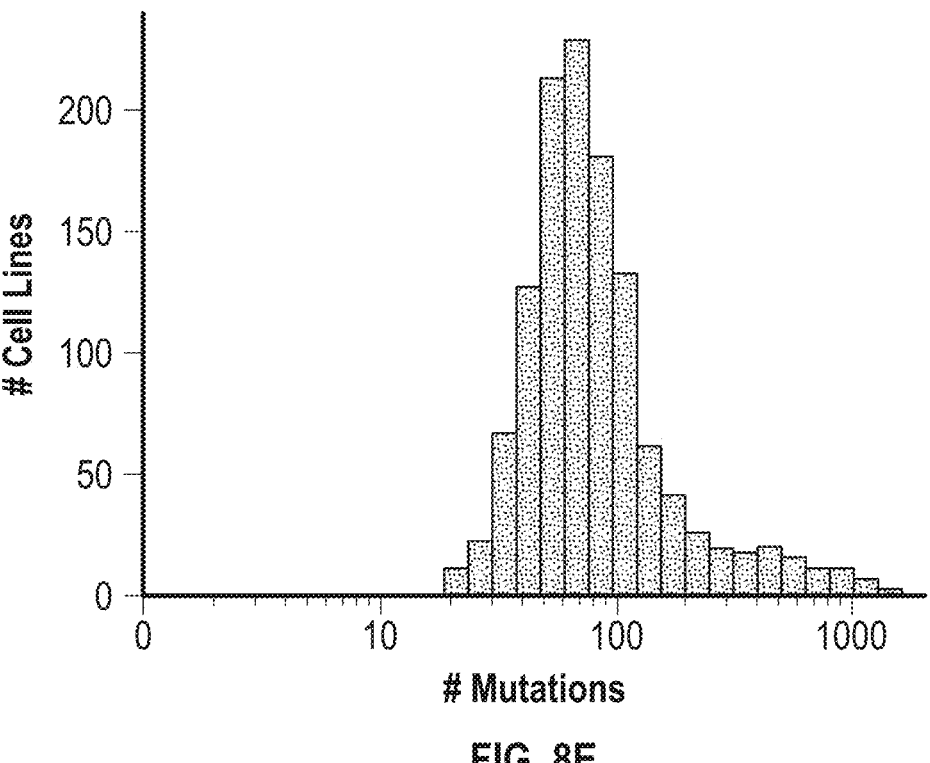
Figure 8F:
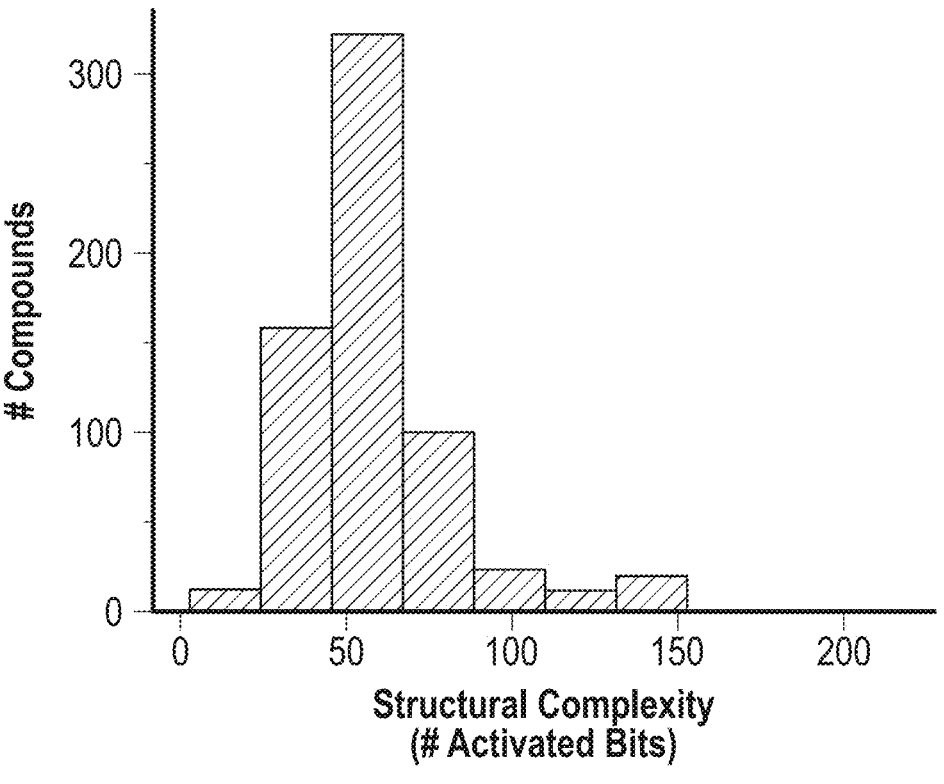
Figure 8G:
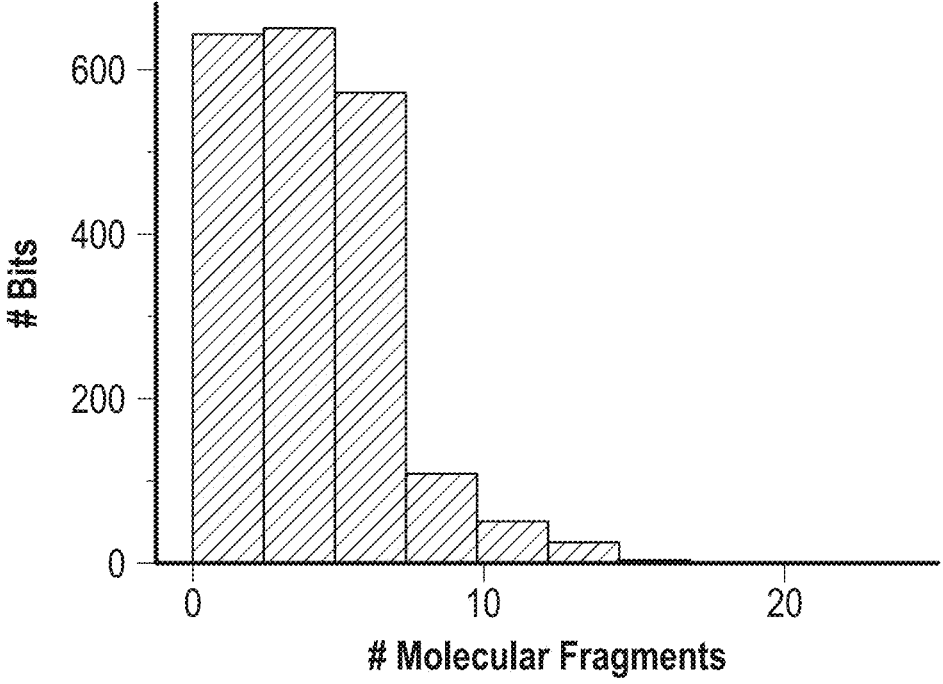

To train the model, data from two large cancer drug screening resources was harmonized: the Cancer Therapeutics Response Portal v2 (CTRPv2) and the Genomics of Drug Sensitivity in Cancer database (GDSC) (Seashore-Ludlow et al., 2015; Yang et al., 2013). The combined dataset consisted of 509,294 cell line-drug pairs, covering 684 drugs and 1,235 cell lines (FIG. 8C, STAR Methods). All major tissue types were represented, with hematopoietic and lung lineages the most prevalent (FIG. 8D). Each cell-line genotype was represented by a binary vector recording the mutational status (1=mutated. 0=non-mutated) of the top 15% most frequently mutated genes in cancer (n=3,008: median mutated genes per cell line=73 FIG. 8E). Each drug's chemical structure was represented by an average of 81 activated bits in the Morgan fingerprint vector, with each bit typically representing fewer than 10 molecular fragments (FIG. 8F). DrugCell was trained to associate each genotype-drug pair with its corresponding drug response, measured by the Area Under the dose response Curve (AUC, STAR Methods). The DrugCell model and its codebase are available for public download on GitHub (https://github-.com/idekerlab/DrugCell).

Figure 2A:
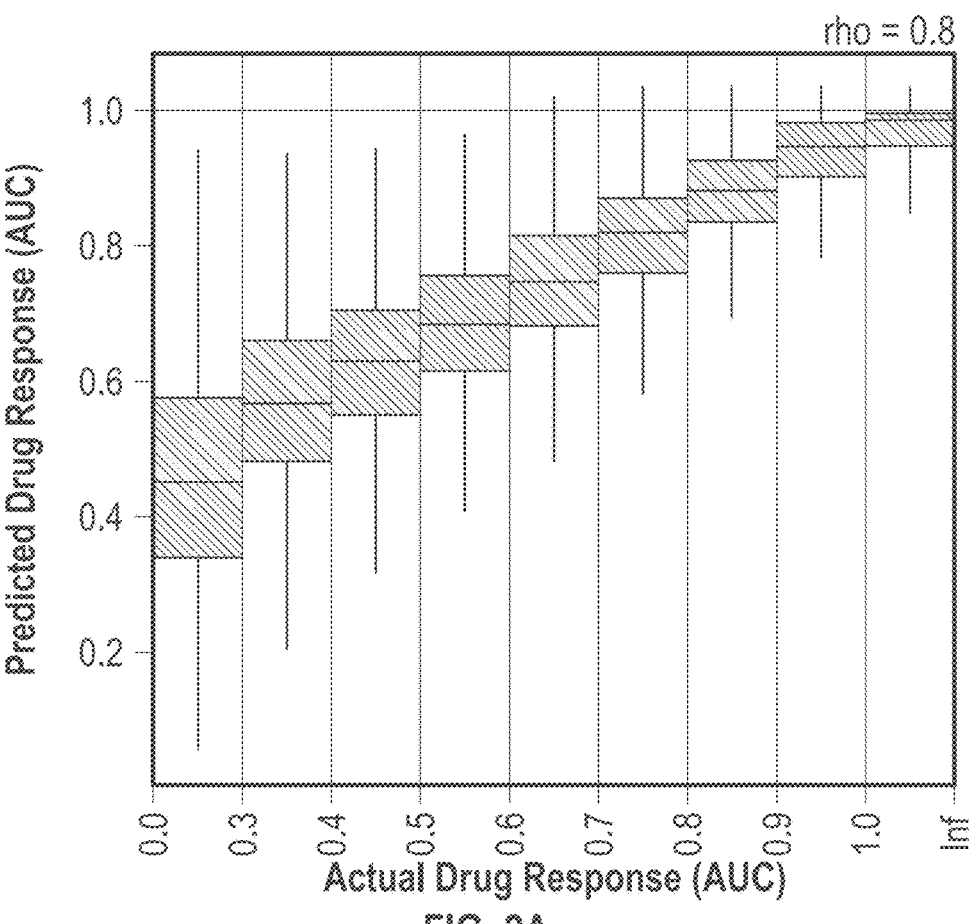
FIGS. 2A-2E shows predictive performance.
Figure 2B:
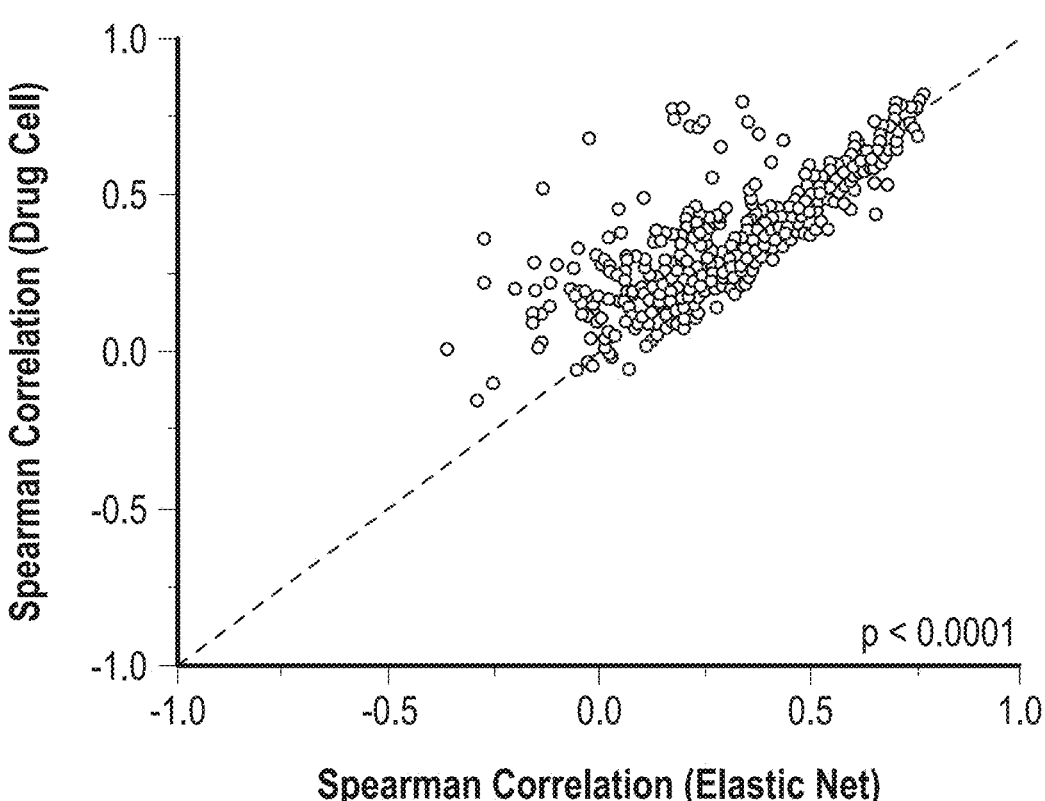
Figure 2C:
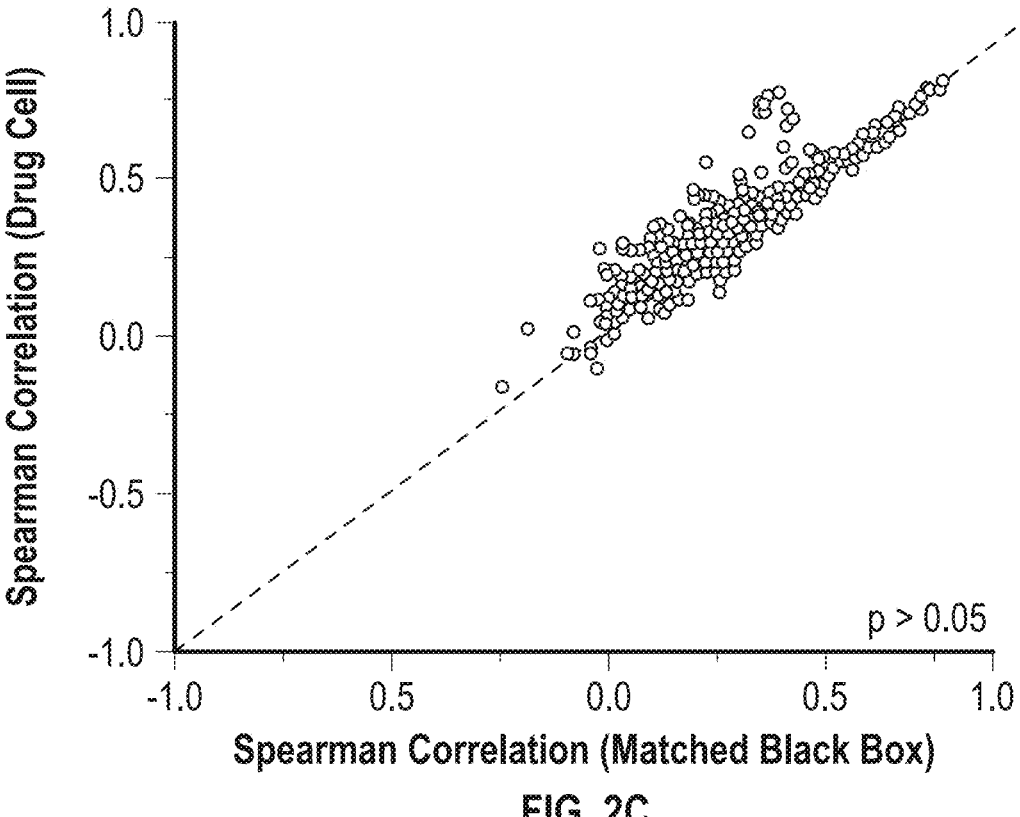
Figure 2D:
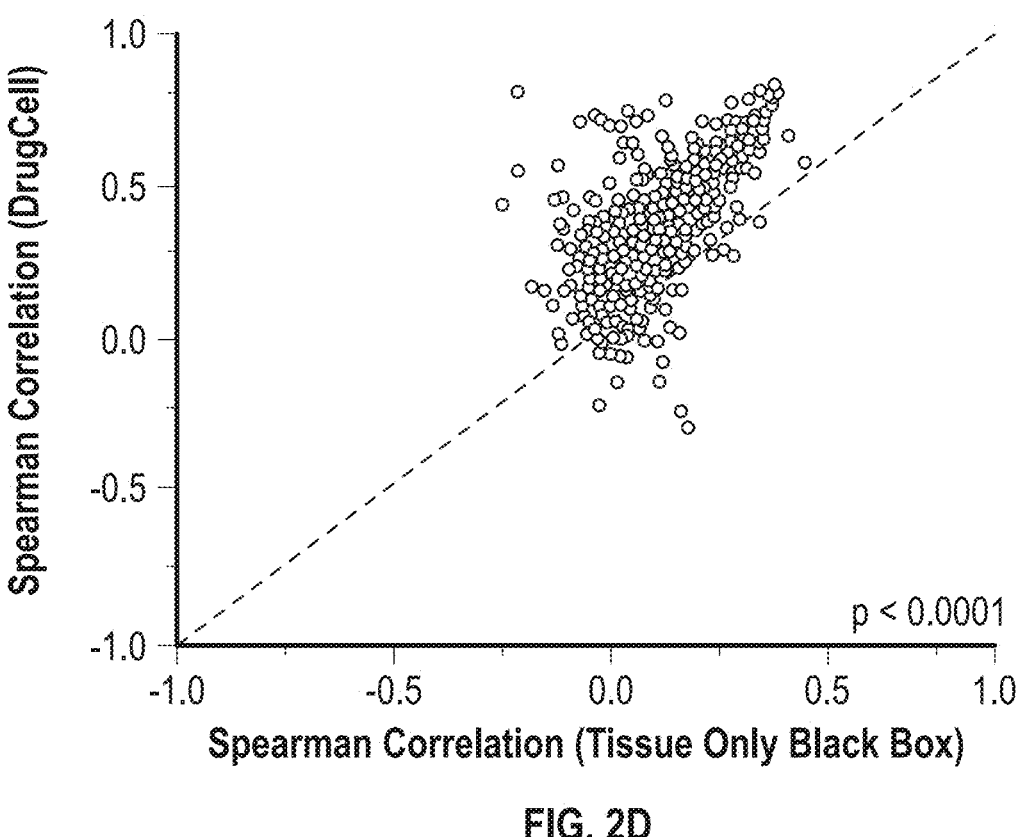

Interpretable modeling of drug response has no performance loss. The prediction accuracy of DrugCell was first assessed using the Spearman correlation (rho) between predicted versus observed AUC values in five-fold cross validation (STAR Methods). The total accuracy over all cell line-drug pairs was rho=0.80 (FIG. 2A). Further insight was achieved by computing the prediction accuracy for each drug individually, revealing a subpopulation of drugs with very high prediction accuracy (30% of drugs with rho>0.5) amid a much wider general distribution (range −0.29 to +0.83, median 0.37). These accuracies were significantly higher than those achieved for elastic net (median rho=0.35), a state-of-the-art regression technique used in many previous approaches to drug response prediction (Eskiocak et al., 2017; Iorio et al., 2016; Kuenzi et al., 2019; Potts et al., 2015) (FIG. 2B). DrugCell's drug-by-drug predictive performance was not significantly different from that of a conventional black-box ANN with matching numbers of neurons, layers, and connections (FIG. 2C). It was also comparable to previous efforts to incorporate chemical features of drugs into the response prediction (e.g., structure and physio-chemical properties such as solubility, lipophilicity and molecular weight), and it outperformed models that predict response using biological features alone (e.g., expression of biomarkers, point mutation, copy number variation and microsatellites). Finally, since knowledge of tissue type can be predictive of drug response even in the absence of other information (Iorio et al., 2016), it was considered that some of the performance of these models might be due to their ability to recognize the tissue type of a cell line from its input data (i.e., its mutational profile). Accordingly, DrugCell was compared to an equivalent neural network model trained on drug structure and a tissue label only (STAR Methods). DrugCell vastly outperformed this tissue-only model (median rho=0.18; FIG. 2D), indicating that the model had learned information from somatic mutations beyond the tissue of origin.

Figure 2E:
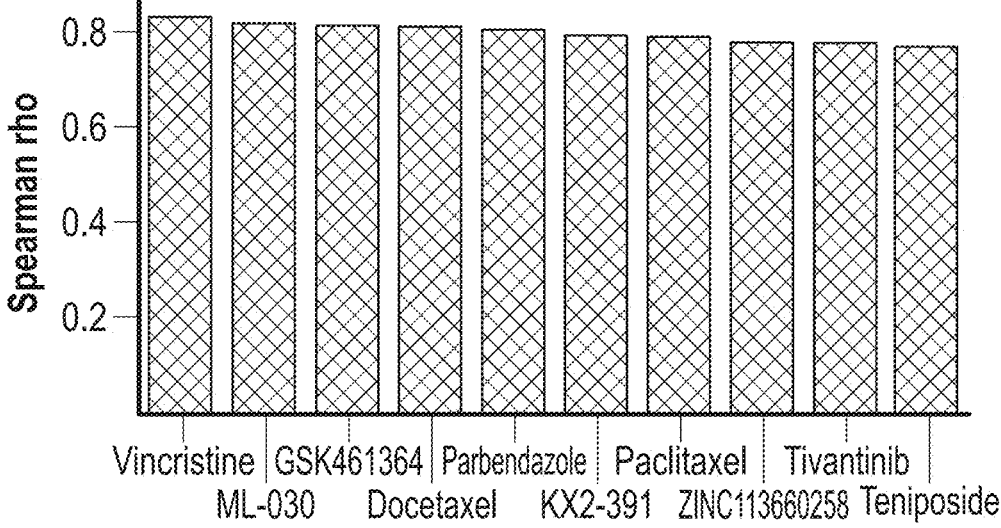
Figure 2E:
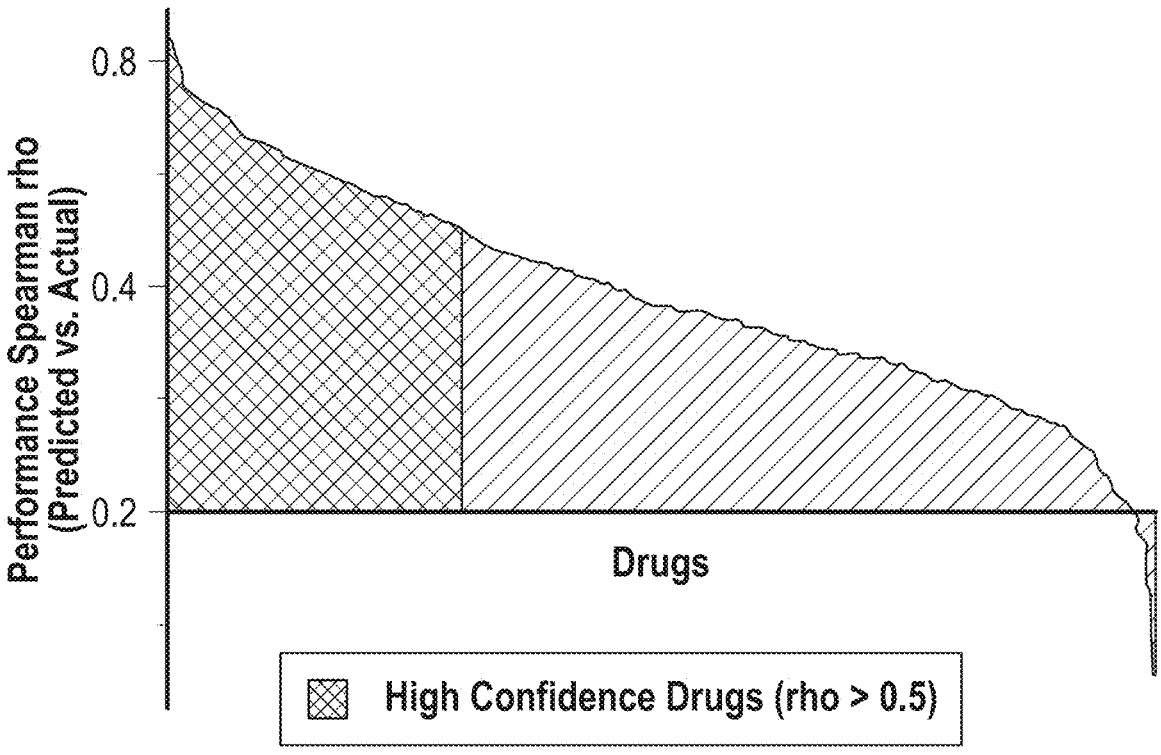
Figure 9A:
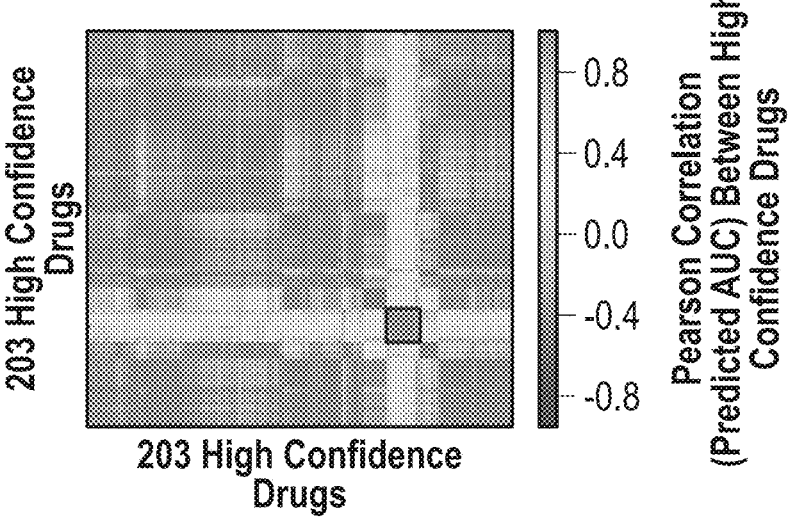
FIGS. 9A-9F shows characterization of DrugCell predictive performance, Related to FIG. 2.
Figure 9B:
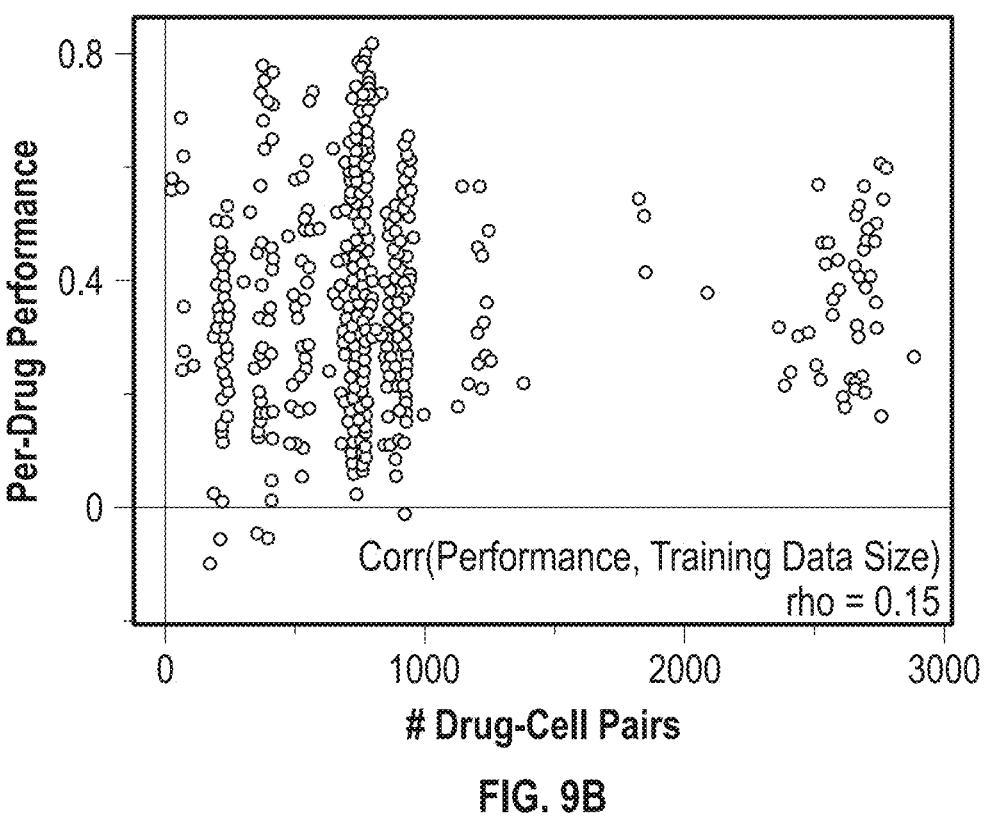
Figure 9C:
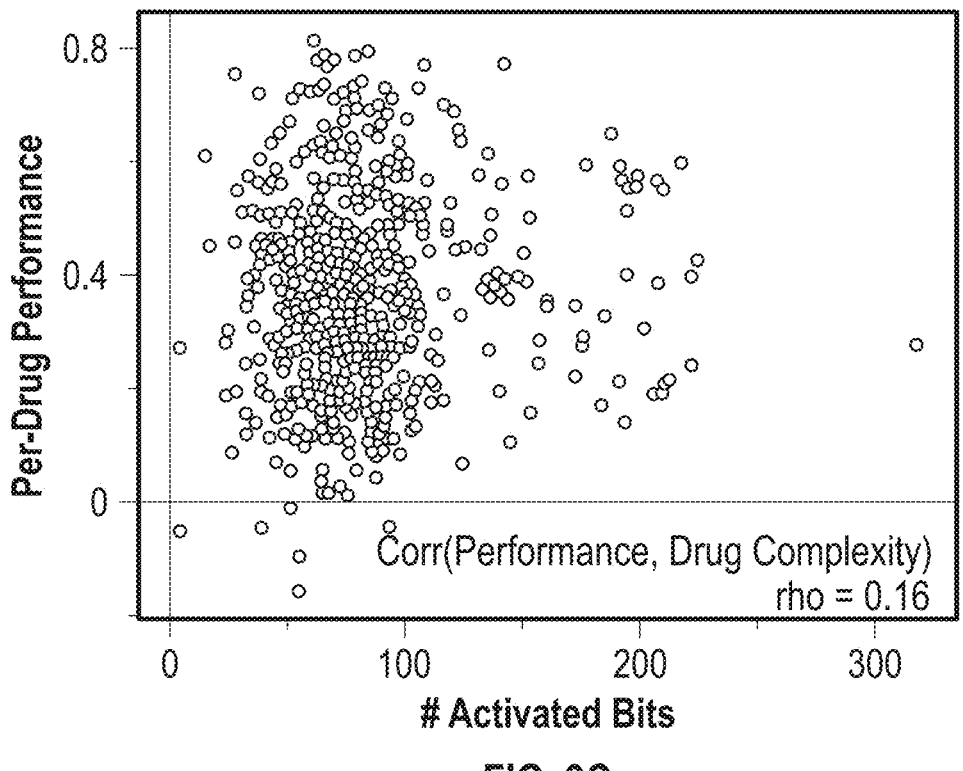
Figure 9D:
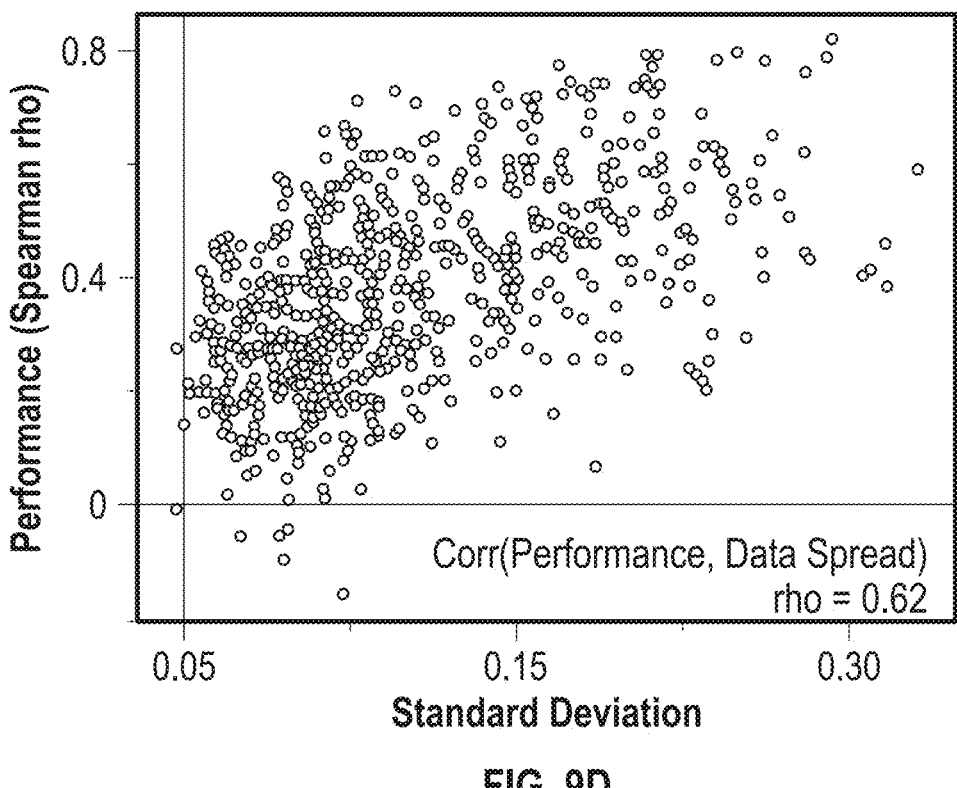
Figure 9E:
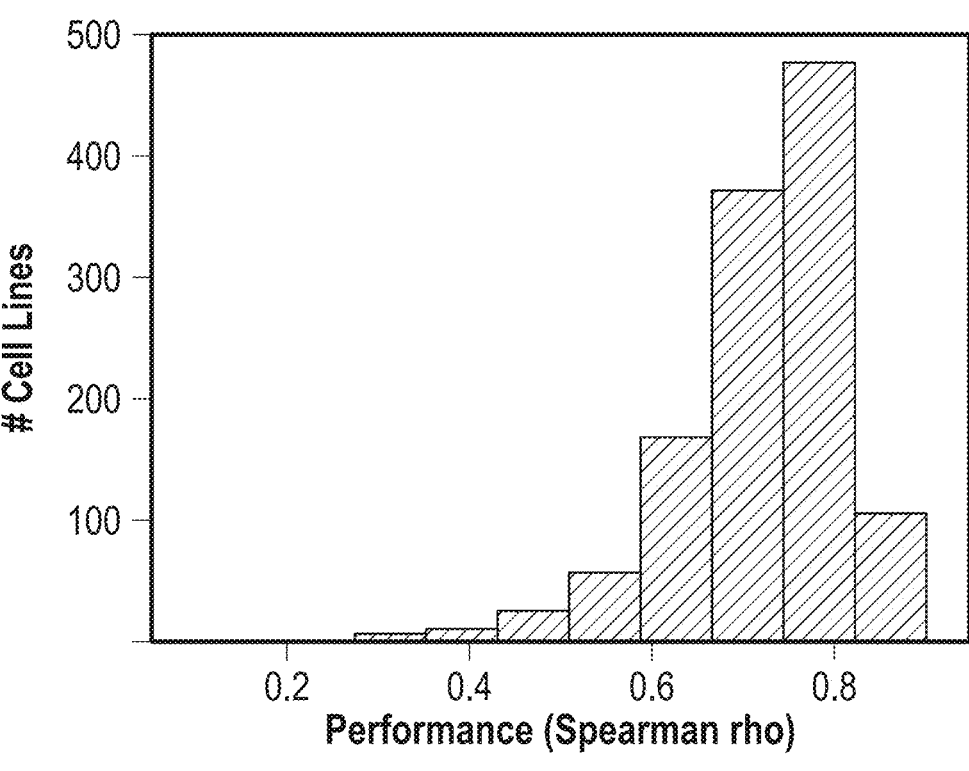

Compounds for which DrugCell predictions were most accurate came from diverse target classes, including chemotherapeutics (e.g., vincristine, teniposide) and targeted therapies (e.g., GSK461364 targeting PLK1, KX2-391 targeting Src; FIG. 2E). DrugCell maintained the specificity of the training data in that its predictions were specific to individual classes of drugs (e.g. MEK inhibitor predictions were highly specific) and did not simply reflect general drug toxicity (FIG. 9A). Predictive performance for a drug did not strongly correlate with the number of cell line-drug pairs used for training, nor with the structural complexity of a compound (number of activated bits FIG. 9B, FIG. 9C). Compounds eliciting a larger range of cell-line responses tended to be more predictable (FIG. 9D). Similarly, individual cell lines (FIG. 9E) and tissue types (FIG. 9F), which elicit a large range of responses, were in general highly predictable.

Figure 3A:
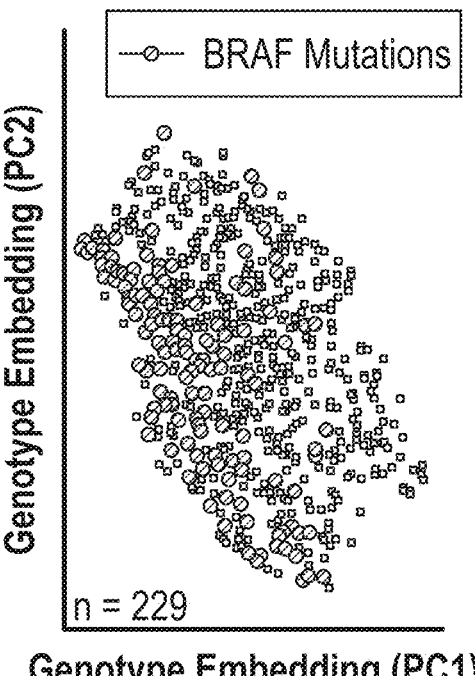
FIGS. 3A-3J show characterization of cancer cell states learned by DrugCell.
Figure 3B:
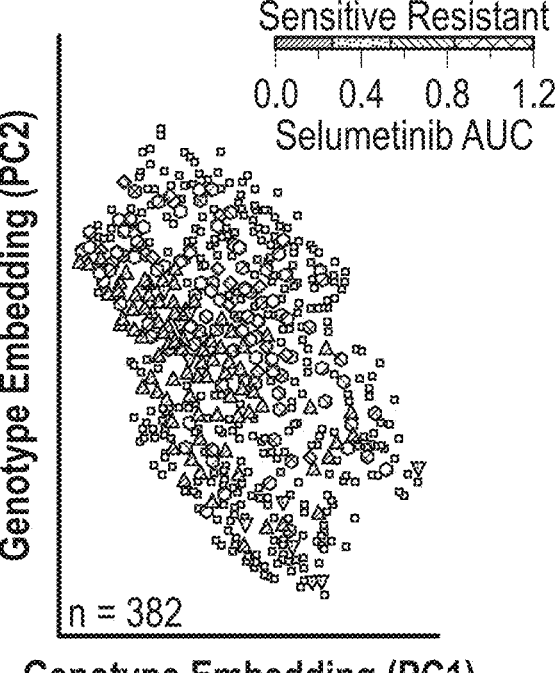
Figure 3C:
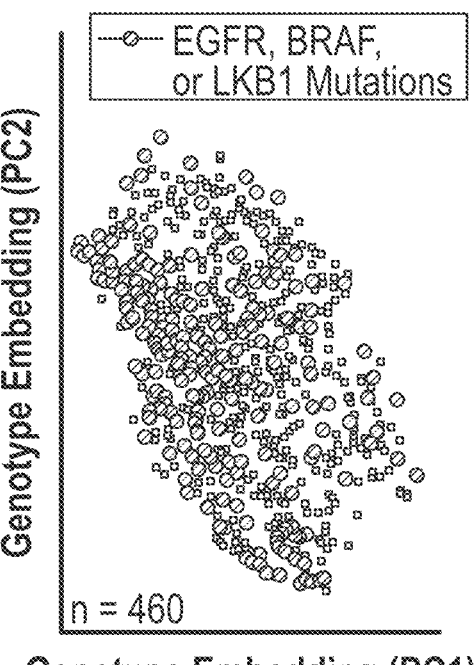
Figure 3D:
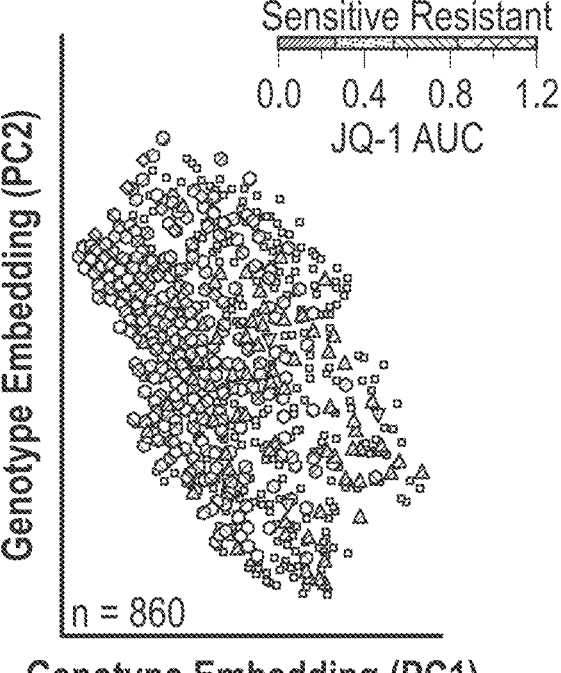
Figures 9F, 10A:
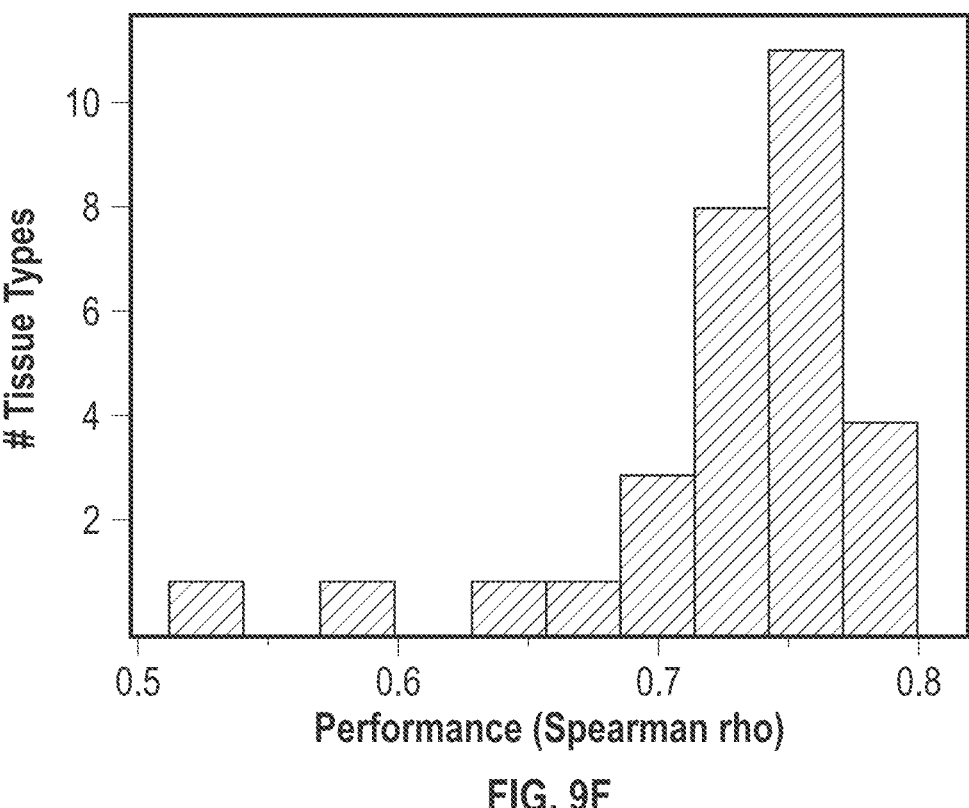
FIGS. 10A-10F show correspondence of subsystem embeddings with subsystem activities measured by RPPA, related to FIG. 3.
Figure 10B:
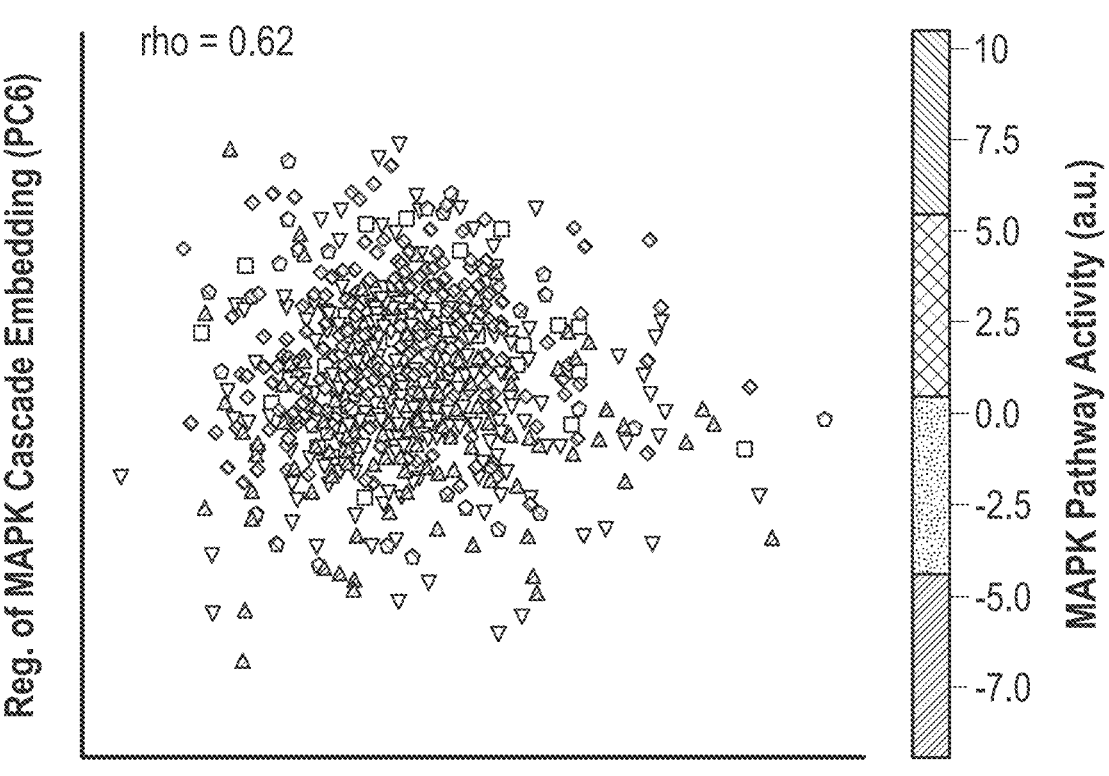
Figure 10C:
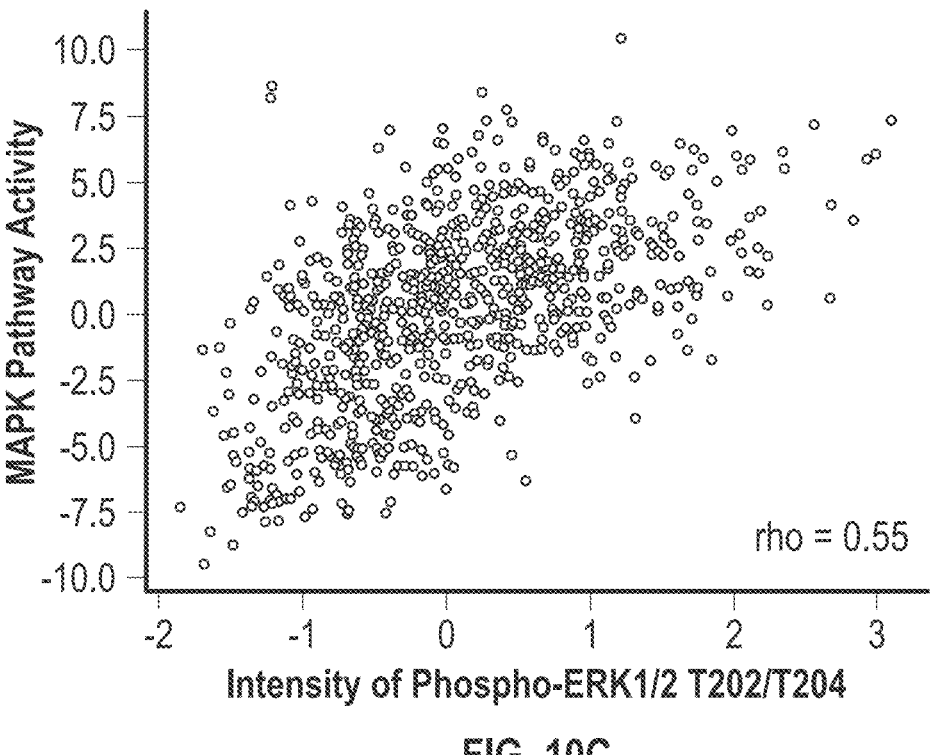
Figures 10D, 10E:
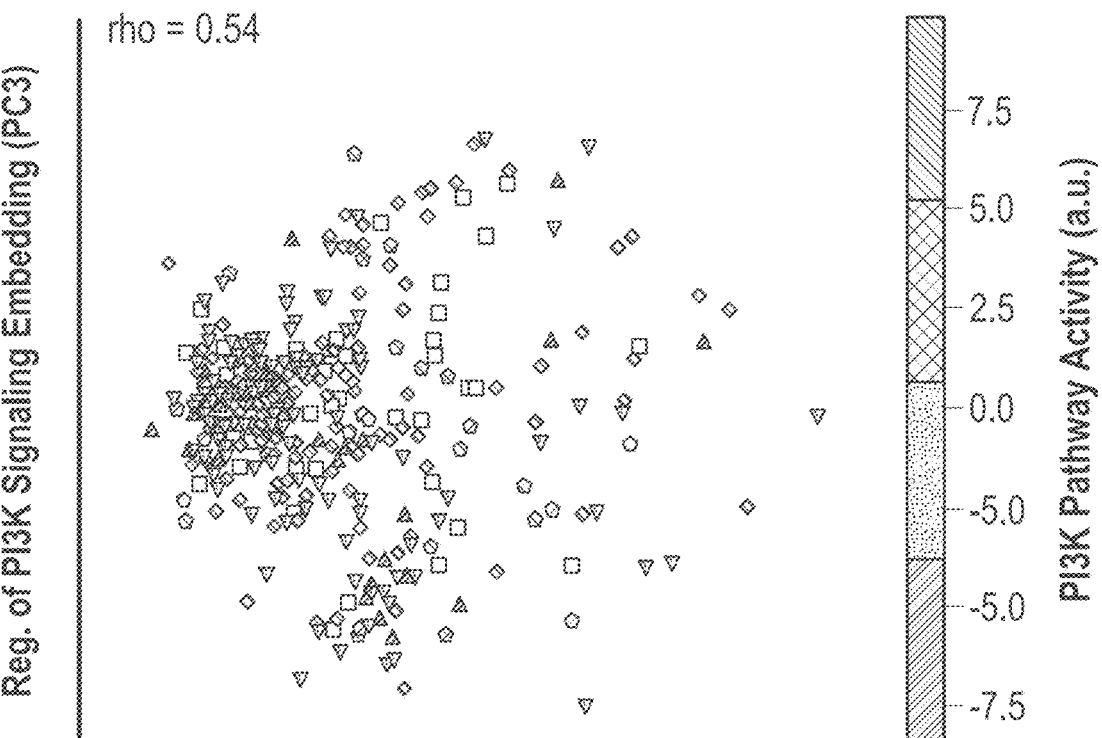
Figure 10F:
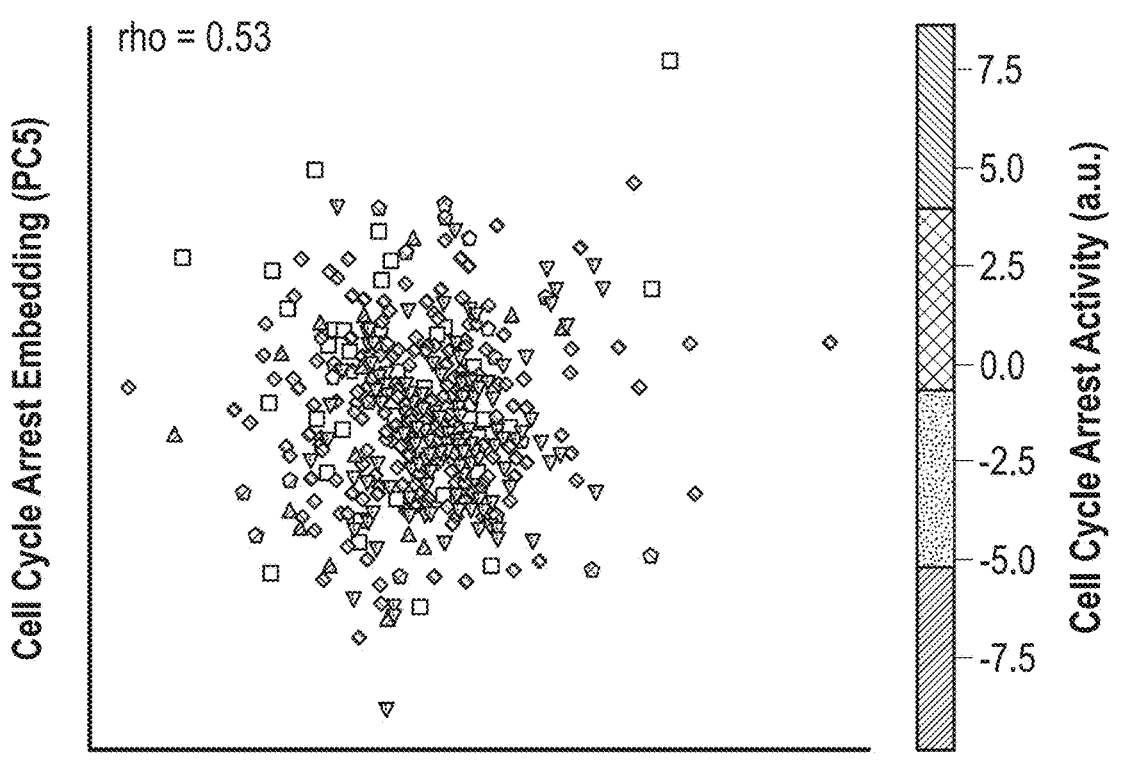

DrugCell learns mechanisms that mediate specific drug responses. Mechanistic interpretation was aided by the two model branches, which dissect the effects of genotype on the configuration of cell systems (genotype embedding) from the effects of chemical structure on drug activity within the cell (drug embedding, FIG. 1A). These embeddings were visually inspected by plotting the top two principal components (FIG. 3A-E). The genotype embedding from the VNN revealed a separation of genotypes according to mutations known to confer specific drug sensitivities, such as activating mutations in BRAF (FIG. 3A) which promote sensitivity to the MEK inhibitor selumetinib (FIG. 3B). The genotype embedding also distinguished mutations leading to drug resistance, such as mutations in EGFR (Yin et al., 2019). LKB1 (Shimamura et al., 2013), or BRAF (Ma et al., 2017) (FIG. 3C), which confer resistance to the BET-family inhibitor JQ-1 (FIG. 3D)). DrugCell embeddings of individual subsystems within the VNN were similarly inspected and it was found that many were in agreement with subsystem activities measured experimentally by an independent analysis of protein abundances and phosphorylation states using reverse phase protein arrays (RPPA; FIG. 10A; STAR Methods). For example, DrugCell accurately captured MAPK pathway activity within the subsystem embedding (FIG. 10B), which significantly correlated with ERK1/2 phosphorylation (FIG. 10C). Overall, the majority of DrugCell subsystems were well correlated with the RPPA measurements of those subsystems (note bimodal distribution of correlation FIG. 10A). Other accurately captured subsystems included Proteolysis (FIG. 10D), Regulation of PI3K signaling (FIG. 10E) and Cell Cycle Arrest (FIG. 10F).

Figure 3E:
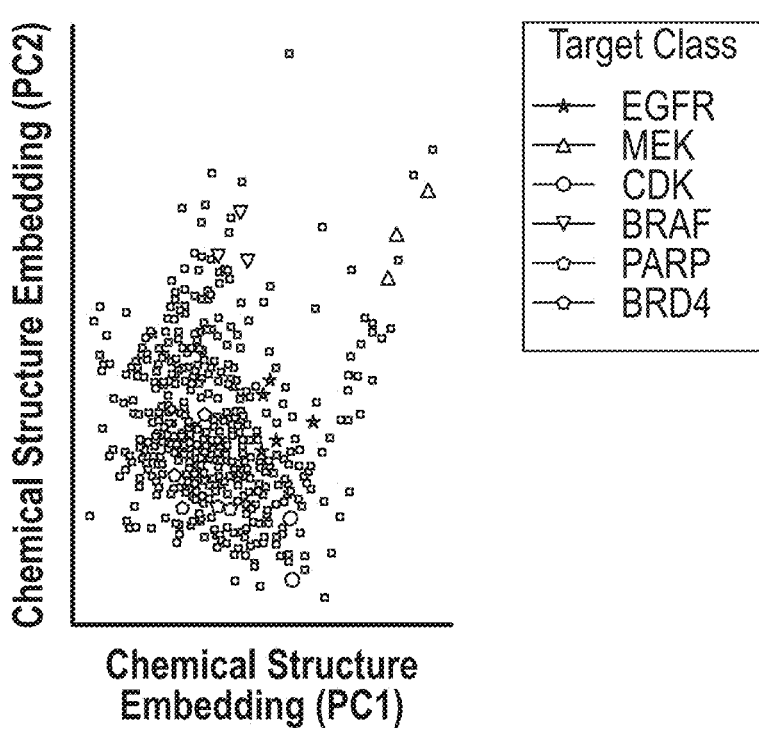
Figure 11A:
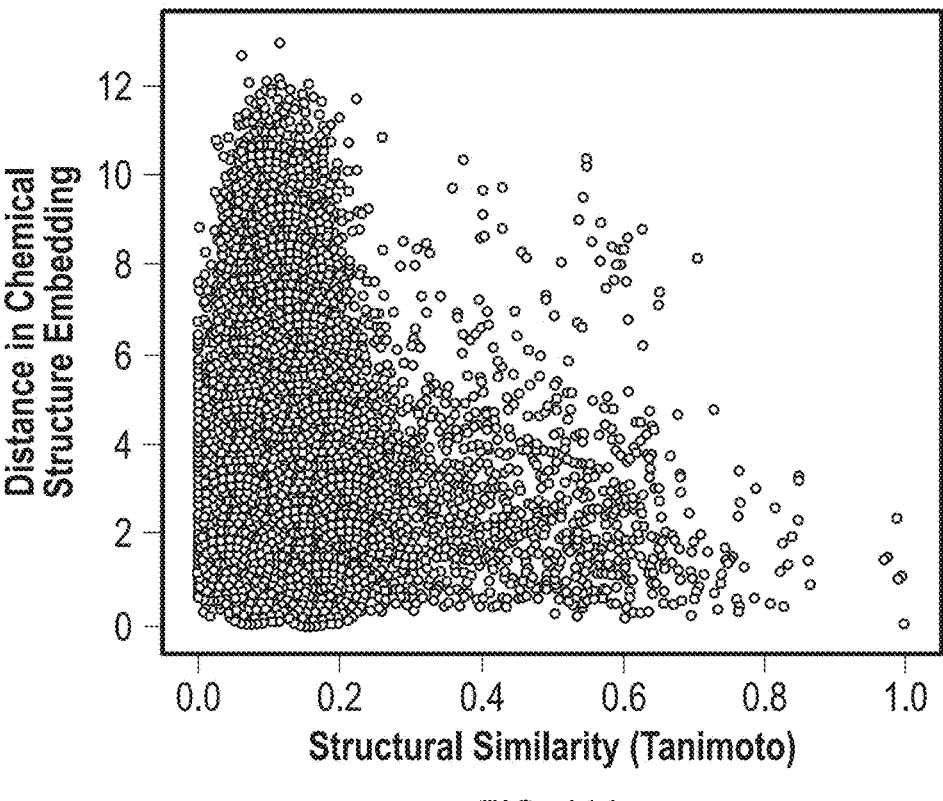
FIGS. 11A-D show characterization of chemical structure embedding, related to FIG. 3.
Figures 11B, 11C:
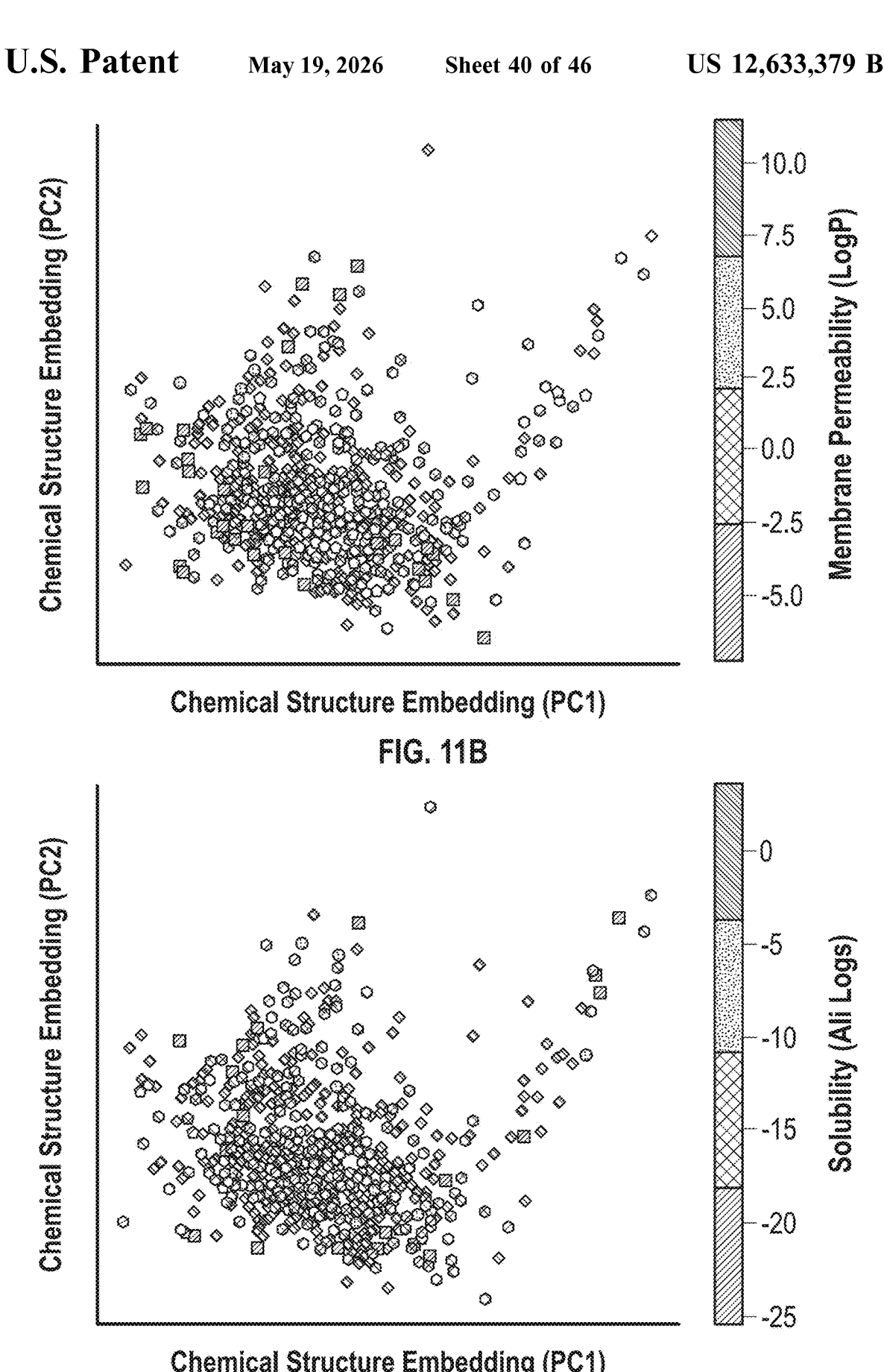
Figure 11D:
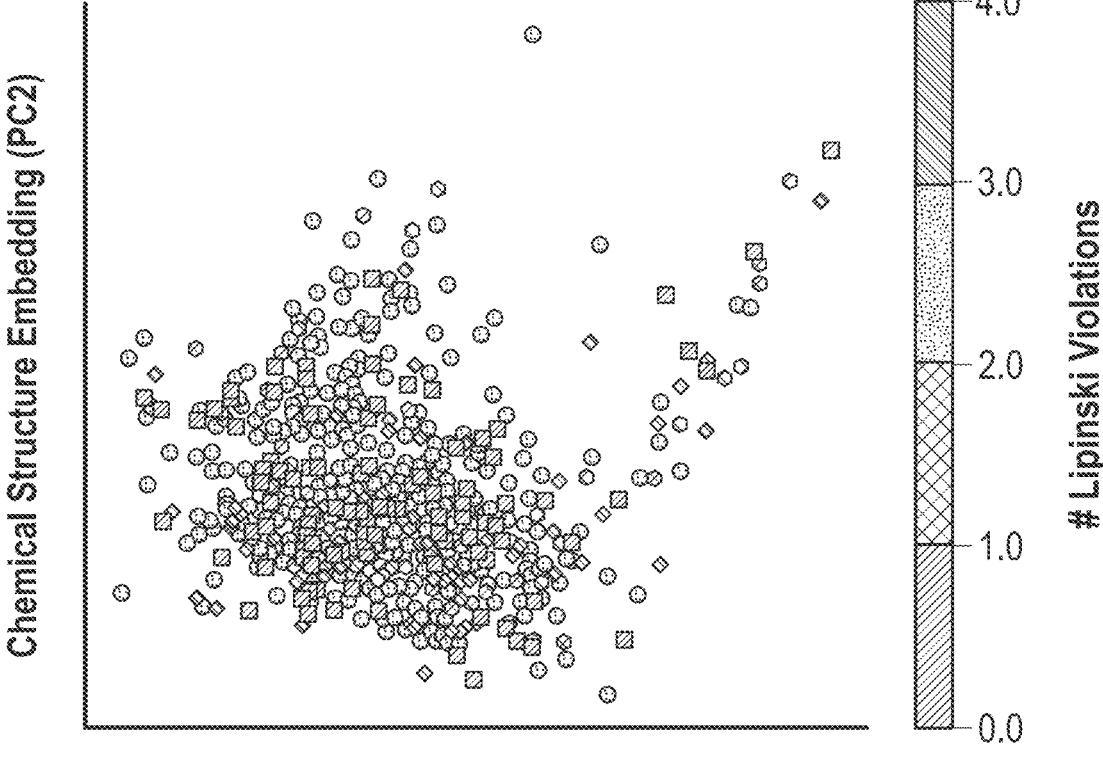

Inspection of the drug embedding from the ANN revealed a stratification of drugs based on their mechanisms of action within major drug target classes (FIG. 3E). The distance between each pair of drugs in the chemical structure embedding did not correlate with their overall chemical similarity (FIG. 11A), consistent with previous studies of drug activity and chemical structure (Breinig et al., 2015). Since the training data solely consisted of drugs and drug-like molecules, the chemical structural embedding did not stratify drugs on chemical features such as membrane permeability (FIG. 11B), solubility (FIG. 11C) or pharmacodynamic properties (Lipinski FIG. 11D). Together these results suggest that DrugCell is able to learn key features of genotype that govern drug sensitivity and resistance, as well as features of chemical structure that govern drug biological activity.

Figure 3F:
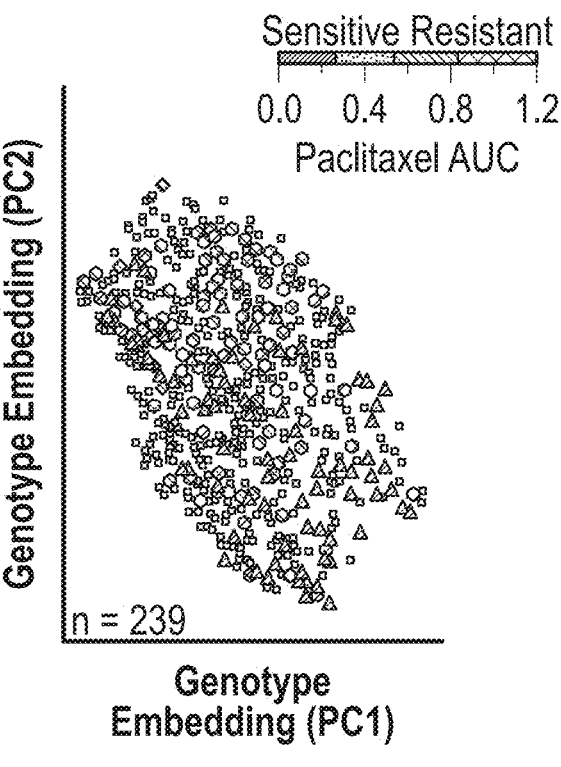
Figure 3G:
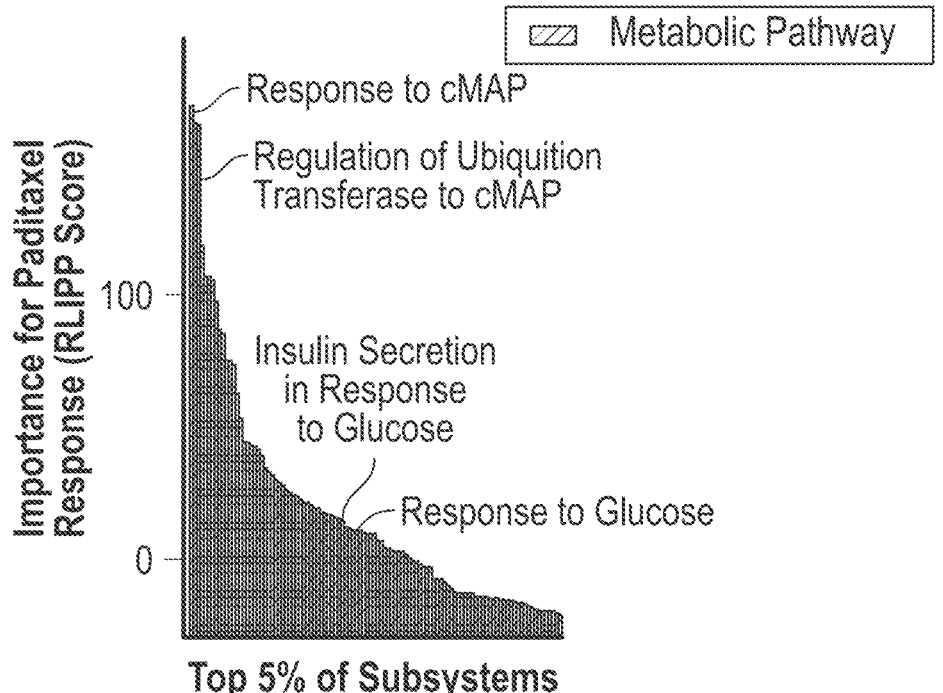
Figure 3H:
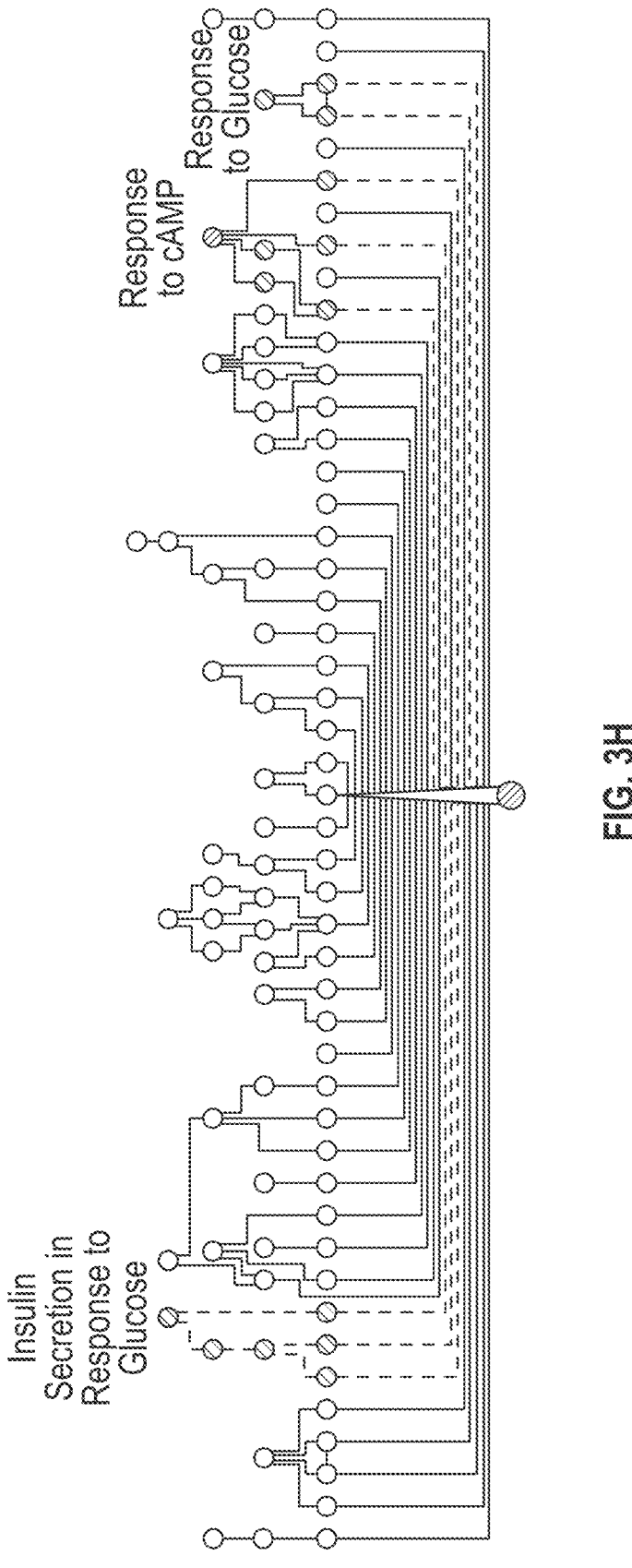
Figure 3I:
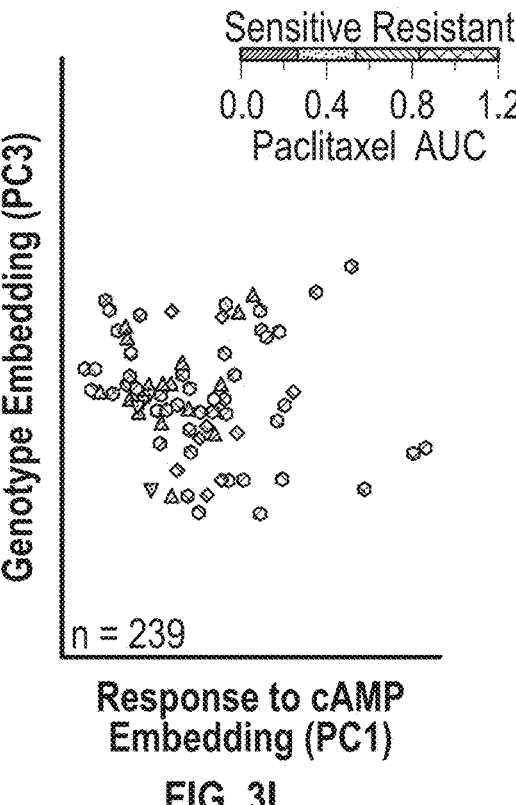
Figure 3J:
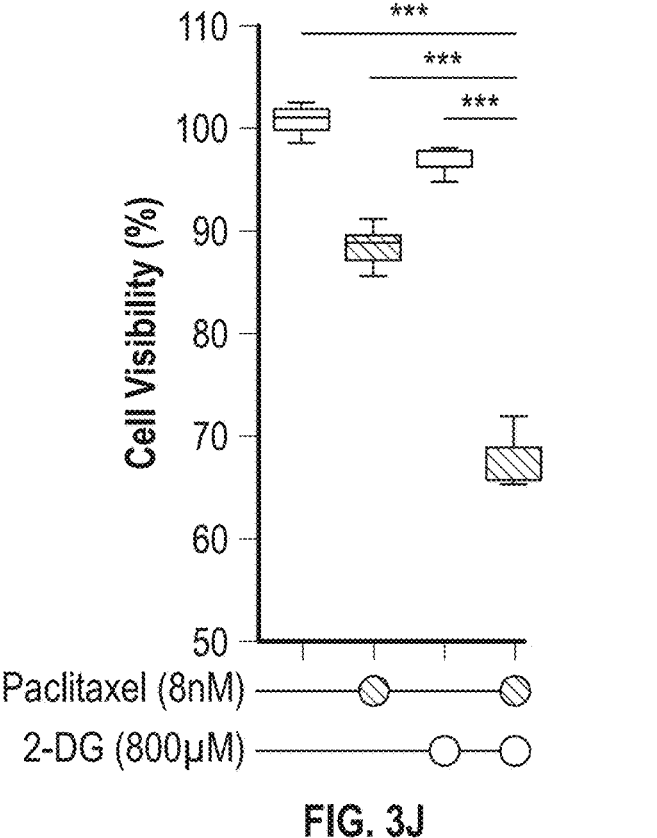

Since DrugCell's VNN is structured according to the hierarchy of biological subsystems comprising a human cell, its output (genotype embedding) is the result of state changes in particular subsystems within that hierarchy. To identify the most important of these subsystems, subsystems were scored by the degree to which their states were significantly more predictive of a drug response than the states of their child subsystems using the Relative Local Improvement in Predictive Power metric (RLIPP. STAR Methods) (Ma et al., 2018). As an initial proof of concept, RLIPP scoring was used to identify subsystems important for the cellular response to taxol (paclitaxel), an agent that stabilizes microtubules (FIGS. 2E and 3F). Among the top scores for paclitaxel, many subsystems were metabolic processes (hypergeometric $p<0.05$; FIGS. 3G and 3H) including Response to CAMP (top score) along with Insulin secretion in response to glucose and Response to glucose. It was confirmed by inspection that the states of these subsystems had the ability to stratify paclitaxel sensitive versus resistant cell lines (e.g., Response to CAMP subsystem, FIG. 3I). Given these underlying metabolic pathways, it was hypothesized that paclitaxel efficacy might be modulated by metabolic perturbation. A427 cells were therefore exposed to three different treatments—paclitaxel, the glycolysis inhibitor 2-deoxyglucose (2-DG), or a combination of the two—and found that the combination was substantially more effective than either individual compound (FIG. 3J).

Figure 12A:
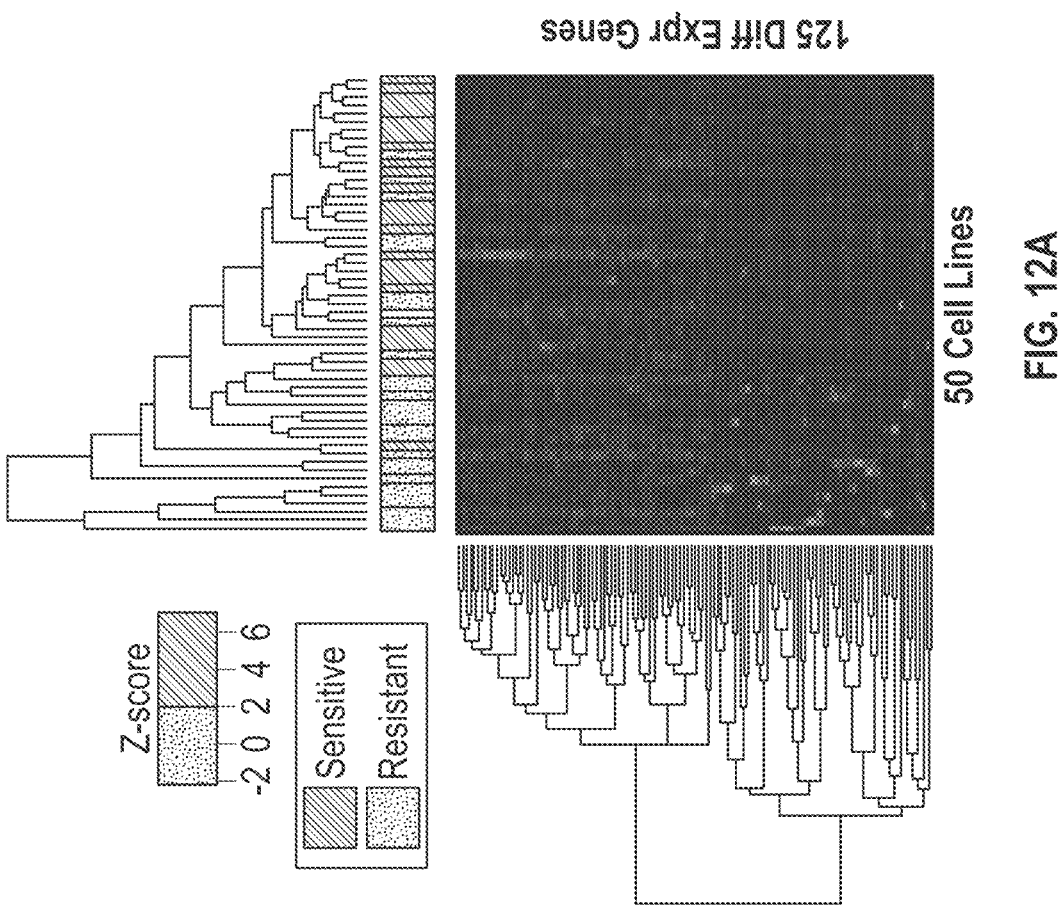
Figure 12A:
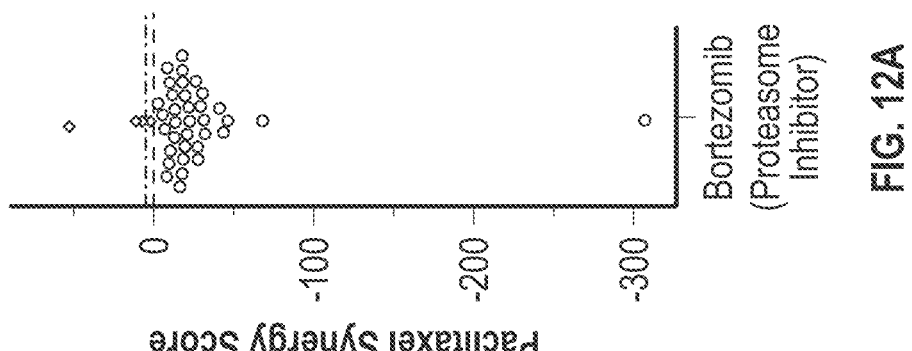
Figure 12C:
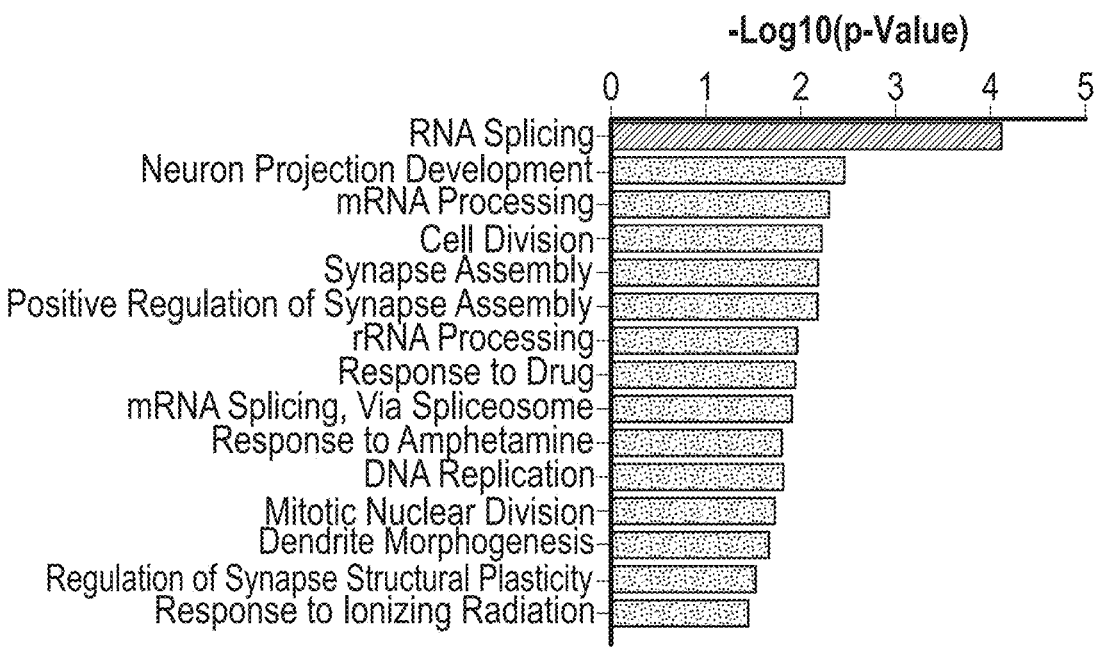
Figure 12D:
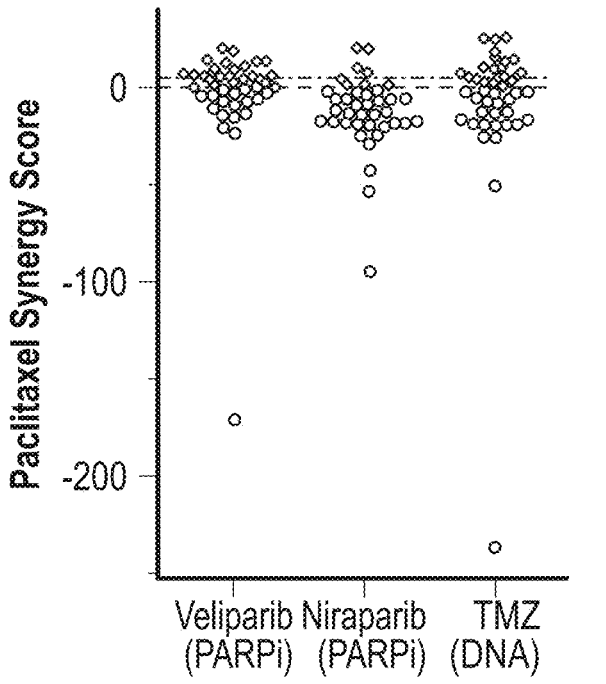
Figure 13:
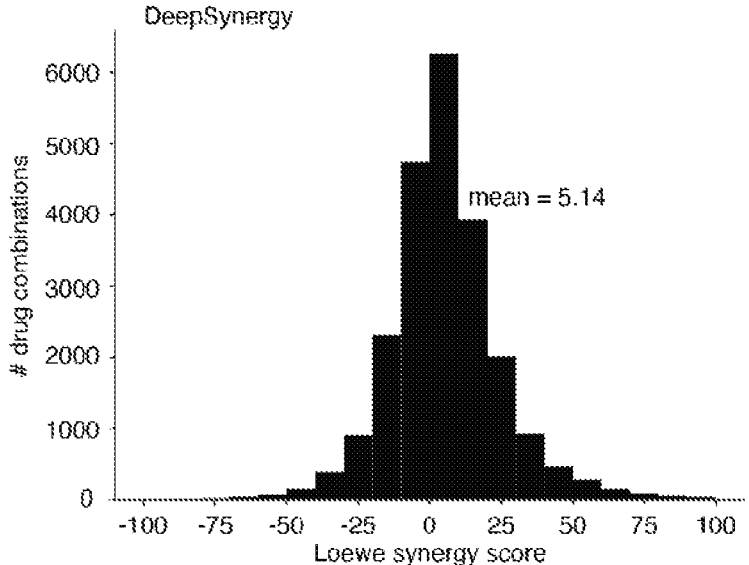
FIG. 13. Distribution of Loewe and Bliss synergy values in DeepSynergy, related to FIG. 5. Histogram of Loewe synergy scores across all drug combinations-cell line pairs in the DeepSynergy dataset (Preuer et al., 2018).

A similar analysis was performed for the next (second-most) important subsystem, Regulation of ubiquitin-protein transferase activity (FIG. 3G). Paclitaxel was combined with perturbation of ubiquitin-dependent protein degradation via the proteasome inhibitor bortezomib (FIG. 12A). These treatments were found to be antagonistic, consistent with recent findings showing that glycolysis is subject to negative physical regulation by ubiquitin ligases at the cytoskeleton (Park et al., 2020). Ubiquitin and subsystems were also identified for docetaxel, a sister compound. Notably, these DrugCell pathways were not identified by earlier analyses of genetic mutations and were distinct from those identified by differential mRNA expression analysis of paclitaxel sensitive versus resistant lines (FIGS. 12B and 12C). Unlike the glycolytic perturbations emerging from DrugCell analysis, combination treatments suggested by differentially expressed pathways were not successful at enhancing paclitaxel efficacy (FIG. 12D).

Moving beyond paclitaxel to examine the important subsystems identified for other drugs, it was found that some of these subsystems corresponded to previously identified mechanisms of drug sensitivity, while many others were novel pathways warranting further investigation. In particular, 60 drugs were examined for which pan-cancer diagnostic gene mutations had been reported by an earlier analysis of the GDSC dataset using type-II error ANOVA modeling (Iorio et al., 2016). For a number of drugs, DrugCell recovered the previously reported diagnostic gene(s) within the top subsystem (4 drugs) or top 10 subsystems (14 drugs, upper 0.4 percentile of subsystems). For the vast majority however (56 drugs), DrugCell achieved better predictive performance by consulting additional, or different, markers than had been previously reported.

Figure 4A:
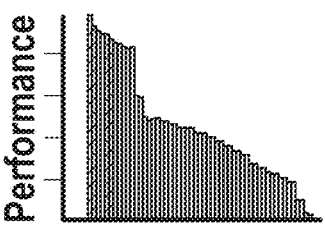
Figure 4A:
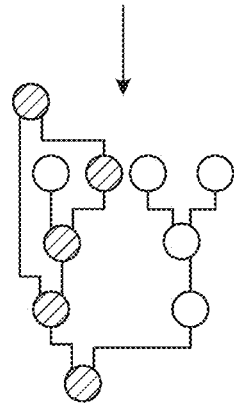
Figure 4A:
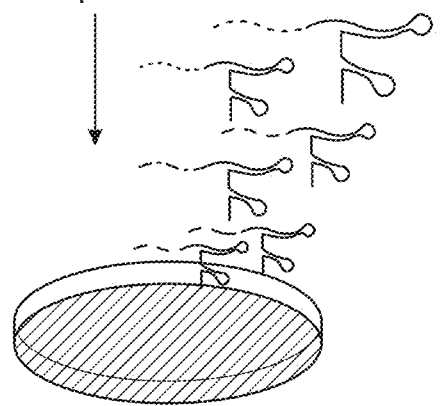
Figure 4B:
Figure 4C:
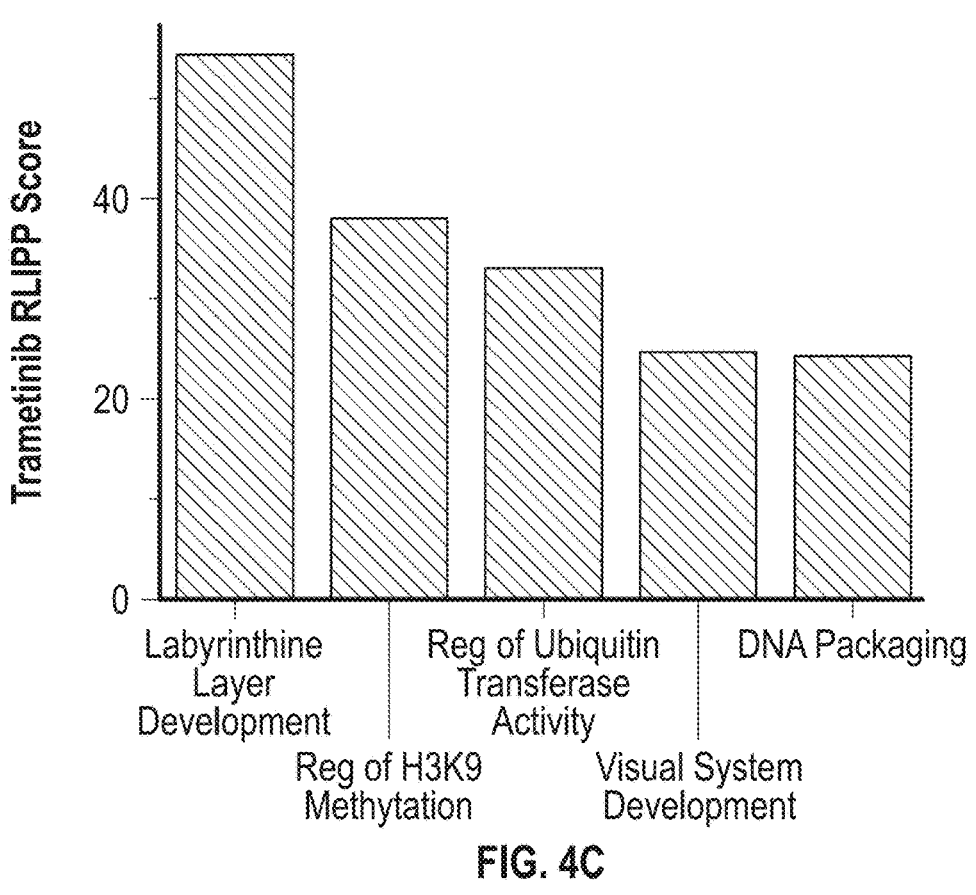
Figure 4D:
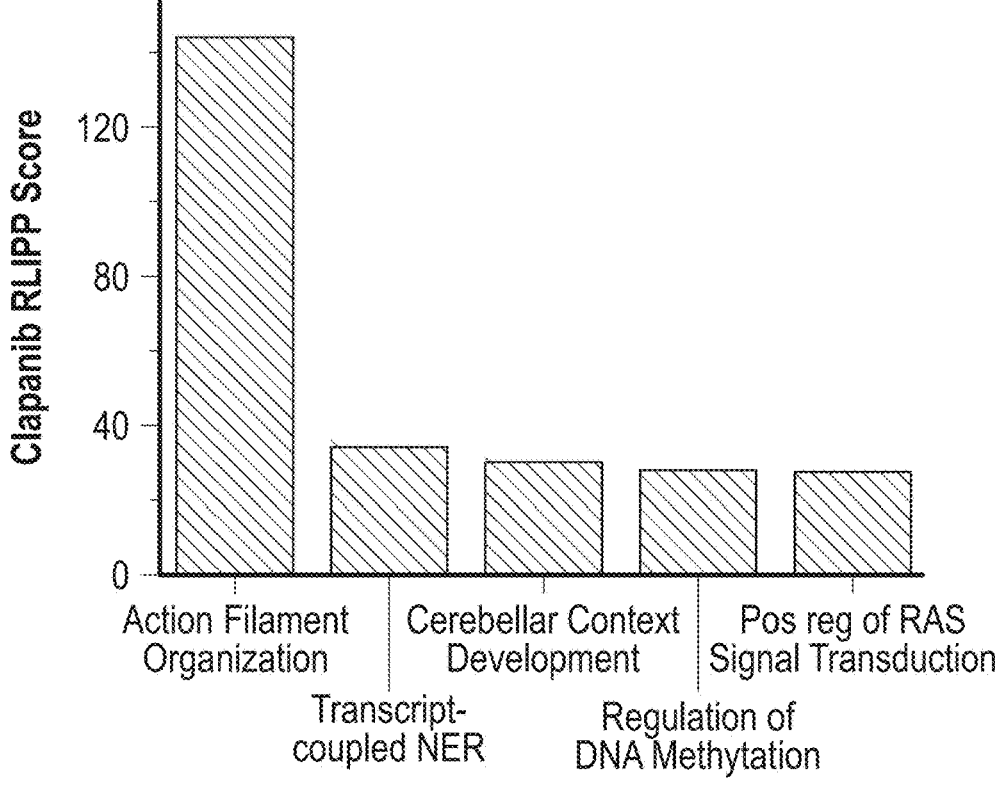
Figure 4E:
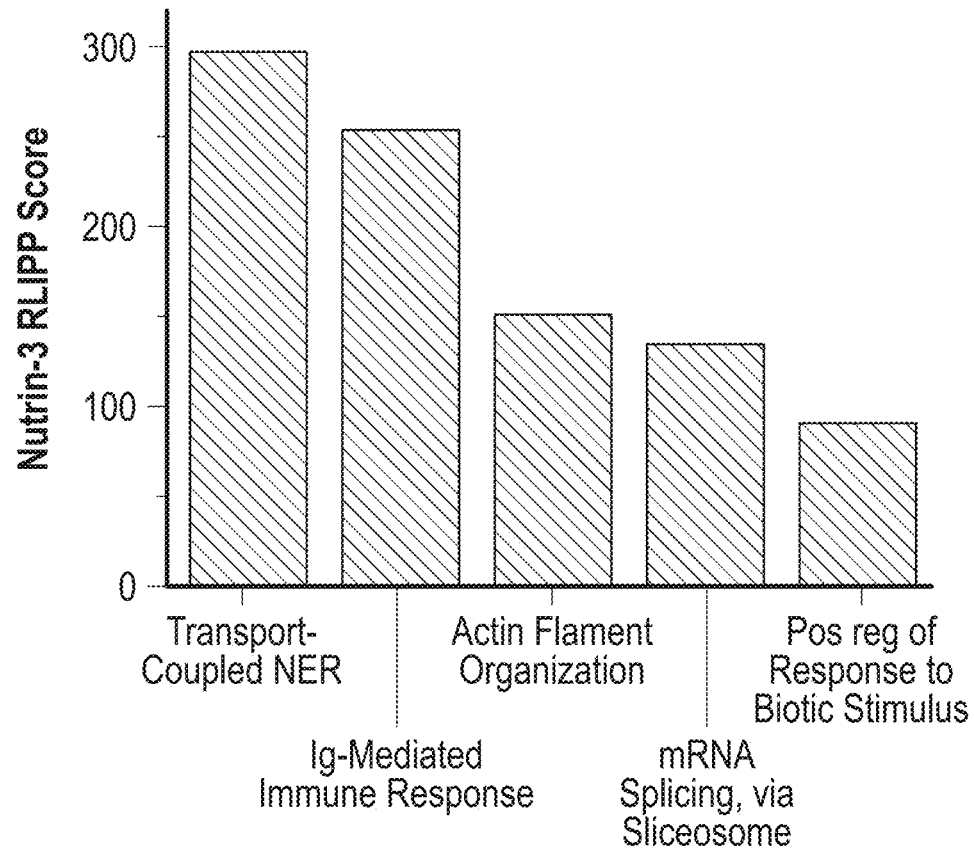
Figure 4H:
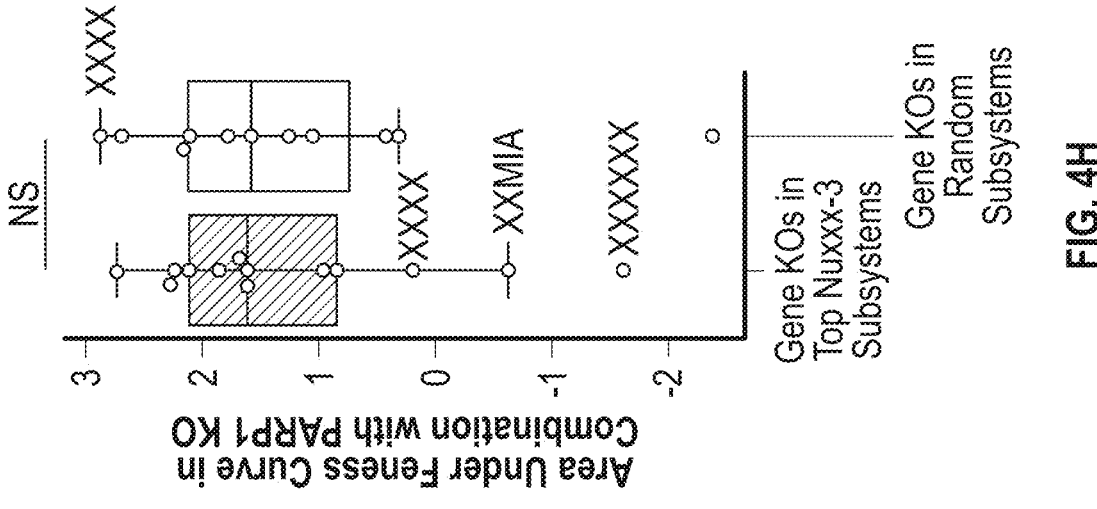
Figure 4G:
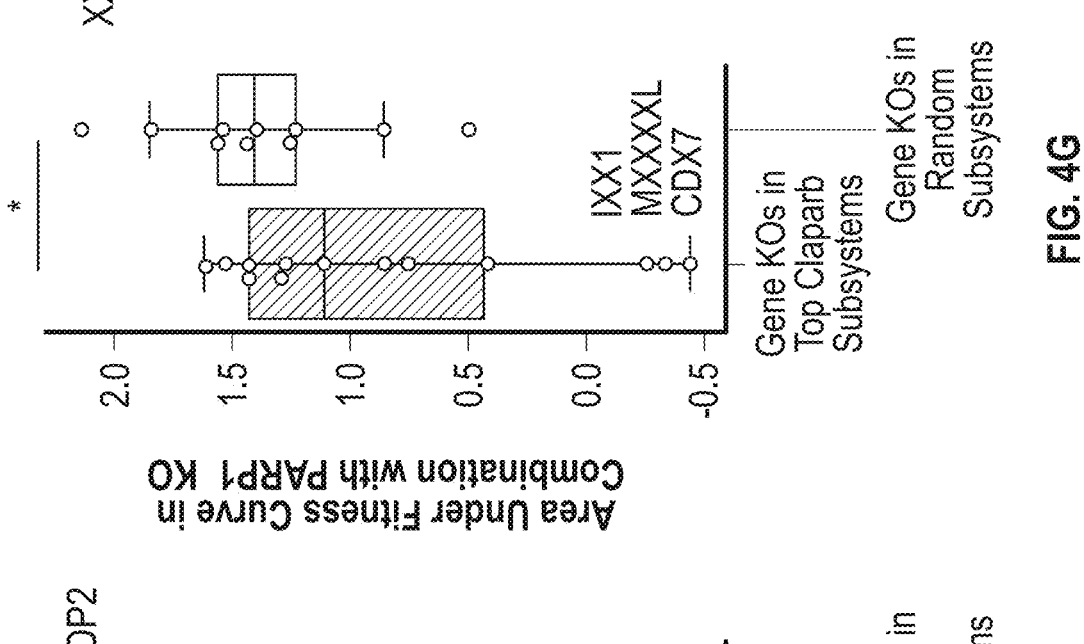
Figure 4F:
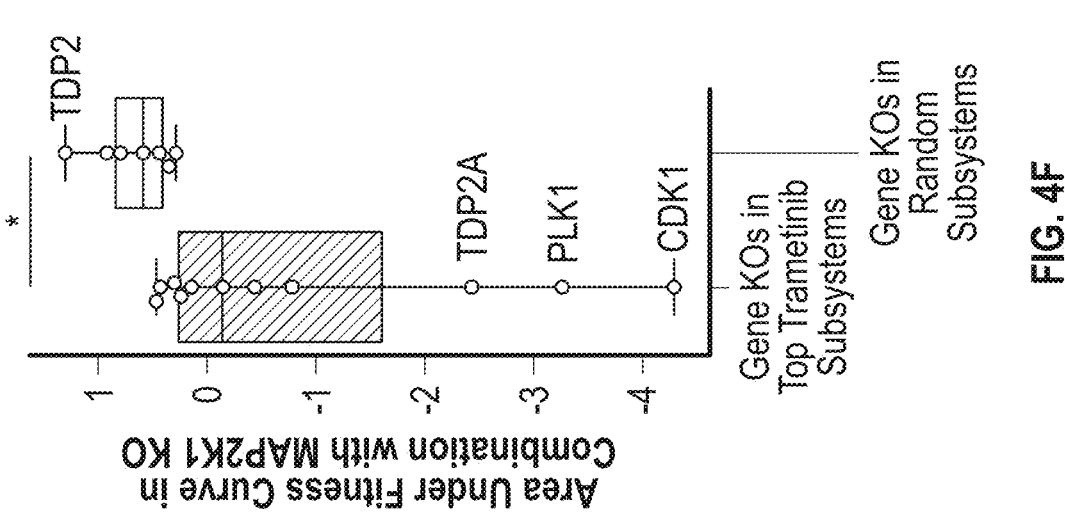
FIG. 4F shows genotype embeddings of each cell line as in (A-D), but with blue-to-red gradient representing response to paclitaxel.

Given the extent of novel drug response pathways, systematical investigation of the indicated mechanisms was performed (FIG. 4A: STAR Methods) focusing on trametinib, a MEK1 inhibitor; olaparib, a PARP1 inhibitor; and nutlin-3, an MDM2 antagonist which stabilizes and activates TP53. CRISPR knockouts of each of the three drug targets (MEK1, PARP1, TP53) were combined with knockouts of each gene in a custom CRISPR/Cas9 library which had broad representation of cancer signaling pathways (MCF7 cells; FIG. 4B). The top five important subsystems in the response to each drug were identified (RLIPP analysis; FIGS. 4C-4E), along with the genes in those subsystems covered by the CRISPR library. Combinatorial disruption of MAPK1 with genes in trametinib subsystems (FIG. 4C) resulted in significantly more cell killing than observed for genes from random unimportant subsystems (FIG. 4F). A similar cell killing effect (FIG. 4G) was observed for combinatorial disruption of PARP1 with genes in olaparib subsystems (FIG. 4D). In contrast, combinatorial disruption of TP53 with genes in nutlin-3 subsystems (FIG. 4E) had effects on cell growth that were not significantly different than random (FIG. 4H). This latter result was expected, as TP53 knockout has the opposite effect of nutlin-3 which leads to TP53 activation. These results, together with the preliminary results from paclitaxel, provide systematic support for the importance of top response pathways identified by DrugCell.

Figure 5A:
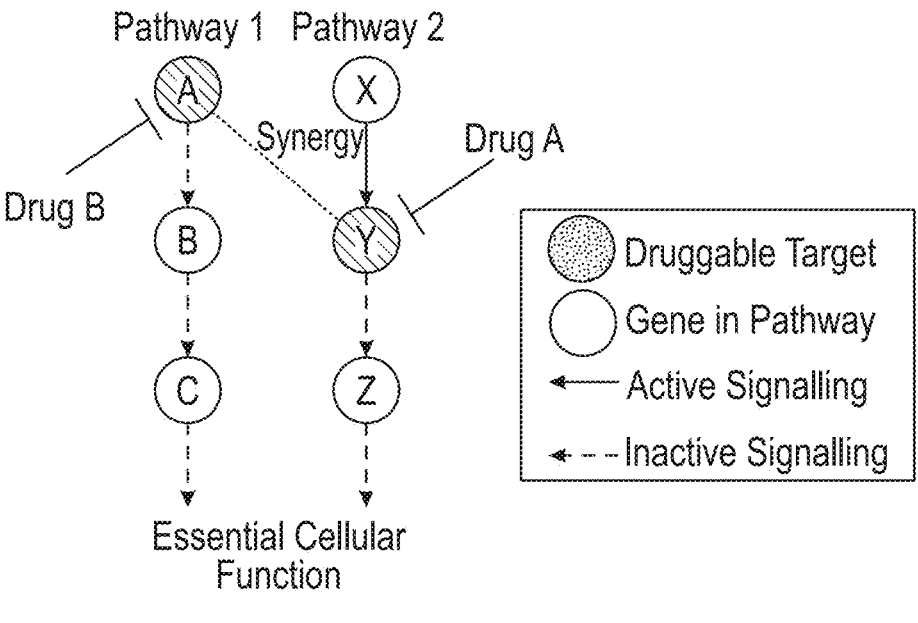
FIGS. 5A-5J show a discovery and validation of synergistic mechanisms.
Figure 5B:
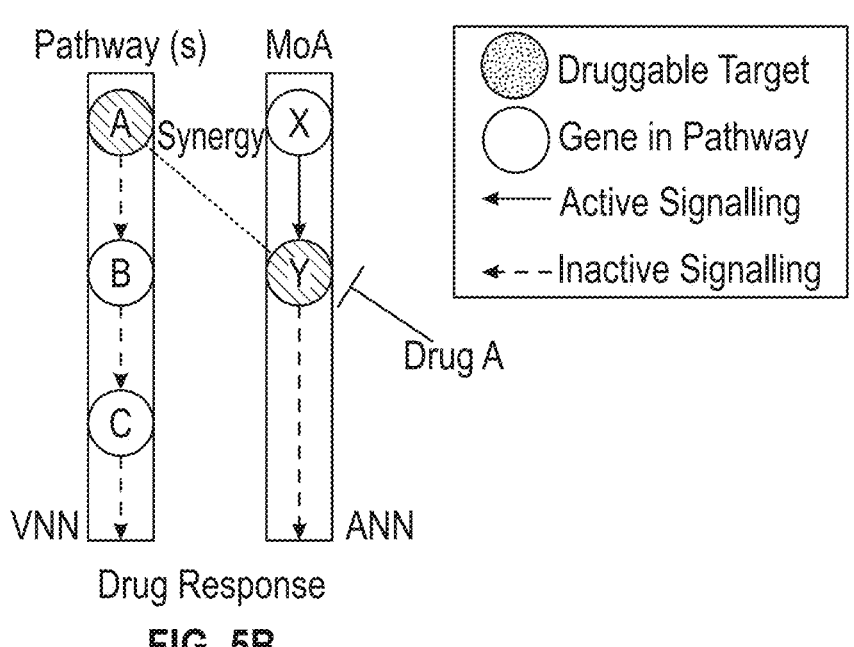

Identified subsystems represent synergistic drug combination opportunities. The parallel pathway inhibition theory of drug synergy (Yeh et al., 2009) holds that two drugs will be synergistic if they inhibit separate pathways that regulate a common essential function (FIG. 5A). The branched architecture of the DrugCell model (FIG. 1A) mirrors this parallel pathway structure, in that the biological activity of a drug is learned by the drug embedding branch, and the parallel pathway(s) are learned by the genotype embedding branch (FIG. 5B). Subsystems important for predicting a drug response may therefore represent synergistic drug combination opportunities. Exactly such parallelism was used to nominate the combination treatments in the above analysis (i.e. 2-DG as synergistic with paclitaxel).

Figure 5C:
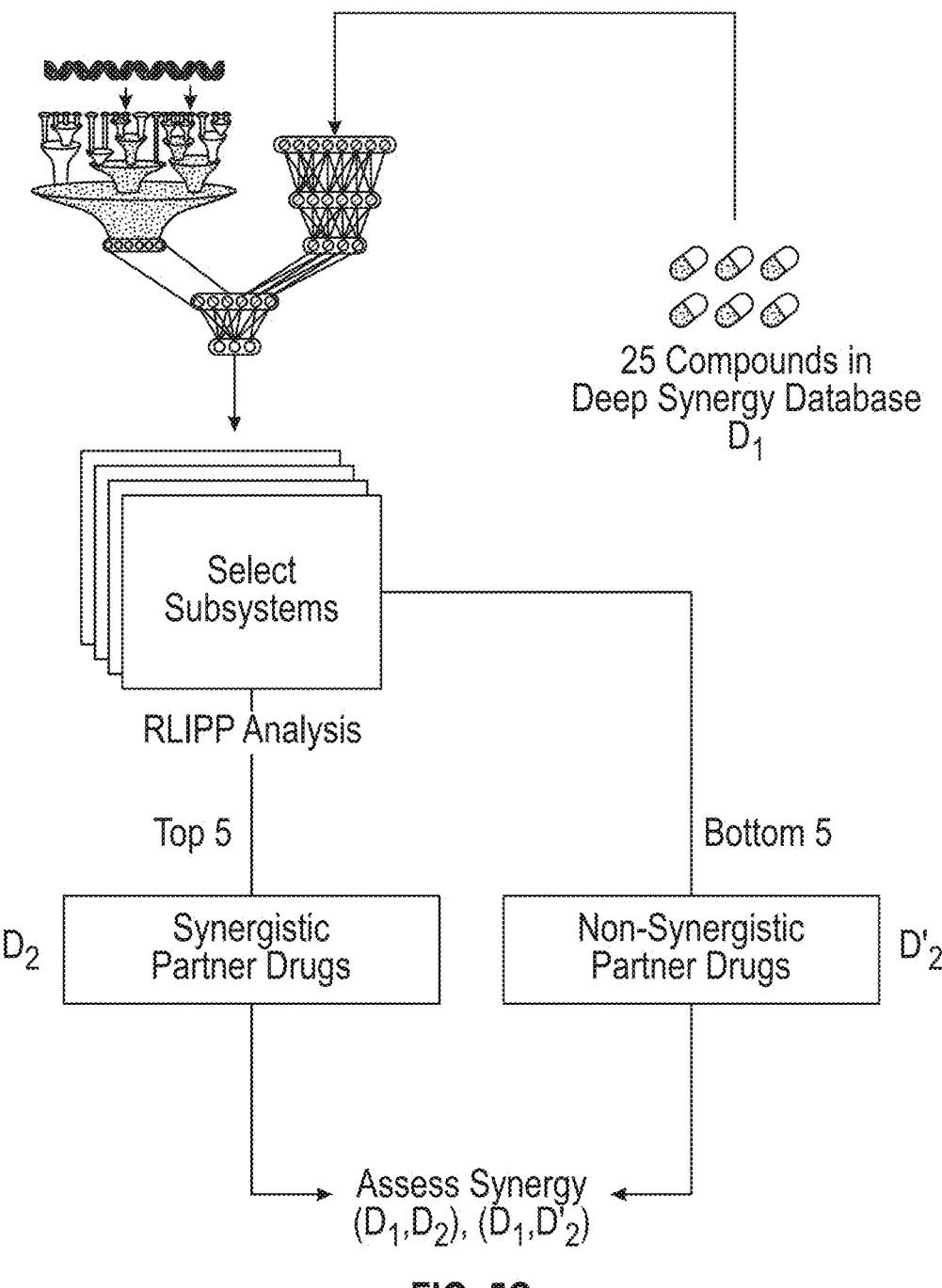
Figure 5D:
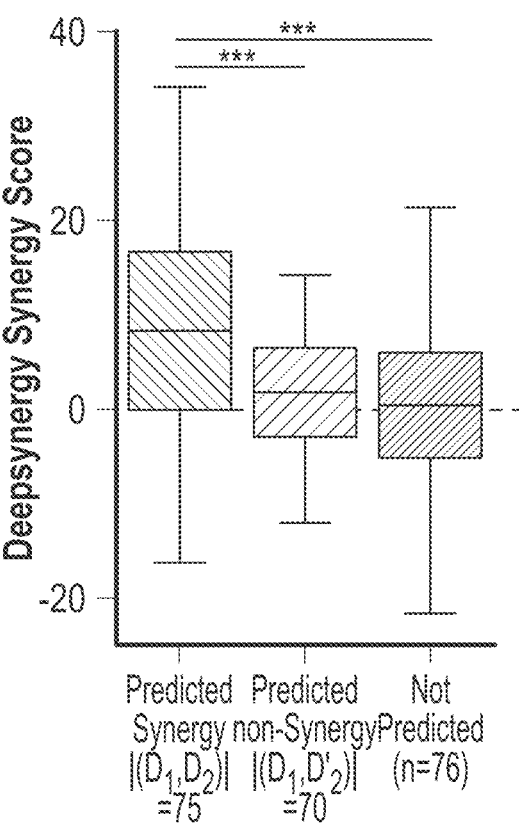

To further explore this concept, RLIPP scores were used to rank subsystems regulating sensitivity to 25 drugs in the DeepSynergy database (Preuer et al., 2018), in which all pairs of 25 drugs had been tested across a panel of 39 cell lines (FIG. 5C). The top 10 and bottom 10 DrugCell subsystems were analyzed for each of these compounds to nominate synergistic and non-synergistic drug combinations. It was observed that drug combinations nominated by DrugCell were strongly and significantly enriched for synergistic cell killing outcomes, in contrast to combinations predicted to be non-synergistic, or random combinations (FIG. 5D).

Figure 5E:
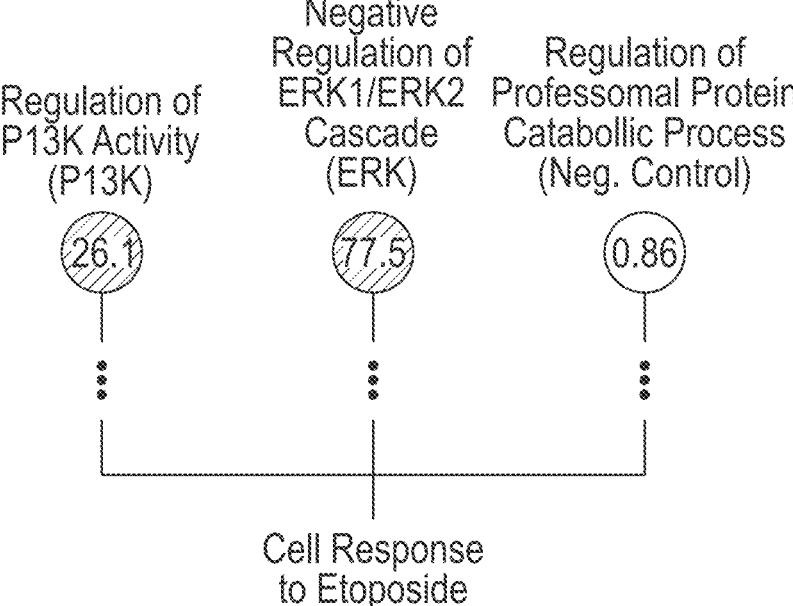
Figures 5F, 5G:
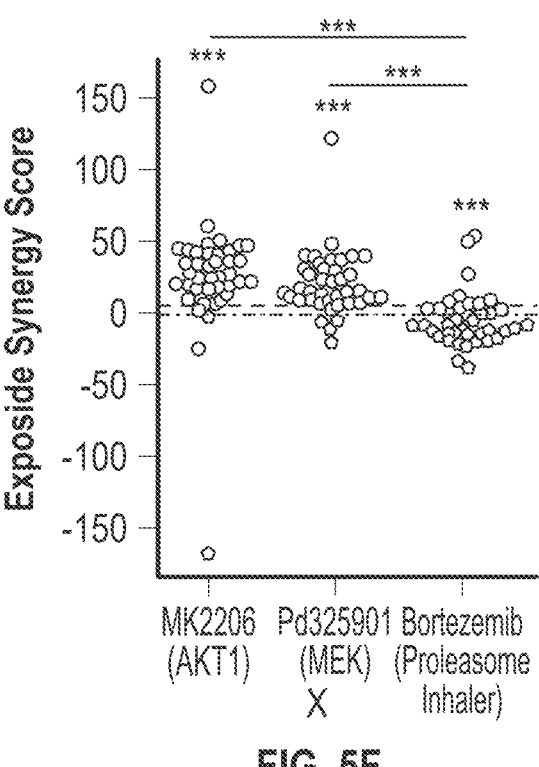

One such example was etoposide, a topoisomerase inhibitor that leads to DNA damage. Among the top etoposide subsystems were the major kinase signaling pathways PI3K-AKT (Regulation of PI3K activity, PI3K; FIG. 5E) and RAF-MEK-ERK (Negative regulation of ERK1/ERK2 cascade, ERK; FIG. 5E). Indeed, etoposide synergized strongly with AKT and MEK inhibition across the majority of cell lines tested in DeepSynergy (FIG. 5F). The observed synergy was further observed by deleting the target of etoposide, TOP2, using CRISPR/Cas9 gene editing in A549 cells, either alone or in combination with core genes in PI3K-AKT signaling (PIK3CA) or RAF-MEK-ERK signaling (MAP2K1). Deletion of TOP2 with either PIK3CA or MAP2K1 demonstrated significant loss of cell viability compared to single gene knockout (FIG. 5G). APC, whose subsystem (beta-catenin destruction complex) was not identified by RLIPP, did not show this same pattern (FIG. 5G). Similarly, etoposide did not synergize with the proteasome inhibitor bortezomib (FIG. 5F), consistent with the proteasome subsystem not being identified by DrugCell (Figure 5E).

Figure 5H:
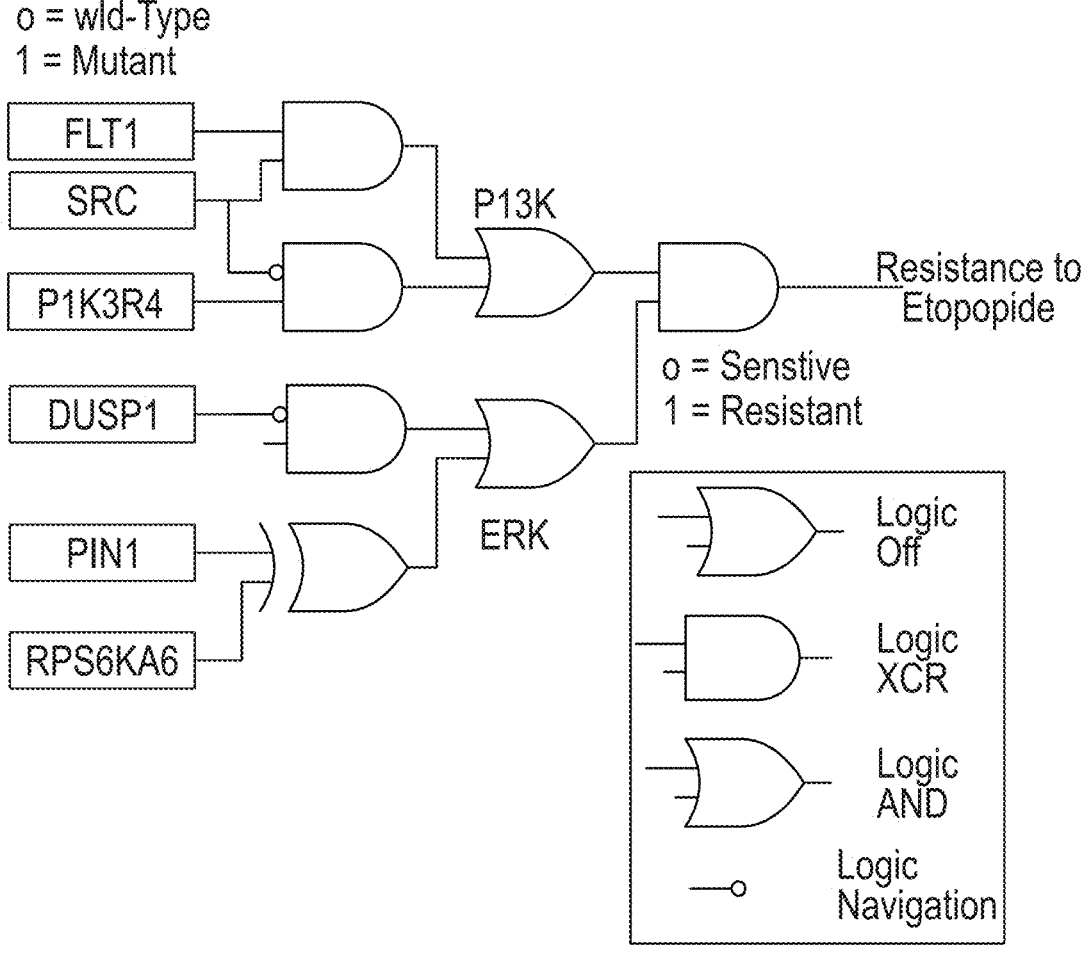
Figure 5I:
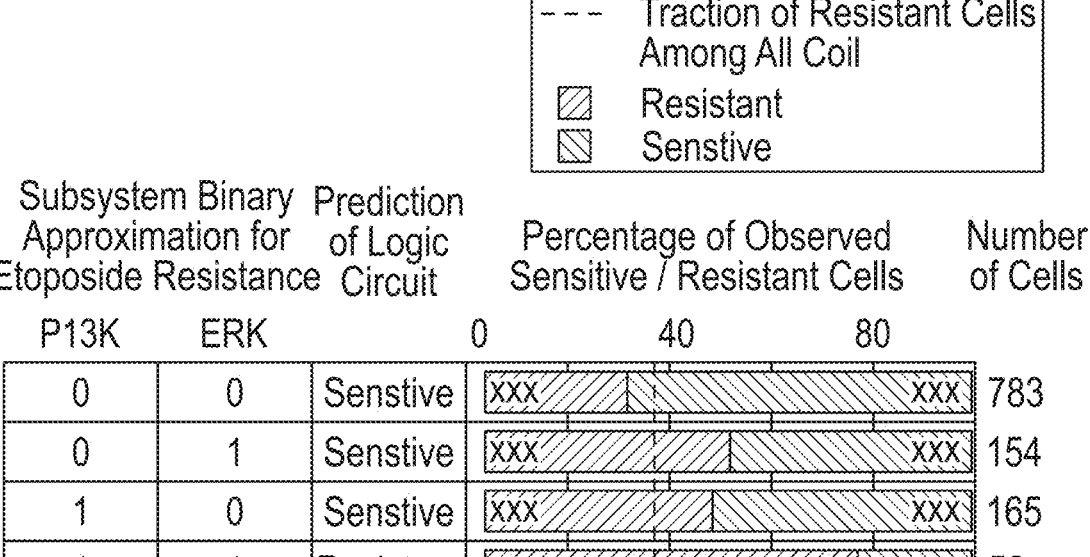
Figure 5J:
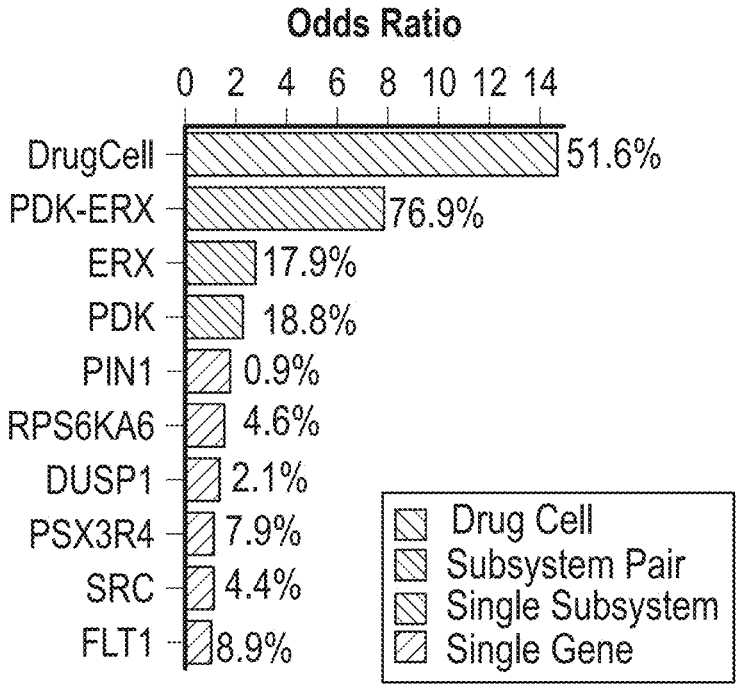

Further inspection suggested that the relationship between PI3K signaling, ERK signaling, and etoposide sensitivity captured by DrugCell could be roughly approximated by a logic function integrating the mutational status of six genes (FIGS. 5H and 5I; STAR Methods). Among these. FLT1 (Das et al., 2005) and PIN1 (Mathur et al., 2011) had previously been shown to regulate etoposide response, whereas DUSP1, PIK3R4, SRC, and RPS6KA6 had not. Considered individually, any one of these genes was mutated rarely in cancer cell lines, with limited power to predict etoposide sensitivity versus resistance (mutation frequencies 0.9-8.9%; odds ratios<2; FIG. 5J). Considered as an integrated circuit, however, these gene mutations converge on PI3K or ERK subsystems to create a powerful network-based biomarker of drug response (odds ratio 7.8; FIG. 5J). It should be noted that these two pathways represent only a portion of the full DrugCell model, which predicts etoposide sensitivity with an odds ratio of 14.3.

Figure 6A:
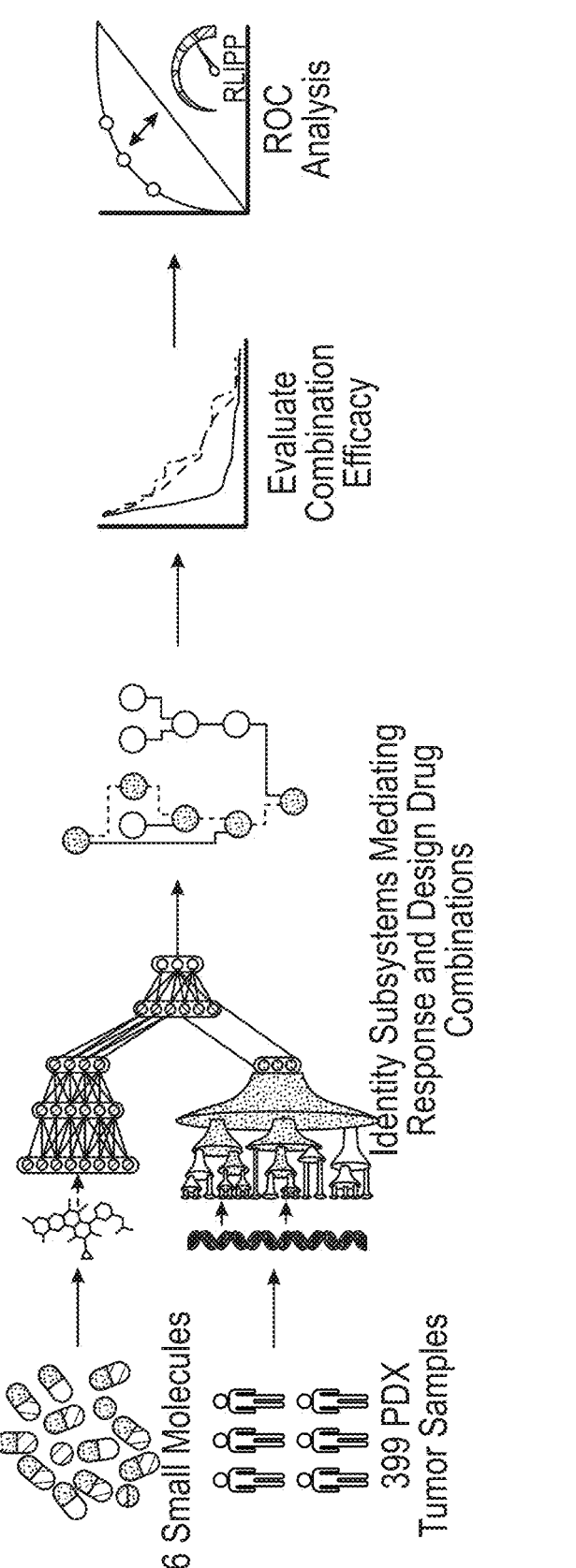
FIGS. 6A-6E show guiding combination therapy in patient-derived xenograft tumors.
Figure 6B:
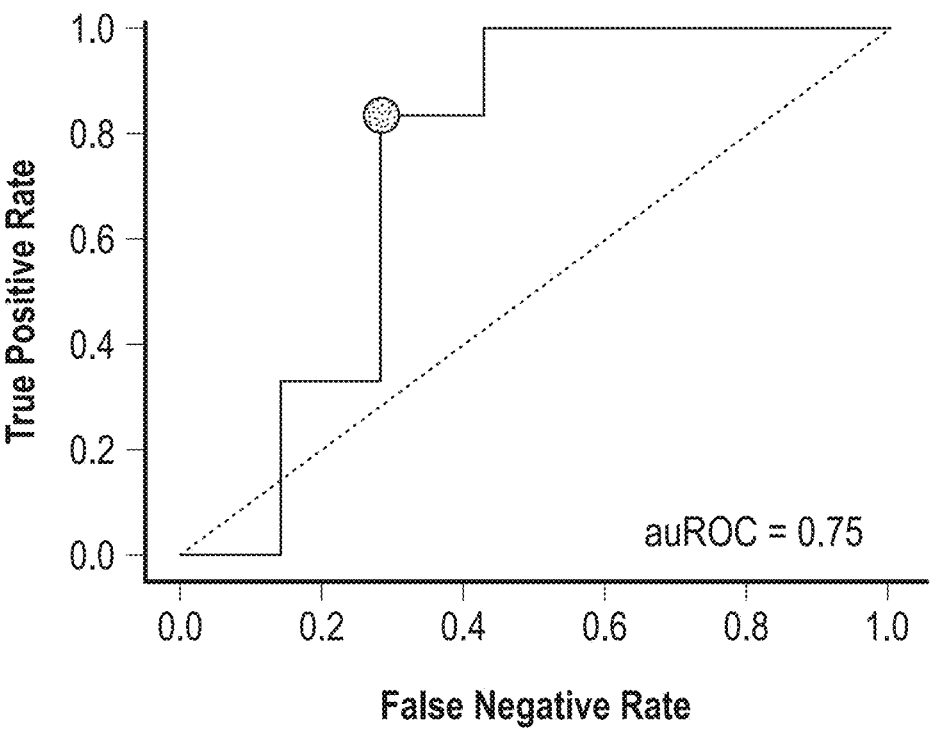
Figure 6C:
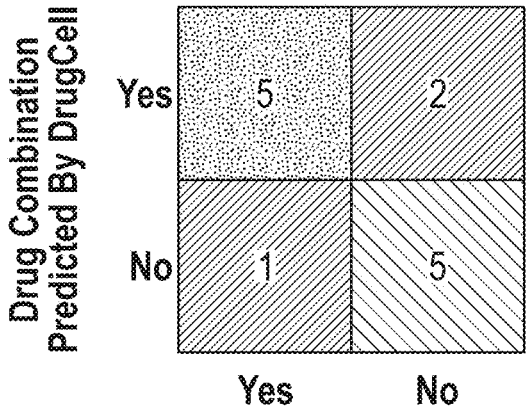

DrugCell improves progression free survival of patient-derived xenograft models. Techniques described herein may be applicable beyond cell lines, and may be used to predict and interpret drug responses in the in-vivo setting of patient-derived xenograft models (PDX; FIG. 6A, STAR Methods). To do so, the PDX Encyclopedia (Gao et al . . . 2015) was accessed, in which 399 PDX tumors of varying tissue types had been screened against a total of 40 different monotherapies and 27 combination therapies. The genotypes of each PDX had also been established (Gao et al., 2015), which were provided to DrugCell to make response predictions to each monotherapy. A PDX tumor was considered to be sensitive to a therapy (DrugCell (+)) if its predicted AUC was beneath the median predicted for all PDX-drug pairs; otherwise this tumor was labeled as insensitive (DrugCell (−)). DrugCell (+) tumors demonstrated significantly higher progression free survival (PFS) than DrugCell (−) tumors (2.19 vs. 1.58 months, p=9.4×10$^{-10}$, log-rank test). However, given the overall insensitivity of these PDX tumors to monotherapy, corresponding to the short observed PFS observed for both DrugCell classes, an analysis was performed to evaluate how well DrugCell is able to suggest effective drug combinations. RLIPP scoring was used to rank subsystems by importance in mediating drug responses to six primary drugs, filtering this list to those which contained secondary drug targets. The observed PFS of each of these (primary, secondary) combinations was used to estimate the prediction sensitivity and specificity along a Receiver Operating Characteristic curve (ROC; FIG. 6A, STAR Methods). It was found that DrugCell was able to accurately identify subsystems that correspond to effective drug combinations in PDX tumors (auROC=0.75; FIG. 6B) with relatively few false positives and negatives (FIG. 6C).

Figure 6D:
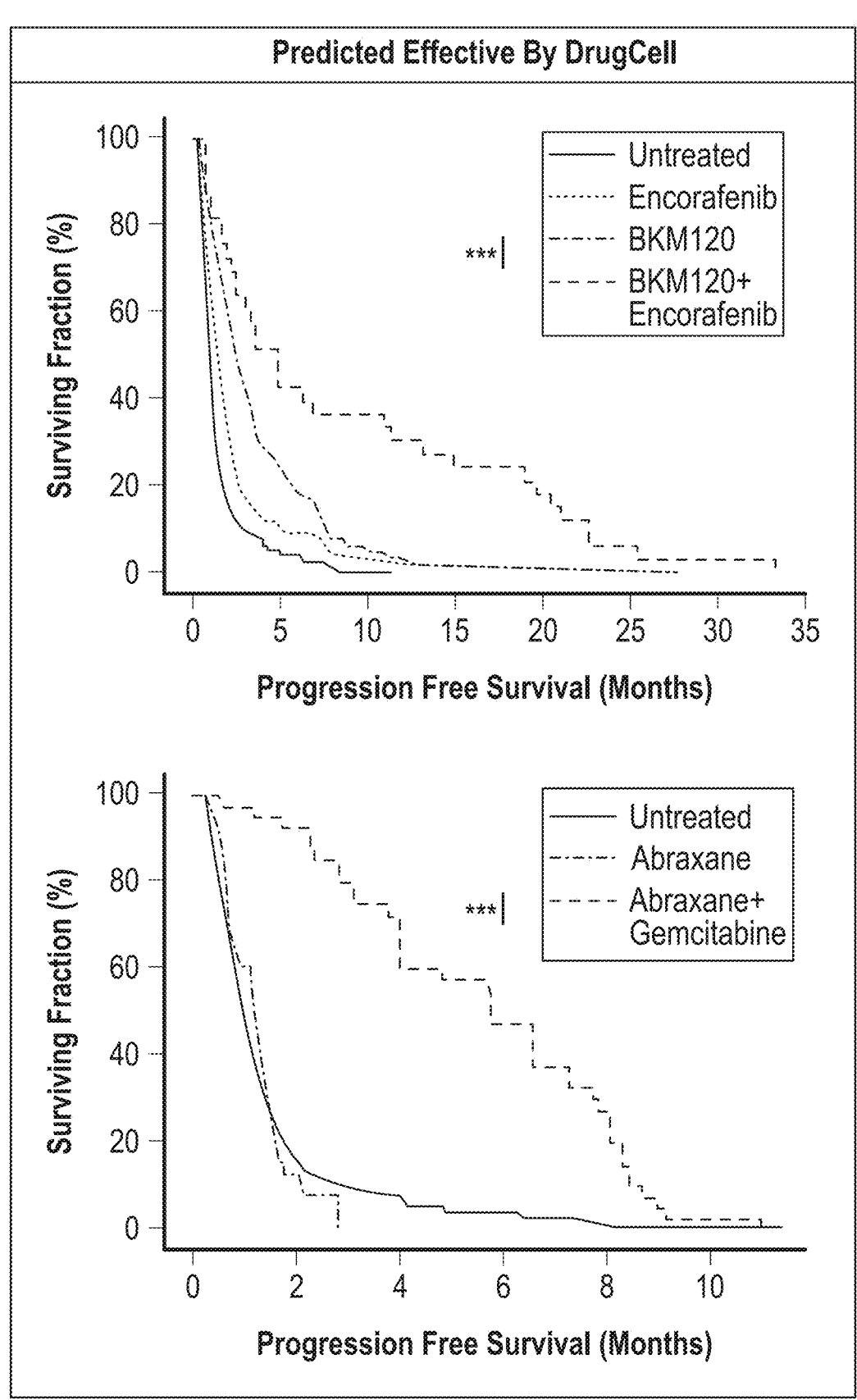
Figure 6E:
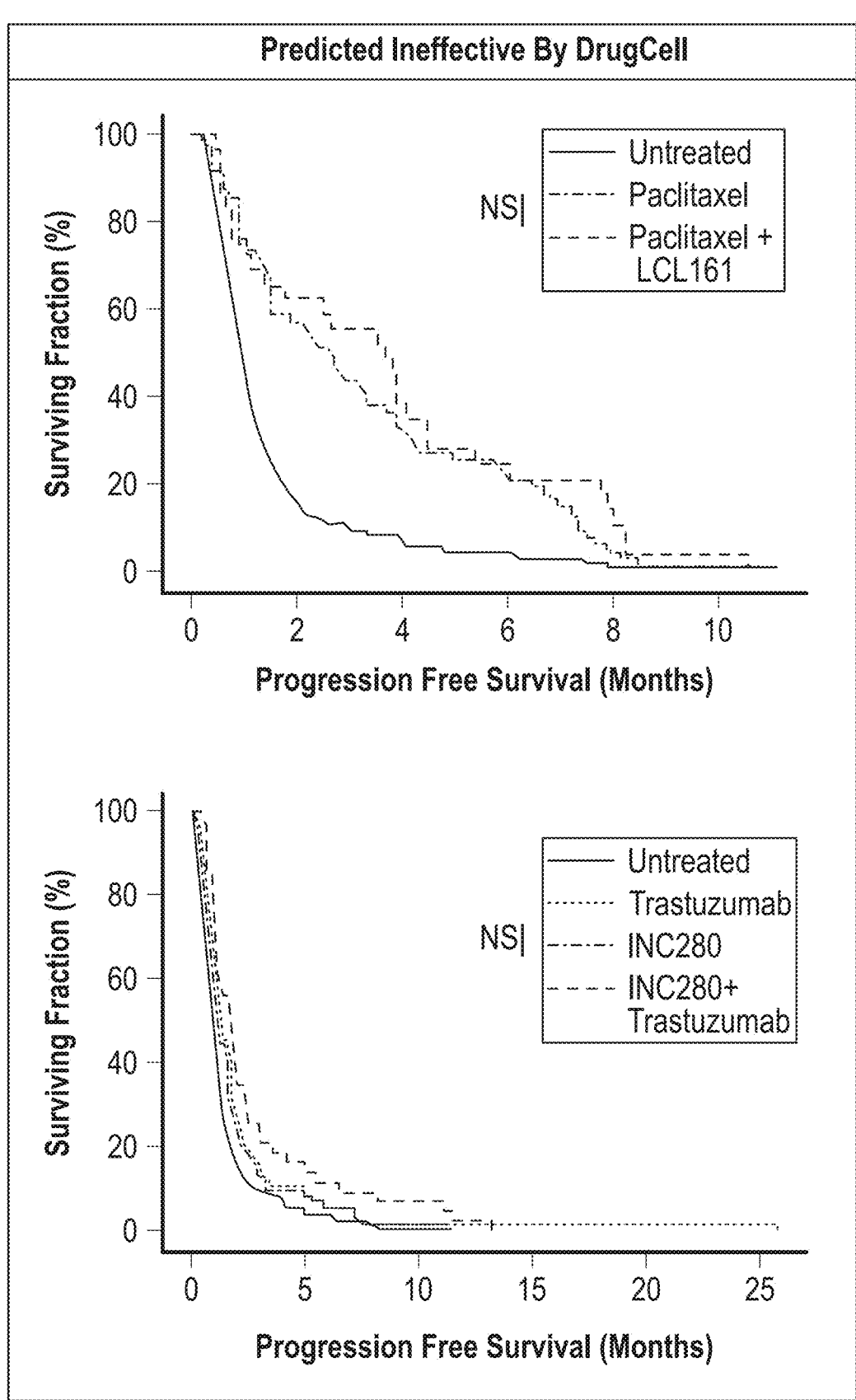

For example, DrugCell analysis of BKM-120, a PI3K inhibitor, identified Negative regulation of ERK1-ERK2 cascade as an important subsystem for BKM-120 response, suggesting a combination of PI3K+MAPK pathway inhibitors (BKM-120+encorafenib). This combination significantly increased PFS across the PDX panel compared to monotherapy (FIG. 6D). Similarly, DrugCell identified DNA damage response, signal transduction by p53 class mediator resulting in cell cycle arrest as an important subsystem for abraxane response, suggesting combination chemotherapy with an agent inducing DNA damage and cell-cycle arrest (abraxane+gemcitabine). This combination similarly significantly improved PFS (FIG. 6D). For the combinations that were not prioritized by DrugCell (not in top 20% of subsystems by RLIPP), these combinations indeed failed to significantly improve progression free survival (FIGS. 6C and 6E). These results suggested that DrugCell has utility in guiding design of combination therapies in patient tumors.

Figure 7A:
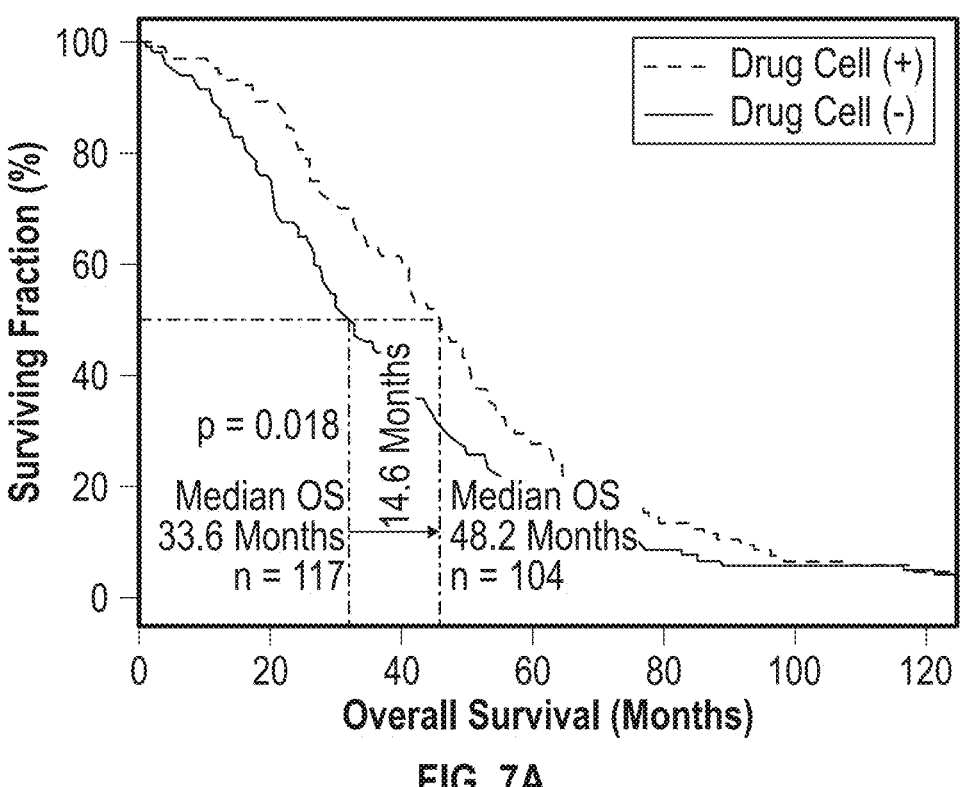
FIGS. 7A-7E show guiding CDK4/6 and mTOR inhibitor therapy in ER-positive breast cancer patients.

DrugCell predicts the response of ER-positive metastatic breast cancer patients to m'TOR and CDK4/6 inhibitors. Lastly, an analysis was conducted to determine whether DrugCell could be used clinically to stratify cancer patients into responsive and non-responsive patient populations. Aggregated clinical trial data was obtained and analyzed (Smyth et al., 2020) from 221 estrogen receptor (ER)-positive metastatic breast cancer patients who had undergone multiple rounds of therapy including an estrogen receptor antagonist (fulvestrant) in addition to treatment with an mTOR inhibitor (everolimus) or CDK4/6 inhibitor (ribociclib). For this analysis (STAR methods), patient response to either mTOR or CDK4/6 inhibition was predicted using a pre-trained DrugCell model. A patient was considered to be DrugCell (+) if they were predicted sensitive to either therapy and DrugCell (−) if they were predicted to be insensitive to both therapies. DrugCell (+) patients had significantly longer overall survival than DrugCell (−) patients (48.2 vs. 33.6 months, p=0.018; FIG. 7A).

Figure 7B:
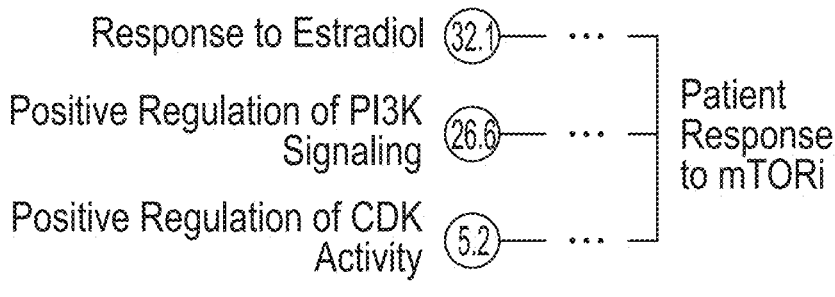
Figure 7C:
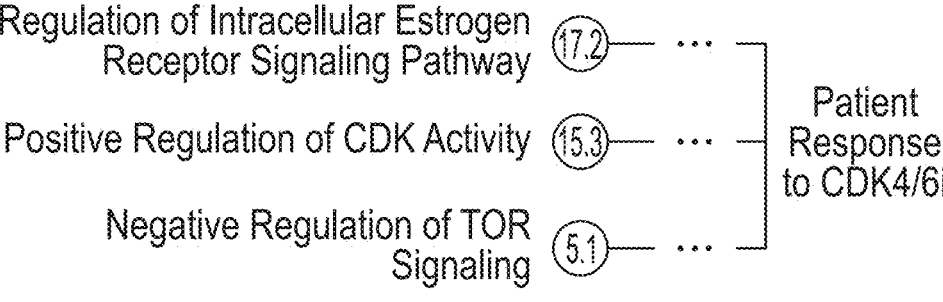

Next, the mechanisms underlying the differential sensitivity between DrugCell (+) and DrugCell (−) patients were interrogated by performing an RLIPP analysis for both the mTOR and CDK4/6 inhibitors. Notably, it was found that both drug responses were modulated by estrogen receptor-related subsystems (FIGS. 7B and 7C), consistent with their use in ER-positive breast cancer (Hare and Harvey, 2017; Pernas et al., 2018). It was also found that the major mechanisms of action of both drugs were among the top pathways, with PI3K signaling being especially important for response to mTOR inhibitors, and CDK activity being important CDK4/6 inhibitor activity (FIGS. 7B and 7C). Interestingly, TOR signaling was also identified for CDK4/6 inhibitors (FIG. 7B), and CDK activity was identified for mTOR inhibitors (FIG. 7C), suggesting that these drugs could be an effective combination therapy, a finding supported by recent preclinical studies (Michaloglou et al., 2018; Occhipinti et al., 2020).

Figure 7D:
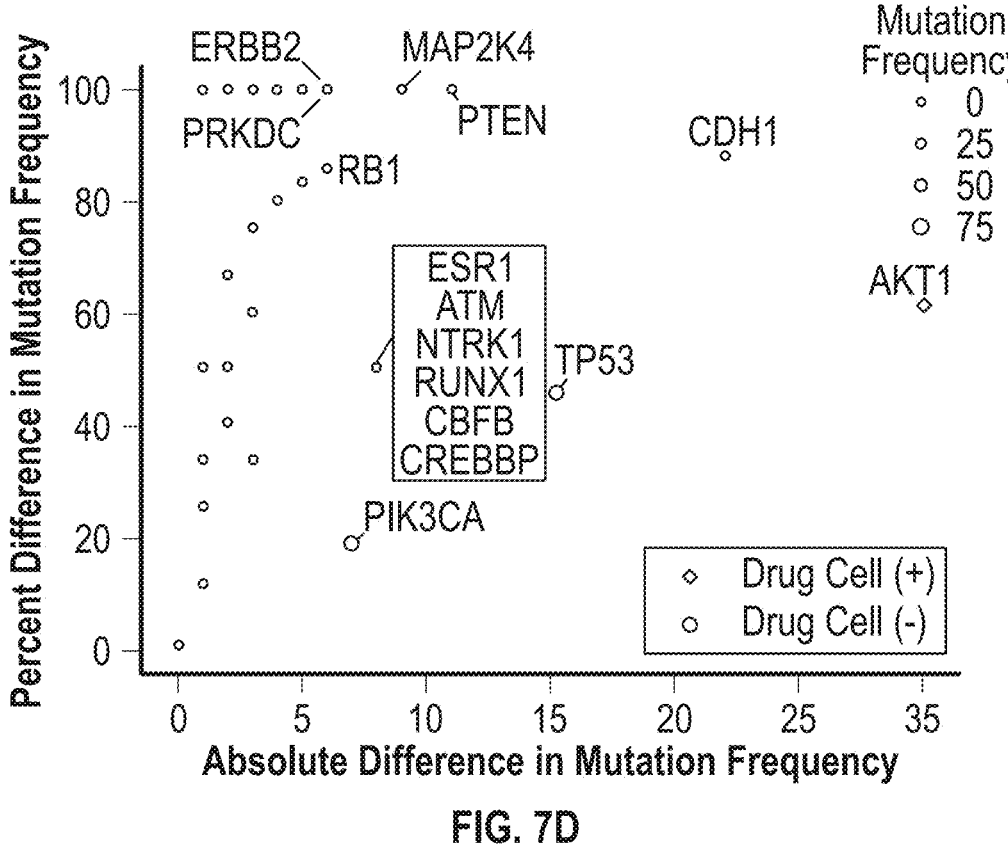
Figure 7E:
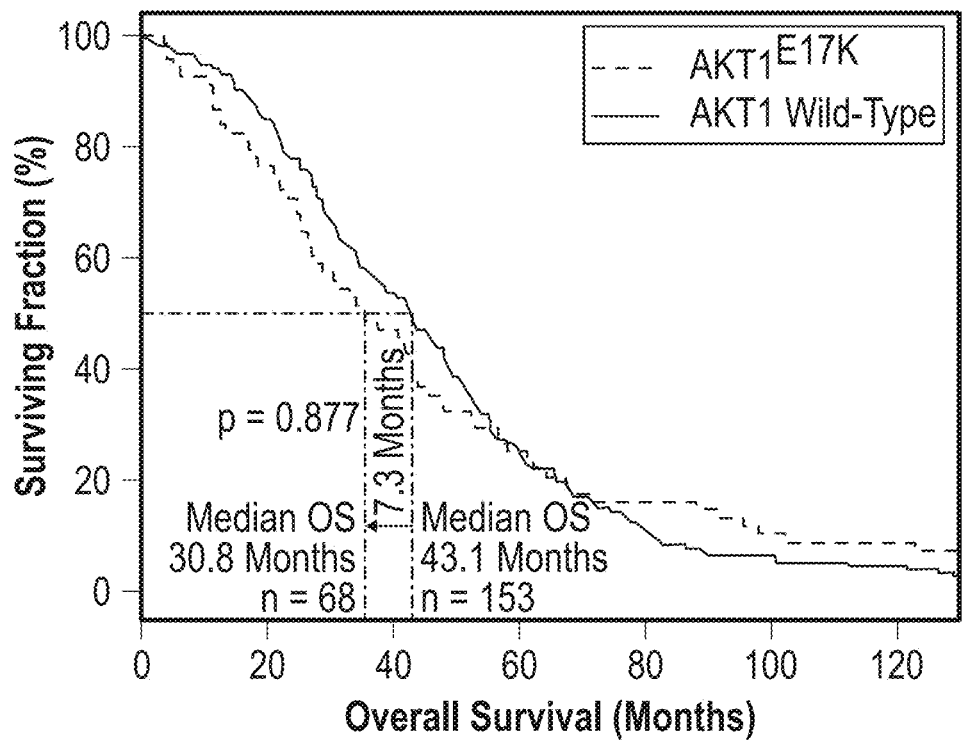

With respect to specific genetic alterations, it was determined that DrugCell (+) patients were much more likely to harbor AKT1 mutations than DrugCell (−) patients (FIG. 7D). In contrast, DrugCell (−) patients had mutations in genes previously associated with drug resistance including ESR1 (Reinert et al., 2017), RB1 (Condorelli et al., 2018), and PTEN (Costa et al., 2020) (FIG. 7D), suggesting that patients were stratified based on a complex pattern of mutations leading to therapy resistance. Strikingly. AKT1 mutation status alone was not predictive of therapeutic response, with AKT1-mutant patients actually trending towards shorter overall survival (35.8 vs. 43.1 months), although this difference was not statistically significant (FIG. 7E). This analysis illustrates how DrugCell can be used to effectively guide clinical treatment decisions with significantly greater precision and insight than single gene marker studies.

Discussion

As described in greater detail above and below, an interpretable deep learning model of the structure and function of a human cancer cell in response to treatment is disclosed. This work advances predictive modeling towards a systematic representation of the biological mechanisms underlying a drug response, a critical direction for precision medicine. Following a model prediction, access to a mechanistic interpretation engages the experimentalist or clinician in reasoning about biological function. For example, analysis of DrugCell's model of etoposide identified a small set of subsystems important for the cellular response and for which targeted drugs were available (FIG. 5). This analysis motivated us to perform subsequent experiments to target both genetically and pharmacologically topoisomerase II with either MAPK or PI3K pathways; both of these combinations showed significant synergistic effects. Such engagement of human reasoning and follow-up experimentation helps greatly to increase accountability and trust in the predictions of a machine learning model. In contrast, conventional black-box predictive modeling yields only a model output—the drug response-without further information by which to build trust in the process.

DrugCell is a flexible model that is amenable to both automated and semi-automated combinatorial drug design. First the importance of each cellular subsystem is scored by DrugCell during a response to monotherapy. These important subsystems are then annotated with second points of intervention, such as PI3K or ERK pathways in the response to etoposide (FIGS. 5E-G). To follow up on this analysis, drug combinations can be selected automatically based on the druggable targets present in top DrugCell subsystems. Alternatively, if DrugCell is being used in a clinical context, its recommendations can be provided to physician-scientists (e.g. a molecular tumor board) who consider the recommended combinations in light of other biological knowledge not explicitly used in modeling, such as potential toxicities and specific information about the case. After careful consideration of all relevant information, the ultimate treatment decision remains in the hands of the physician and patient. Such need for human accountability is not unique to drug response prediction but is a central tenet of high-stakes applications of machine learning (Rudin, 2019).

Notably, previous models trained on monotherapy responses (Ammad-ud-din et al., 2017; Cortés-Ciriano et al., 2016; Iorio et al., 2016; Zhang et al., 2015) have not attempted to suggest combination therapies. Rather, drug combinations have been predicted using models of synergy trained directly on data from pairwise drug treatments (Preuer et al., 2018). This brute-force approach faces the challenge of scalability, given the combinatorial number of pairwise and higher order drug combinations necessary for training.

If the favorable performance observed in PDX samples (FIG. 6) and ER-positive breast cancer patients (FIG. 7) continues in further clinical studies, DrugCell and its successors have the potential to substantially expand the set of clinically meaningful mutations. DrugCell translates the mutational status of approximately 3,000 genes into treatment recommendations. RLIPP analysis suggests that many of them are—1,467 of the 2,086 subsystems are assigned relatively high importance (RLIPP>10) for at least one drug, collectively covering 2,855 genes. This breadth of information contrasts with the fewer genes included in current cancer mutation panels such as MSK-IMPACT or FoundationOne CDx (468 and 324 genes, respectively), which were designed to be queried manually by a physician (Cheng et al., 2015; Harris, 2017). Moreover, since the clinical implications of the majority of cancer mutations are not currently well-understood, there is little consensus on what genes should be included in these pan-cancer mutation panels (Nguyen and Gocke, 2017) or on how physicians should act on the results. An increase in the number of clinically meaningful cancer mutations, facilitated by interpretable machine learning models such as DrugCell, could further motivate the case for complete genomic sequencing of cancer patients (Katsanis and Katsanis, 2013; Kuenzi and Ideker, 2020).

Future work may also elect to integrate mutations with additional levels of molecular information such as epigenetic states, gene expression or microenvironmental influences. This integration could be accomplished by preprocessing multiple layers of information to derive a profile of gene scores for each cell line or tumor, which would then be input to DrugCell. Extra levels of information could also be integrated by adding new visible or conventional neural network branches alongside existing ones. Alternatively, the effects of specific mutations on gene functions could be incorporated by a metric such as the Combined Annotation-Dependent Depletion score (Rentzsch et al., 2019) or by including gene structural domains as an additional layer of the hierarchy.

Another opportunity is to structure the DrugCell system hierarchy from 'omics data rather than literature curation (GO), as has previously been done in budding yeast (Kramer et al., 2014; Ma et al., 2018). A data-driven, rather than literature-curated, hierarchy has the potential to incorporate new gene-subsystem associations as well as entirely new subsystems into the model. It also has the potential to revise and tailor subsystem definitions in GO, which are generic, to their particular contexts relevant to cancer. For instance, it was found that in its current form DrugCell contains a number of subsystems that have misleading labels based on GO naming conventions. For example, Labyrinthine development was among the top subsystems for trametinib, which was initially puzzling but upon further inspection corresponds to MAPK cascade genes with well-known involvement in cancer proliferation (e.g. MAP2K1, MAPK1, GRB2, FGFR2). Incorporating data-driven hierarchies into DrugCell provides a route to relabel such subsystems and revise their specific gene contents. Finally, given that DrugCell inputs a full drug structure, it can potentially be used to design compounds de novo. Leveraging advancements in reinforcement learning for drug design (Zhavoronkov et al., 2019), it may then be possible to design compounds for maximal efficacy against any given genomic background.

Experimental Model and Subject Details

Cell culture and reagents. A549, A427, and MCF7 cells were retrieved from the American Type Culture Collection (ATCC) and cultured in DMEM: 10% FBS or EMEM+10% FBS according to ATCC recommendations. All cell lines tested negative for *mycoplasma* contamination and were authenticated by short tandem repeat (STR) analysis. Paclitaxel (Selleckchem) was dissolved in DMSO (10 mM) and diluted in media for use. 2-deoxy-d-glucose (Selleckchem) was dissolved in media (100 mM), filtered, and further diluted in media for use.

Method Details

Defining a hierarchy of genes and cellular subsystems. To computationally represent cancer genotypes, the top 15% most frequently mutated genes in human cancers were selected according to the Cancer Cell Line Encyclopedia (CCLE) (Barretina et al., 2012) among genes annotated to Gene Ontology (GO) terms (Ashburner et al., 2000). This procedure yielded 3,008 genes, henceforth called 'DrugCell genes', which were used in model construction. These genes were organized into a hierarchy of nested gene sets, representing cellular subsystems at different scales, based on terms extracted from the GO Biological Process hierarchy. Terms were retained from GO if they had at least 10 DrugCell genes and were distinct from all child terms, defined as having at least 30 DrugCell genes more than any child (both part_of and is_a hierarchical term relations were considered). Every other term was removed from the hierarchy, and instead its children were assigned directly to its parents to keep the hierarchy connected. To further reduce model complexity, the hierarchy was restricted to a maximal depth of five subsystems by removing all subsystems more than five parent-child relations above the bottom layer subsystems of the hierarchy (subsystems without any children). The resulting hierarchy, composed of 2,086 subsystems, defined the branch of DrugCell for embedding of genotype (left branch in FIG. 1A, also called the VNN; FIG. 1B).

Figure 14B:
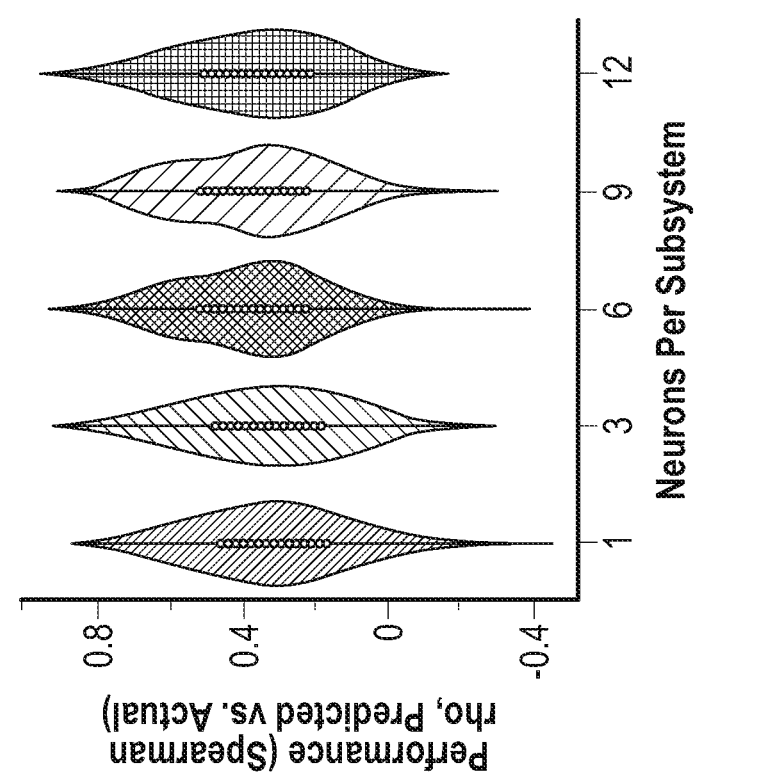
FIGS. 14A-14B show comparison of previously published drug responses with this study, Related to STAR Methods.
Figure 14A:
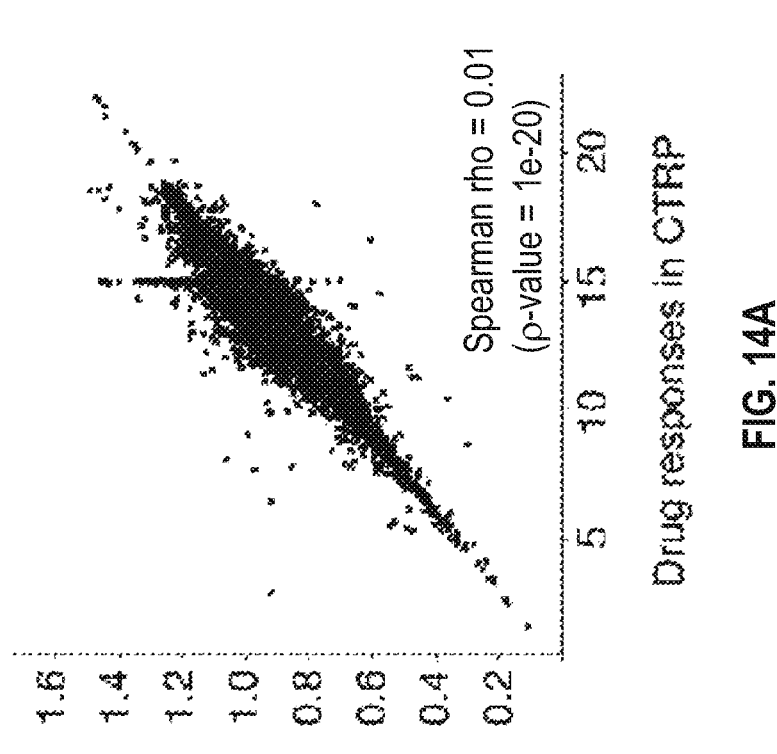

Pharmacogenomics data processing and Morgan fingerprint encoding. To obtain a sufficiently large pharmacogenomic dataset for model training, raw drug sensitivity data were retrieved from the Genomics of Drug Sensitivity in Cancer database (GDSC) and the Cancer Therapeutics Response Portal v2 (CTRP) (Seashore-Ludlow et al., 2015: Yang et al., 2013). These data covered a total of 509,294 (cell line, drug) pairs. Among these data. 24,923 pairs redundantly measured in the two repositories were left intact in the training dataset, as such replicates can be beneficial to reduce model over-fitting. Luminescence values were background corrected (media only), normalized to vehicle treatment (DMSO) at each compound concentration, and replicate values averaged. To standardize across the two datasets, the Area Under dose response Curve (AUC) was calculated and then normalized such that AUC=0 represents complete cell killing. AUC=1 represents no effect, and AUC>1 represents a treatment granting a growth advantage to the cells. Curves were created by connecting individual response points in a piecewise linear fashion, rather than using a sigmoid curve fit. Then, the AUC of this piecewise linear fit was normalized to the area under a null curve spanning the tested concentration range. The calculated AUC values were in high agreement with previous analyses of this dataset ($r^2=0.87$) while correcting for artifacts introduced by forced sigmoid curve fitting seen in other studies (Seashore-Ludlow et al., 2015) (FIG. 14A). No batch correction was performed in addition to AUC standardization. The correlation between AUC values present in both datasets was on par (n=24,923; Spearman rho=0.5) with previous studies (Hatzis et al., 2014; Pozdeyev et al., 2016). To standardize drug representation across datasets, the PubChem entry for each compound used in CTRP or GDSC was queried to obtain an isomeric SMILES notation based on the drug name or InChIKey provided in the dataset. Compounds with no matches in the initial search were manually annotated. To computationally represent chemical structure. RDKit (http://www.rdkit.org/) was used to calculate a Morgan fingerprint (radius=2), which decomposes each chemical structure into molecular fragments by iteratively obtaining distinct paths through each atom of the molecule. These fragments were hashed into a bit vector of length 2,048 to be used for model training. Genotypes of each cell line were formulated from non-synonymous coding mutations as previously annotated and used by the Cancer Cell Line Encyclopedia (http://portals.broadinstitute.org/ccle, 18q2 release) (Barretina et al., 2012). The dataset was filtered to represent only the top 15% most frequently mutated genes (n=3,008). Each cell-line genotype was represented as a bit vector across the 3,008 DrugCell genes indicating the mutational status of each gene in that cell line (0=wild type: 1=mutated).

Neural network configuration, training and evaluation. The DrugCell VNN (the genotype embedding branch; FIGS. 1A and 1B) was configured following the DCell protocol (Ma et al., 2018) with minor modifications. Each subsystem ss in DCell, and also in the hierarchy of subsystems in DrugCell (see above), is assigned a number k of neurons to represent its multidimensional state. This subsystem state, denoted by the output vector $O^{(s)}$ $O^{(s)}$, is defined as a function of the states of its c child subsystems and g directly annotated genes, concatenated in the input vector $I^{(s)}$ $I^{(s)}$.

$$O^{(s)} = f\left(W^{(s)}I^{(s)} + b^{(s)}\right)$$
$$W^{(s)}O^{(s)} = f\left(W^{(s)}I^{(s)} + b^{(s)}\right)$$

$W^{(s)}$ is a weight matrix of dimensions k×(k*c+g)k×(k*c+g) and $b^{(s)}$ $b^{(s)}$ is a weight vector of dimension kk. $W^{(s)}$ and $b^{(s)}$ provide the parameters to be learned for subsystem ss. The function $f$ $f$ is a non-linear transformation based on hyperbolic tangent and batch normalization. Training of parameters is performed using an objective (loss) function based on mean-squared error and an optimization procedure based on standard gradient descent and back-propagation. All parameters are initialized uniformly at random between −0.001 and 0.001.

In what follows, this disclosure focuses on aspects of DrugCell that significantly build on or depart from the original DCell model (Ma et al., 2018). First, in parallel to the subsystem hierarchy used to embed genotype, DrugCell implements a drug embedding branch configured as a conventional artificial neural network with three hidden layers, with the neurons of each layer fully connected to the next (these three layers have 100, 50, and 6 neurons respectively, see FIG. 1C). The input vector to this ANN is the 2,048-bit Morgan fingerprint of a drug (described above) and is fully-connected to the first hidden layer with 100 neurons. The final layer is a set of six neurons representing the drug embedding learned by DrugCell. These six neurons are concatenated with the six-neuron genotype embedding (see above) and fed to an additional hidden layer of six neurons, which feeds a final output layer of a single neuron representing the predicted drug response, $O^{(DC)}$ $O^{(DC)}$, measured as a continuous valued AUC (see FIG. 1A and Pharmacogenomics data processing section, above). Second, the number of neurons per subsystem k (VNN branch, see above) is selected by training and evaluation of a progression of neural network models with increasing values of this parameter (k=1,3,6,9,12 k=1,3,6, 9, 12; FIG. 14B). The DrugCell model used for all subsequent analysis is configured with k=6 k=6., as this value yielded the best Spearman rho between actual and predicted drug responses across all (cell-line, drug) pairs. The DrugCell model is implemented using the PyTorch library and trained using three GPU servers (two servers with Nvidia RTX 2080Ti with 4352 CUDA cores and 11 Gb GDDR6 RAM; one server with Tesla K80 with 4992 CUDA cores and 24 Gb GDDR5 RAM).

Model predictive performance was evaluated using a standard training/validation/test procedure. The 509,294 (cell line, drug) pairs in the data were divided into five groups of approximately equal size. Five separate models were created, in which each of these groups was held out as the test data, and the remaining four groups were pooled for training and validation. During the training phase of each model, 5,000 random (cell line, drug) pairs were further withheld for use as a validation set on which model predictive performance was used as an early terminating condition; all remaining samples were designated as training. Each model was trained through a maximum of 300 epochs;

performance on the validation data was evaluated after each epoch and training was terminated early in the event of decreasing model performance. The performance of each model was measured using Spearman rho between actual and predicted drug responses (AUC) in the test data and the final overall performance was reported (rho=0.80) as the average rho across the five models. Following evaluation of model performance (FIG. 2), a model trained using all 509,294 (cell line, drug) pairs was used to ensure maximal predictive power and interpretability (FIGS. 3 and 7).

Implementation of alternative models for comparison of predictive performance. DrugCell was compared to several alternative models trained using the same data as DrugCell: an Elastic net (FIG. 2B) and two fully connected neural network models (FIGS. 2C, 2D). A similar test procedure for 5-fold cross validation to that described above was used for evaluation of all these models. The elastic net model was implemented using the ElasticNetCV function in the scikit-learn library with cv=5. A black-box neural network model ("Matched" in FIG. 2C) was designed to have an identical hierarchical structure as DrugCell, but with the gene annotation inputs (gene-to-subsystem assignments) randomly shuffled. The predictive performance was reported as an average Spearman (rho) across 10 such random models. A second black-box model ("Tissue only" in FIG. 2D) was a fully connected neural network model, whose input was a 2,049-bit vector concatenating the 2,048-bit Morgan fingerprint representation of each drug and a single bit indicating the tissue of origin for each cell line. All elements in the input layer were fed to a stack of five hidden layers, of which each has 1,000, 500, 200, 100, 50 neurons respectively. The final hidden layer of 50 neurons was connected to a single neuron representing the predicted drug response output. DrugCell's predictive performance was further compared to that of five additional models, using the predictive performance reported in the corresponding publications rather than reimplementing those models directly (Ammad-ud-din et al., 2017; Cortés-Ciriano et al., 2016; Iorio et al., 2016; Zhang et al . . . 2015).

Ranking important subsystems in DrugCell. To quantitatively determine important subsystems for drug response prediction, the Relative Local Improvement in Predictive Power (RLIPP) score was adopted as described previously for DCell (Ma et al., 2018). Briefly, for each subsystem in DrugCell two different L2-norm penalized linear regression models of drug response local to that subsystem were constructed and compared. The first regression model predicts drug response using the neuron values that represent the state of the subsystem under the different genotypes. The second regression model predicts drug response using the neuron values that represent the states of the subsystem's children. Both models are optimized to predict drug response, but with consecutive layers of neurons located at and below the subsystem of interest in DrugCell. Performance is calculated as the Spearman correlation (rho) between the actual and predicted drug responses for each of the two alternative linear regression models (AUC). The RLIPP score is then defined as the ratio of Spearman rho of the first linear model to that of the second linear model. RLIPP>1 reflects that the state of the parent subsystem has more predictive power for drug response than the mere concatenation of the states of its children, indicating the importance of the parent subsystem in learning.

Comparing important DrugCell subsystems to predictive biomarkers reported by alternative models. Beyond a comparative assessment of predictive accuracy (see above), a comparison of the genes and subsystems nominated by DrugCell to genetic markers reported previously was performed. For this comparison, the focus was on predictive models published by the GDSC (elastic net and random forest) (Iorio et al., 2016) in a previous analysis of the same cell-line drug response data as examined (see Pharmacogenomics data processing above). The focus was on 60 drugs for which GDSC had published predictive gene mutations that were relatively frequent in tumors (top 15% of mutated genes in the integrated GDSC and CTRP dataset, see above). For each of these drugs, the genetic mutations identified as predictive biomarkers in the GDSC study were listed, along with the corresponding DrugCell subsystem containing that gene and its RLIPP score. Separately, the top three subsystems reported by DrugCell according to RLIPP score were examined. For every gene in one of these subsystems, it was determined the maximum weight connecting that gene to the neuron of that subsystem that is most relevant to the observed drug response (AUC); the top three genes by weight were reported. To select the most relevant neuron to drug response, first the principal component that has the strongest Spearman correlation with the observed drug response was identified. Next, the neuron with the highest loading (eigenvalue) to that principal component was determined as the most relevant neuron to that response.

Viability assays. Cell viability assays were conducted according to the manufacturer's specifications for CellTiter-Glo Luminescent Cell Viability Assay (Promega). Cells were seeded at 1,000 cells/well in a 384-well microtiter plate and treated after 24 hours. Drugs were diluted in the respective culture medium at the indicated concentrations. Cells were treated for 72h before the addition of CellTiter-Glo reagent and read on a Synergy HT Multi-Detection Microplate Reader (Biotek).

Combinatorial CRISPR-Cas9 gene knockouts and systematic evaluation. For gene knockout experiments, the CRISPR-Cas9 nuclease was stably integrated at the AAVS1 'safe harbor' locus in MFC7 cells. LentiCas9-Blast (Addgene plasmid #52962: http://n2t.net/addgene; 52962; RRID: Addgene_52962) and lentiCRISPR v2 (Addgene plasmid #52961; http://n2t.net/addgene: 52961: RRID: Addgene_52961) were gifts from Dr. Feng Zhang (Sanjana et al., 2014). MCF7-Cas9 cells were tested for *Mycoplasma* contamination, expanded, and frozen into multiple aliquots so that experiments could be performed at low passage numbers. Cells were grown in DMEM, 10% FBS, and hygromycin to select for Cas9 expression, which was confirmed by capillary western (Wes, Protein Simple). A custom library of double gRNA constructs (gene+non-targeting, gene+gene) was used which covers all single and pairwise combinations of 3 primary genes (MEK1, PARP1, TP53) versus 176 secondary genes. These secondary genes were designed to be broadly representative of major cancer-related processes including proliferative signaling, cell cycle progression, transcription regulation, and DNA repair with special attention to druggable targets and tumor suppressor genes. Double (primary, secondary) gRNA constructs were designed as described previously (Shen et al., 2017) with three distinct 20-bp gRNAs per target gene along with three non-targeting controls for a total of 3×3=9) constructs per gene or gene pair. The library was packaged into lentiviruses, and MCF7 cells were infected at an MOI of 0.3 to ensure each cell had zero or one double gRNA construct. Puromycin selection (2.5 µg/mL) was started two days after transduction and the concentration was reduced by half upon each splitting to a final concentration of 0.625 µg/ml., which was maintained for the remainder of the experiment. Following initial puromycin selection, cells were maintained in exponential growth by harvesting and removing a fraction of cells every two days. DNA was extracted from cells after 21 days of growth with a Blood and Cell Culture DNA Mini Kit (Qiagen) according to manufacturer protocols. To assess the relative frequencies of gRNAs before and after selection, integrated DNA encoding the gRNA sequence was PCR amplified and prepared for HiSeq4000 sequencing (Illumina) according to manufacturer protocols. Standard Illumina primers were used for library preparation, and sequencing was conducted to generate 100-bp reads in a paired-end fashion. After sequencing, data quality was assessed with FastQC. Fitness effects of gene knockouts were determined as previously described (Shen et al., 2017) and normalized to the median fitness for non-targeting guides. Experiments were performed in biological duplicate.

To systematically validate the identified mechanisms of sensitivity to trametinib, olaparib and nutlin-3, subsystems were first ranked by importance in DrugCell simulation of each compound (RLIPP analysis, see above). This ranking was filtered to retain the top five subsystems that contained sufficient (three or more) secondary genes in a CRISPR library. These subsystems were all among the top 25 overall subsystems (top 1%) identified for each drug. Then, an examination was conducted on the fitness effects resulting from pairwise knockout of the major target of each compound (MAP2K1, PARP1 and TP53) together with each CRISPR library gene present in a top subsystem (up to a maximum of five genes). These pairwise knockout effects were compared to the effects of pairwise knockout of the major target of each compound together with knockout of genes in five random subsystems selected from among those with low RLIPP scores<2.

Quantification and Statistical Analysis

Assessing the correspondence of learned subsystem embeddings to measured subsystem activities. To assess whether the subsystem states that DrugCell had learned are representative of experimentally measured activities of these subsystems, an expression-based analysis similar to that piloted by a previous DCell proof-of-concept (Ma et al 2018) was adapted. Reverse phase protein array (RPPA) data covering 899 cell lines was obtained from the Cancer Cell Line Encyclopedia, including the majority of cell lines for which genotypes and drug responses were used to train the DrugCell model. For each subsystem, a subsystem activity score was created similar to other methods that have been described for pathway-based gene expression analysis (Hwang, 2012; Yang et al., 2014). Here, the "RPPA activity" of each subsystem was calculated as the simple sum of signal intensities across all proteins and phosphorylation sites mapping to that subsystem. A random forest regression model was trained to predict this RPPA activity using the top 6 principal components of that subsystem's DrugCell embedding as features. The predictive performance of these individual subsystem models was compared to models trained to predict the RPPA activity of random sets of genes of matched sizes (FIG. 10A).

Differential expression analysis. Differential expression analysis was performed, which is commonly used to identify pathways regulating drug sensitivity (Kang et al., 2004; Nutt et al., 2000; Suzuki et al., 2014), to identify pathways mediating paclitaxel sensitivity. Raw RNAseq count data were obtained from CCLE (http://portals.broadinstitute.org/ccle) for the top 25 most paclitaxel sensitive and 25 most paclitaxel resistant cell lines. Raw counts were transformed to log 2 counts per million (log-CPM) and genes with low expression levels were removed (CPM<0.1) as previously described (Chen et al., 2016). Data were normalized using the trimmed mean of M-values (TMM) method (Robinson and Oshlack, 2010). Differential expression was determined by linear modeling using limma (Ritchie et al., 2015). Pathways enriched for differentially expressed genes were determined using DAVID (Huang et al., 2007). 125 genes were identified that were significantly differentially expressed (q<0.05) when contrasting the 25 most paclitaxel-sensitive cell lines with the 25 most paclitaxel-resistant cell lines (FIG. 12B). Pathways enriched for these genes included RNA splicing and cell division (FIG. 12C), consistent with previous studies (Bani et al., 2004; Liu et al., 2017; Moos and Fitzpatrick, 1998), as well as pathways responding to ionizing radiation and DNA replication.

Synergy determinations. Drug combination profiling data across a diverse cell line panel were obtained from Deep-Synergy (http://www.bioinf.jku.at/software/DeepSynergy/) (Preuer et al., 2018), which used the Loewe model of additivity (Loewe. 1953) to evaluate the interaction of 583 different drug combinations across 39 human cancer cell lines. These DeepSynergy data were used to systematically evaluate the ability of DrugCell to pair a primary drug $D_1$ with a synergistic second agent $D_2$ by targeting top subsystems mediating sensitivity to the primary drug (see text and FIG. 5A-J). Protein target information was collected for drugs from the Therapeutic Target Database (Wang et al., 2020), yielding targets for 283 drugs on which DrugCell had been trained in cell lines and 32 drugs considered by DeepSynergy. The 25 drugs in the intersection of these sets were used for systematic evaluation. For each drug in the set of 25 drugs $D_1=\{d_i|i=1 \ldots 25\}$ $D_1=\{d_i|i=1 \ldots 25\}$, a set of predicted synergistic target genes. $G_i$ $G_i$ were gathered, based on their membership in the top 10 subsystems by RLIPP score $$\left(s_i^1, s_i^2, \ldots, s_i^{10}\right)$$

such that $$G_i = U_{j=1}^{10} GOA\left(s_i^j\right),$$

where GOA(s) is a set of genes contained in a subsystem s according to the Gene Ontology Annotation. A set of secondary drugs, $$\left\{y_i^1, y_i^2, \ldots, y_i^m\right\}$$

were then collected, targeting any gene in $G_i$ $G_i$ and compiled a set of synergistic drug combinations, $$\{d_i\} \times D_2^i = \left\{\left(d_i, y_i^1\right), \left(d_i, y_i^2\right), \ldots, \left(d_i, y_i^m\right)\right\}$$

Across all 25 primary drugs in $D_1$, $D_1$, the set of synergistic secondary drugs, $$D_2 = U_{i=1}^{25} D_2^i$$

led to 75 predicted synergistic drug pairs with corresponding observed DeepSynergy scores. This process was repeated for the bottom 10 RLIPP subsystems to predict a set of non-synergistic secondary drugs, $$D'_2 = U_{i=1}^{25} D'^i_2$$

leading to 70 predicted non-synergistic drug pairs with corresponding observed DeepSynergy scores. Finally, the distribution of the synergy scores were compared for the predicted synergistic pairs, the predicted non-synergistic pairs, and the remaining 76 drug pairs in DeepSynergy (FIG. 5D).

Translation of continuous cell response (AUC) to binary cell response. In addition to Spearman correlation, Drug-Cell's predictive performance has been characterized by the ability to separate cells into binary sensitive versus resistant response classes (FIGS. 5H-5J). For this purpose, Drug-Cell's continuous predictions of drug response (AUC) were binarized as follows. Let $O_i$ (d) $O_i$ (d) represent the actual response of cell line ii exposed to drug dd, reflecting the area under dose response curve (AUC), and let $$O_i^{(DC)}(d)$$

represent the corresponding predictive output of DrugCell. We then seek a drug-specific threshold, $t_d$ $t_d$, that maximizes balanced accuracy over all cell lines was determined as follows:

$$t_d = \text{argmax}_x$$

$$\left(\text{mean}\left(\frac{\left|\left\{i \mid O_i^{(DC)}(d) \leq \text{ and } O_i(d) \leq x\right\}\right|}{\left|\{i \mid O_i(d) \leq x\}\right|}, \frac{\left|\left\{i \mid O_i^{(DC)}(d) > x \text{ and } O_i(d) > x\right\}\right|}{\left|\{i \mid O_i(d) > x\}\right|}\right)\right)$$

DrugCell's prediction is then translated to a binary drug response $$\left(B^{(DC)} B_i^{(DC)} \in \{0\text{:sensitive, } 1\text{:resistant}\}\right)$$

by use of $t_d$ $t_d$:

$$B_i^{(DC)} = \begin{cases} 1, & O_i^{(DC)}(d) > t_d \\ 0, & \text{otherwise} \end{cases}$$

Identification of Boolean logic combinations. Embodiments described herein may be used to develop an approximate Boolean logic representation of how two subsystems, Regulation of PI3K activity and Negative regulation of ERK1/ERK2 cascade (henceforth called subsystems s and t), mediate the prediction of etoposide response in DrugCell. To achieve this Boolean representation, the continuous DrugCell prediction of drug AUC for each cell-line sample $$ii\left(O_i^{(DC)} \geq 0 O_i^{(DC)} \geq 0\right)$$

was translated to a binary drug response ($B^{(DC)}B^{(DC)} \in \{0:$ etoposide sensitive, 1: etoposide resistant$\}$) by use of a threshold (see above). Here, a threshold of 0.82 was selected as it maximizes balanced accuracy when using DrugCell for binary classification of etoposide response over all samples:

$$C_{\vec{v}'}^{(j)} = \begin{cases} 1, & P\!\left(B^{(j)} = 1 \middle| \vec{v} = \vec{v}'\right) > P\!\left(B^{(j)} = 1\right) \\ 0, & \text{otherwise} \end{cases}$$

| | | Observed Etoposide Response (AUC > 0.82?) | | Balanced accuracy = Mean {(500/ |
|---|---|---|---|---|
| | | 0 | 1 | 724, (372/430)} = 0.78 |
| DrugCell Predicted Reponse ($B^{(DC)}$:$O^{(DC)} > 0.82$?) | 0 | 500 | 58 | Odds Ratio = (500/58)/(224/372) = 14.32 |
| | 1 | 224 | 372 | Odds Ratio = (500/58)/(224/372) = 14.32 |

In the above table, the same threshold was applied to both the predictions (rows) and the observations (columns). The multi-dimensional output vector of each subsystem $$\left(O_i^{(s)},\, O_i^{(t)}\right)\!\left(O_i^{(s)},\, O_i^{(t)}\right)$$

was translated to a binary state $$\left(B_i^{(s)}B_i^{(s)},\, B_i^{(t)}B_i^{(t)}\right) \in \left\{0{:}\text{unaltered. } 1{:}\text{altered}\right\}$$

using $O^{(s)}O^{(s)}$ or $O^{(t)}O^{(t)}$ as features to classify $B^{(DC)}B^{(DC)}$ using a kk-nearest neighbor (KNN) classifier with k=10 k=10 (Cover and Hart, 1967). The output of this classifier was taken as the binary value of the subsystem, $$B_i^{(s)}B_i^{(s)} \text{ or } B_i^{(t)}B_i^{(t)}.$$

For each subsystem, three exemplary genes with high importance to the subsystem output were selected, creating a vector of gene binary mutation states:

$$\vec{v}_i^{\,i} = \left(x_i^i,\, y_i^i,\, z_i^i\right),\, \text{where}$$

$$j \in \{s,\, t\} \text{ and } x,\, y,\, z \in \left\{0{:}\text{ unmutated}, 1{:}\text{ mutated}\right\}$$

These gene exemplars were defined as the three gene inputs most heavily weighted by DrugCell in connection to the neuron of ss or tt with the highest coefficient of variation over all ii. The above procedure thus yielded binarized values for six genes, two subsystems, and one drug response. For each possible combination of binary gene inputs, $\vec{v}'$ $\vec{v}'$, the (typically multiple) corresponding samples were examined to compute a consensus value f $$C_{\vec{v}'}^{(j)} C_{\vec{v}'}^{(j)}$$

or the states of the two subsystems and the DrugCell output ($j \in \{s, t, DC\}$ $j \in \{s, t, DC\}$) according to the following rule:

This process yielded a logical truth table which was expressed as a minimal set of Boolean logic gates (FIG. 4F) using the technique of Kamnaugh maps (Karnaugh, 1953).

PDX tumor analysis. For each PDX tumor, measured mutations in DrugCell genes were used as input to DrugCell to predict the response to 6 drugs belonging to compound classes that DrugCell had previously seen (abraxane, binimetinib, encorafenib, INC-280, BKM-120, and BYL-719) and had combination data available, which altogether had been treated in 13 pairwise combinations with secondary drugs from diverse target classes. Since AUC data does not exist for in vivo experiments, tumor size was used as a surrogate for AUC. RLIPP analysis was then performed to identify subsystems mediating response to each of the 6 drugs included in this analysis. For each of the 13 available drug combinations, a set of pathways were defined that would lead to the design of that particular combination. Over 100 different RLIPP values were scanned, and at each cutoff compared the identified pathways with the pathways defined for each of the tested combinations to see if it had been identified. A combination was considered to be 'effective' if it significantly improved progression free survival as compared to the tested single drugs (p<0.05, log-rank test). The observed PFS of each of these (primary, secondary) combinations was used to evaluate sensitivity and specificity as the number of top ranking DrugCell subsystems was progressively increased, yielding estimates of prediction sensitivity and specificity along a ROC curve for the combination panel.

Breast cancer patient analysis. Aggregated clinical trial data (Smyth et al., 2020) was obtained from Project GENIE (Genomics Evidence Neoplasia Information Exchange), an international genomics registry and data sharing platform established by the American Association for Cancer Research. This resource contained mutational profiling data and clinical outcomes for 457 metastatic breast cancer patients following multiple rounds of therapy. IF patients had not been treated with a targeted therapy (mTOR or CDK4/6 inhibitors, they were removed from the dataset. Such filtering produced a total of 221 estrogen receptor (ER) positive metastatic breast cancer patients who had undergone treatment with an mTOR inhibitor (everolimus), a CDK4/6 inhibitor (ribociclib), or both compounds in any round of therapy. Patient response to either mTOR or CDK4/6 inhibition were ingrttrf using a pre-trained DrugCell model and the mutational profiles of each patient. Patients were classified as DrugCell (+) if they were predicted sensitive (≤median predicted AUC across all patients) to either therapy (and had been treated with that particular therapy). Conversely, patients were classified as DrugCell (−) if they were predicted insensitive to both therapies. A log-rank test (p<0.05) was used to determine the significance of the associated treatment outcomes (overall survival).

Training and Inferencing/Predicting Using Machine-Learning Models

Various techniques may be used to train and inference/predict using machine-learning models, such as neural networks, according to at least one embodiment. In at least one embodiment, an untrained neural network is trained using a training dataset. Initial weight parameters of an untrained neural network may be set to an initial predetermined value, random numbers, etc. In at least one embodiment, a training framework is used to train a neural network using the training data set and update one or more weights of the neural network. The training framework may be any suitable training framework, such as a PyTorch framework, Tensor-Flow, Boost, Caffe, Microsoft Cognitive Toolkit/CNTK, MXNet, Chainer, Keras, Deeplearning4j, or other training framework. In at least one embodiment, training framework trains an untrained neural network and enables it to be trained using processing resources described herein to generate a trained neural network. In at least one embodiment, weights may be chosen randomly or by pre-training using a deep belief network. In at least one embodiment, training may be performed in either a supervised, partially supervised, or unsupervised manner.

In at least one embodiment, untrained neural network is trained using supervised learning, wherein training dataset includes an input (e.g., genotype information and drug structure) paired with a desired output for an input (e.g., predicted resistance or sensitivity to a compound), or where training dataset includes input having a known output and an output of neural network is manually graded. In at least one embodiment, untrained neural network is trained in a supervised manner and processes inputs from training dataset and compares resulting outputs against a set of expected or desired outputs. In at least one embodiment, errors are then propagated back through untrained neural network. In at least one embodiment, training framework adjusts weights that control the untrained neural network during the training process. In at least one embodiment, training framework includes tools to monitor how well untrained neural network is converging towards a model, such as trained neural network, suitable to generating correct answers, such as in result, based on input data such as a new dataset. In at least one embodiment, training framework trains untrained neural network repeatedly while adjust weights to refine an output of untrained neural network using a loss function and adjustment algorithm, such as stochastic gradient descent. In at least one embodiment, training framework trains untrained neural network until untrained neural network achieves a desired accuracy. In at least one embodiment, trained neural network can then be deployed to implement any number of machine learning operations.

In at least one embodiment, untrained neural network is trained using unsupervised learning, wherein untrained neural network attempts to train itself using unlabeled data. In at least one embodiment, unsupervised learning training dataset will include input data without any associated output data or "ground truth" data. In at least one embodiment, untrained neural network can learn groupings within training dataset and can determine how individual inputs are related to untrained dataset. In at least one embodiment, unsupervised training can be used to generate a self-organizing map in trained neural network capable of performing operations useful in reducing dimensionality of new dataset. In at least one embodiment, unsupervised training can also be used to perform anomaly detection, which allows identification of data points in new dataset that deviate from normal patterns of new dataset.

In at least one embodiment, semi-supervised learning may be used, which is a technique in which in training dataset includes a mix of labeled and unlabeled data. In at least one embodiment, training framework may be used to perform incremental learning, such as through transferred learning techniques. In at least one embodiment, incremental learning enables trained neural network to adapt to new dataset without forgetting knowledge instilled within trained neural network during initial training.

FIG. 15 is a block diagram illustrating an example of a computing device or computer system 1500 upon which any of one or more techniques (e.g., methods) may be performed, in accordance with one or more example embodiments of the present disclosure. Hardware described in connection with FIG. 15 may be utilized to implement various systems and environments described throughout this disclosure, for example, computer system 1500 may be used for training, prediction, inferencing, etc. using machine-learning models described throughout this disclosure.

For example, the computing system 1500 of FIG. 15 may include one or more processors 1502-1506. Processors 1502-1506 may include one or more internal levels of cache (not shown) and a bus controller (e.g., bus controller 1522) or bus interface (e.g., I/O interface 1520) unit to direct interaction with the processor bus 1512.

Processor bus 1512, also known as the host bus or the front side bus, may be used to couple the processors 1502-1506 with the system interface 1524. System interface 1524 may be connected to the processor bus 1512 to interface other components of the system 1500 with the processor bus 1512. For example, system interface 1524 may include a memory controller 1518 for interfacing a main memory 1516 with the processor bus 1512. The main memory 1516 typically includes one or more memory cards and a control circuit (not shown). System interface 1524 may also include an input/output (I/O) interface 1520 to interface one or more I/O bridges 1525 or I/O devices 1530 with the processor bus 1512. One or more I/O controllers and/or I/O devices may be connected with the I/O bus 1526, such as I/O controller 1528 and I/O device 1530, as illustrated.

I/O device 1530 may also include an input device (not shown), such as an alphanumeric input device, including alphanumeric and other keys for communicating information and/or command selections to the processors 1502-1506. Another type of user input device includes cursor control, such as a mouse, a trackball, or cursor direction keys for communicating direction information and command selections to the processors 1502-1506 and for controlling cursor movement on the display device.

System 1500 may include a dynamic storage device, referred to as main memory 1516, or a random access memory (RAM) or other computer-readable devices coupled to the processor bus 1512 for storing information and instructions to be executed by the processors 1502-1506. Main memory 1516 also may be used for storing temporary variables or other intermediate information during execution of instructions by the processors 1502-1506. System 1500 may include read-only memory (ROM) and/or other static storage device coupled to the processor bus 1512 for storing static information and instructions for the processors 1502-1506. The system outlined in FIG. 15 is but one possible example of a computer system that may employ or be configured in accordance with aspects of the present disclosure.

According to one embodiment, the above techniques may be performed by computer system 1500 in response to processor 1504 executing one or more sequences of one or more instructions contained in main memory 1516. These instructions may be read into main memory 1516 from another machine-readable medium, such as a storage device. Execution of the sequences of instructions contained in main memory 1516 may cause processors 1502-1506 to perform the process steps described herein. In alternative embodiments, circuitry may be used in place of or in combination with the software instructions. Thus, embodiments of the present disclosure may include both hardware and software components.

According to one embodiment, the processors 1502-1506 may include tensor processing units (TPUs) and/or other artificial intelligence accelerator application-specific integrated circuits (ASICs) that may allow for neural networking and other machine learning techniques. In at least one embodiment, machine-learning module 1532 refers to software and/or hardware that performs machine-learning techniques described herein, which may include training and/or inferencing stages. For example, machine-learning module 1532 may be trained to discriminate between different types and/or stages of metastatic cancer.

Various embodiments may be implemented fully or partially in software and/or firmware. This software and/or firmware may take the form of instructions contained in or on a non-transitory computer-readable storage medium. Those instructions may then be read and executed by one or more processors to enable the performance of the operations described herein. The instructions may be in any suitable form, such as, but not limited to, source code, compiled code, interpreted code, executable code, static code, dynamic code, and the like. Such a computer-readable medium may include any tangible non-transitory medium for storing information in a form readable by one or more computers, such as but not limited to read-only memory (ROM); random access memory (RAM); magnetic disk storage media; optical storage media; a flash memory, etc.

A machine-readable medium includes any mechanism for storing or transmitting information in a form (e.g., software, processing application) readable by a machine (e.g., a computer). Such media may take the form of, but is not limited to, non-volatile media and volatile media and may include removable data storage media, non-removable data storage media, and/or external storage devices made available via a wired or wireless network architecture with such computer program products, including one or more database management products, web server products, application server products, and/or other additional software components. Examples of removable data storage media include Compact Disc Read-Only Memory (CD-ROM), Digital Versatile Disc Read-Only Memory (DVD-ROM), magneto-optical disks, flash drives, and the like. Examples of non-removable data storage media include internal magnetic hard disks, solid state devices (SSD) s), and the like. The one or more memory devices (not shown) may include volatile memory (e.g., dynamic random access memory (DRAM), static random access memory (SRAM), etc.) and/or non-volatile memory (e.g., read-only memory (ROM), flash memory, etc.).

Computer program products containing mechanisms to effectuate the systems and methods in accordance with the presently described technology may reside in main memory

1516, which may be referred to as machine-readable media. It will be appreciated that machine-readable media may include any tangible non-transitory medium that is capable of storing or encoding instructions to perform any one or more of the operations of the present disclosure for execution by a machine or that is capable of storing or encoding data structures and/or modules utilized by or associated with such instructions. Machine-readable media may include a single medium or multiple media (e.g., a centralized or distributed database, and/or associated caches and servers) that store the one or more executable instructions or data structures.

REFERENCES

1. Ammad-ud-din, M., Khan, S. A., Wennerberg, K., and Aittokallio, T. (2017). Systematic identification of feature combinations for predicting drug response with Bayesian multi-view multi-task linear regression. Bioinformatics 33, i359-1368.
2. Ashburner, M., Ball, C. A., Blake, J. A., Botstein, D., Butler, H., Cherry, J. M., Davis, A. P., Dolinski, K., Dwight, S. S., Eppig, J. T., et al. (2000). Gene ontology: tool for the unification of biology. The Gene Ontology Consortium. Nat. Genet. 25, 25-29.
3. Bani, M. R., Nicoletti, M. I., Alkharouf, N. W., Ghilardi, C., Petersen, D., Erba, E., Sausville, E. A., Liu, E. T., and Giavazzi, R. (2004). Gene expression correlating with response to paclitaxel in ovarian carcinoma xenografts. Mol. Cancer Ther. 3, 111-121.
4. Baptista, D., Ferreira, P. G., and Rocha, M. (2020). Deep learning for drug response prediction in cancer. Brief. Bioinform.
5. Barretina, J., Caponigro, G., Stransky, N., Venkatesan, K., Margolin, A. A., Kim, S., Wilson, C. J., Lehár, J., Kryukov, G. V., Sonkin, D., et al. (2012). The Cancer Cell Line Encyclopedia enables predictive modelling of anticancer drug sensitivity. Nature 483, 603-307.
6. Breinig, M., Klein, F. A., Huber, W., and Boutros, M. (2015). A chemical-genetic interaction map of small molecules using high-throughput imaging in cancer cells. Mol. Syst. Biol. 11, 846.
7. Chen, Y., Lun, A. T. L., and Smyth, G. K. (2016). From reads to genes to pathways: differential expression analysis of RNA-Seq experiments using Rsubread and the edgeR quasi-likelihood pipeline. F1000Research 5, 1438.
8. Cheng, D. T., Mitchell, T. N., Zehir, A., Shah, R. H., Benayed, R., Syed, A., Chandramohan, R., Liu, Z. Y., Won, H. H., Scott, S. N., et al. (2015). Memorial Sloan Kettering-Integrated Mutation Profiling of Actionable Cancer Targets (MSK-IMPACT). J. Mol. Diagn. JMD 17, 251-264.
9. Ching, T., Himmelstein, D. S., Beaulieu-Jones, B. K., Kalinin, A. A., Do, B. T., Way, G. P., Ferrero, E., Agapow, P.-M., Zietz, M., Hoffman, M. M., et al. (2018). Opportunities and obstacles for deep learning in biology and medicine. J. R. Soc. Interface 15, 20170387.
10. Chiu, Y.-C., Chen, H.-I. H., Zhang, T., Zhang, S., Gorthi, A., Wang, L.-J., Huang, Y., and Chen, Y. (2019). Predicting drug response of tumors from integrated genomic profiles by deep neural networks. BMC Med. Genomics 12, 18.
11. Condorelli, R., Spring, L., O'Shaughnessy, J., Lacroix, L., Bailleux, C., Scott, V., Dubois, J., Nagy, R. J., Lanman, R. B., Iafrate, A. J., et al. (2018). Polyclonal RBI mutations and acquired resistance to CDK 4/6 inhibitors in patients with metastatic breast cancer. Ann. Oncol. Off. J. Eur. Soc. Med. Oncol. 29, 640-645.

12. Copley, S. D. (2012). Moonlighting is mainstream: Paradigm adjustment required. BioEssays 34, 578-588.

13. Cortés-Ciriano, I., van Westen, G. J. P., Bouvier, G., Nilges, M., Overington, J. P., Bender, A., and Malliavin, T. E. (2016). Improved large-scale prediction of growth inhibition patterns using the NCI60 cancer cell line panel. Bioinformatics 32, 85-95.

14. Costa, C., Wang, Y., Ly, A., Hosono, Y., Murchie, E., Walmsley, C. S., Huynh. T., Healy, C., Peterson, R., Yanase, S., et al. (2020). PTEN Loss Mediates Clinical Cross-Resistance to CDK4/6 and PI3Kα Inhibitors in Breast Cancer. Cancer Discov. 10, 72-85.

15. Costello. J. C., Heiser, L. M., Georgii, E., Gönen, M., Menden, M. P., Wang, N. J., Bansal, M., Ammad-uddin, M., Hintsanen, P., Khan, S. A., et al. (2014). A community effort to assess and improve drug sensitivity prediction algorithms. Nat. Biotechnol. 32, 1202-1212.

16. Cover, T., and Hart, P. (1967). Nearest neighbor pattern classification. IEEE Trans. Inf. Theory 13, 21-27.

17. Das, B., Yeger, H., Tsuchida, R., Torkin, R., Gee, M. F. W., Thorner, P. S., Shibuya. M., Malkin, D., and Baruchel, S. (2005). A Hypoxia-Driven Vascular Endothelial Growth Factor/Flt1 Autocrine Loop Interacts with Hypoxia-Inducible Factor-1α through Mitogen-Activated Protein Kinase/Extracellular Signal-Regulated Kinase 1/2 Pathway in Neuroblastoma. Cancer Res. 65, 7267-7275.

18. Dincer, A. B., Celik, S., Hiranuma, N., and Lee, S.-I. (2018). DeepProfile: Deep learning of cancer molecular profiles for precision medicine. BioRxiv 278739.

19. Eskiocak, B., McMillan, E. A., Mendiratta, S., Kollipara, R. K., Zhang. H., Humphries, C. G., Wang, C., Garcia-Rodriguez, J., Ding, M., Zaman, A., et al. (2017). Biomarker Accessible and Chemically Addressable Mechanistic Subtypes of BRAF Melanoma. Cancer Discov. 7, 832-851.

20. Esteva, A., Robicquet, A., Ramsundar, B., Kulcshov, V., DePristo, M., Chou, K., Cui, C., Corrado, G., Thrun, S., and Dean, J. (2019). A guide to deep learning in healthcare. Nat. Med. 25, 24.

21. Gao, H., Kom, J. M., Ferretti, S., Monahan, J. E., Wang, Y., Singh, M., Zhang, C., Schnell, C., Yang, G., Zhang, Y., et al. (2015). High-throughput screening using patient-derived tumor xenografts to predict clinical trial drug response. Nat. Med. 21, 1318-1325.

22. Garnett, M. J., Edelman, E. J., Heidorn, S. J., Greenman, C. D., Dastur, A., Lau, K. W., Greninger, P., Thompson, I. R., Luo, X., Soares, J., et al. (2012). Systematic identification of genomic markers of drug sensitivity in cancer cells. Nature 483, 570-575.

23. Hare, S. H., and Harvey, A. J. (2017). mTOR function and therapeutic targeting in breast cancer. Am. J. Cancer Res. 7, 383-404.

24. Harris, J. (2017). FDA Approves FoundationOne CDx, CMS Agrees to Cover. OncLive Novemb.

25. Hatzis, C., Bedard, P. L., Birkbak, N. J., Beck, A. H., Aerts, H. J. W. L., Stern, D. F., Shi, L., Clarke, R., Quackenbush, J., and Haibe-Kains, B. (2014). Enhancing Reproducibility in Cancer Drug Screening: How Do We Move Forward? Cancer Res. 74, 4016-4023.

26 Huang, D. W., Sherman, B. T., Tan, Q., Kir, J., Liu, D., Bryant, D., Guo, Y., Stephens, R., Baseler, M. W., Lane, H. C., et al. (2007). DAVID Bioinformatics Resources: expanded annotation database and novel algorithms to better extract biology from large gene lists. Nucleic Acids Res. 35, W169-W175.

27. Hwang, S. (2012). Comparison and evaluation of pathway-level aggregation methods of gene expression data. BMC Genomics 13, S26.

28. Iorio, F., Knijnenburg, T. A., Vis, D. J., Bignell, G. R., Menden, M. P., Schubert, M., Aben, N., Gonçalves, E., Barthorpe, S., Lightfoot, H., et al. (2016). A Landscape of Pharmacogenomic Interactions in Cancer. Cell 166, 740-754.

29. Kang, H. C., Kim, I.-J., Park, J.-H., Shin, Y., Ku, J.-L., Jung, M. S., Yoo, B. C., Kim, H. K., and Park, J.-G. (2004). Identification of Genes with Differential Expression in Acquired Drug-Resistant Gastric Cancer Cells Using High-Density Oligonucleotide Microarrays. Clin. Cancer Res. 10, 272-284.

30. Karnaugh, M. (1953). The map method for synthesis of combinational logic circuits. Trans. Am. Inst. Electr. Eng. Part Commun. Electron. 72, 593-599.

31 Katsanis, S. H., and Katsanis, N. (2013). Molecular genetic testing and the future of clinical genomics. Nat. Rev. Genet. 14, 415-426.

32. Kramer. M., Dutkowski, J., Yu, M., Bafna, V., and Ideker, T. (2014). Inferring gene ontologies from pairwise similarity data. Bioinformatics 30, 134-142.

33. Kuenzi, B. M., and Ideker, T. (2020). A census of pathway maps in cancer systems biology. Nat. Rev. Cancer 1-14.

34. Kuenzi, B. M., Rix, L. L. R., Kinose, F., Kroeger, J. L., Lancet, J. E., Padron, E., and Rix, U. (2019). Off-target based drug repurposing opportunities for tivantinib in acute myeloid leukemia. Sci. Rep. 9, 606.

35. Li, J., Zhao, W., Akbani, R., Liu, W., Ju, Z., Ling, S., Vellano, C. P., Roebuck, P., Yu, Q., Eterovic, A. K., et al. (2017). Characterization of Human Cancer Cell Lines by Reverse-phase Protein Arrays. Cancer Cell 37, 225-239.

36. Liu, T., Sun, H., Zhu, D., Dong, X., Liu, F., Liang, X., Chen, C., Shao, B., Wang, M., Wang, Y., et al. (2017). TRA2A Promoted Paclitaxel Resistance and Tumor Progression in Triple-Negative Breast Cancers via Regulating Alternative Splicing. Mol. Cancer Ther. 16, 1377-1388.

37. Loewe, S. (1953). The problem of synergism and antagonism of combined drugs. Arzneimittelforschung. 3, 285-290.

38. Ma, J., Yu, M. K., Fong, S., Ono, K., Sage, E., Demchak, B., Sharan, R., and Ideker, T. (2018). Using deep learning to model the hierarchical structure and function of a cell. Nat. Methods.

39. Ma, Y., Wang, L., Neitzel, L. R., Loganathan, S. N., Tang, N., Qin, L., Crispi, E. E., Guo, Y., Knapp, S., Beauchamp, R. D., et al. (2017). The MAPK Pathway Regulates Intrinsic Resistance to BET Inhibitors in Colorectal Cancer. Clin. Cancer Res. 23, 2027-2037.

40. Mathur, R., Chandna, S., N Kapoor, P., and S Dwarakanath, B. (2011). Peptidyl prolyl isomerase, Pinl is a potential target for enhancing the therapeutic efficacy of etoposide. Curr. Cancer Drug Targets 11, 380-392.

41. Menden, M. P., Iorio, F., Garnett, M., McDermott, U., Benes, C. H., Ballester, P. J., and Saez-Rodriguez, J. (2013). Machine Learning Prediction of Cancer Cell Sensitivity to Drugs Based on Genomic and Chemical Properties. PLOS ONE 8.

42. Michaloglou, C., Crafter, C., Siersbaek, R., Delpuech, O., Curwen, J. O., Carnevalli, L. S., Staniszewska, A. D., Polanska, U. M., Cheraghchi-Bashi, A., Lawson, M., et al. (2018). Combined Inhibition of mTOR and CDK4/6 Is Required for Optimal Blockade of E2F Function and Long-term Growth Inhibition in Estrogen Receptor-positive Breast Cancer. Mol. Cancer Ther. 17, 908-920.

43. Moos, P. J., and Fitzpatrick, F. A. (1998). Taxane-mediated gene induction is independent of microtubule stabilization: Induction of transcription regulators and enzymes that modulate inflammation and apoptosis. Proc. Natl. Acad. Sci. 95, 3896-3901.

44. Murdoch, W. J., Singh, C., Kumbier, K., Abbasi-Asl, R., and Yu, B. (2019). Definitions, methods, and applications in interpretable machine learning. Proc. Natl. Acad. Sci. 116, 22071-22080.

45. Nguyen, D., and Gocke, C. D. (2017). Managing the genomic revolution in cancer diagnostics. Virchows Arch. 477, 175-194.

46. Nutt, C. L., Noble, M., Chambers, A. F., and Cairncross, J. G. (2000). Differential Expression of Drug Resistance Genes and Chemosensitivity in Glial Cell Lineages Correlate with Differential Response of Oligodendrogliomas and Astrocytomas to Chemotherapy. Cancer Res. 60, 4812-4818.

47. Occhipinti, G., Romagnoli, E., Santoni, M., Cimadamore, A., Sorgentoni, G., Cecati, M., Giulietti, M., Battelli, N., Maccioni, A., Storti, N., et al. (2020). Sequential or Concomitant Inhibition of Cyclin-Dependent Kinase 4/6 Before mTOR Pathway in Hormone-Positive HER2 Negative Breast Cancer: Biological Insights and Clinical Implications. Front. Genet. 11.

48. Park, J. S., Burckhardt, C. J., Lazcano, R., Solis, L. M., Isogai, T., Li, L., Chen, C. S., Gao, B., Minna, J. D., Bachoo, R., et al. (2020). Mechanical regulation of glycolysis via cytoskeleton architecture. Nature 578, 621-626.

49. Pernas, S., Tolaney, S. M., Winer, E. P., and Goel, S. (2018). CDK4/6 inhibition in breast cancer: current practice and future directions. Ther. Adv. Med. Oncol. 10.

50. Potts, M. B., McMillan, E. A., Rosales, T. I., Kim, H. S., Ou, Y.-H., Toombs, J. E., Brekken, R. A., Minden, M. D., MacMillan, J. B., and White, M. A. (2015). Mode of action and pharmacogenomic biomarkers for exceptional responders to didemnin B. Nat. Chem. Biol. 11, 401-408.

51. Pozdeyev, N., Yoo, M., Mackie, R., Schweppe, R. E., Tan, A. C., and Haugen, B. R. (2016). Integrating heterogeneous drug sensitivity data from cancer pharmacogenomic studies. Oncotarget 7, 51619-51625.

52. Pratt, D., Chen, J., Welker, D., Rivas, R., Pillich, R., Rynkov, V., Ono, K., Miello, C., Hicks, L., Szalma. S., et al. (2015). NDEx, the Network Data Exchange. Cell Syst. 1, 302-305.

53. Preuer, K., Lewis, R. P. I., Hochreiter, S., Bender, A., Bulusu, K. C., Klambauer, G., and Wren, J. (2018). DeepSynergy: predicting anti-cancer drug synergy with Deep Learning. Bioinformatics 34, 1538-1546.

54. Rajkomar, A., Dean, J., and Kohane, I. (2019). Machine Learning in Medicine. N. Engl. J. Med. 380, 1347-1358.

55. Rampášek, L., Hidru, D., Smirnov, P., Haibe-Kains, B., and Goldenberg, A. (2019). Dr. VAE: improving drug response prediction via modeling of drug perturbation effects. Bioinformatics 35, 3743-3751.

56. Reinert, T., Saad, E. D., Barrios, C. H., and Bines, J. (2017). Clinical Implications of ESRI Mutations in Hormone Receptor-Positive Advanced Breast Cancer. Front. Oncol. 7.

57. Rentzsch, P., Witten, D., Cooper, G. M., Shendure, J., and Kircher, M. (2019). CADD: predicting the deleteriousness of variants throughout the human genome. Nucleic Acids Res. 47. D886-D894.

58. Ritchie, M. F., Phipson, B., Wu, D., Hu, Y., Law, C. W., Shi, W., and Smyth, G. K. (2015). limma powers differential expression analyses for RNA-sequencing and microarray studies. Nucleic Acids Res. 43, e47-e47.

59. Robinson, M. D., and Oshlack, A. (2010). A scaling normalization method for differential expression analysis of RNA-seq data. Genome Biol. 11, R25.

60. Rogers, D., and Hahn, M. (2010). Extended-Connectivity Fingerprints. J. Chem. Inf. Model. 50, 742-754.

61. Rudin, C. (2019). Stop explaining black box machine learning models for high stakes decisions and use interpretable models instead. Nat. Mach. Intell. 1, 206-215.

62. Sakellaropoulos, T., Vougas, K., Narang, S., Koinis, F., Kotsinas, A., Polyzos, A., Moss, T. J., Piha-Paul, S., Zhou, H., Kardala, E., et al. (2019). A Deep Learning Framework for Predicting Response to Therapy in Cancer. Cell Rep. 29, 3367-3373.e4.

63. Sanjana, N. F., Shalem, O., and Zhang, F. (2014). Improved vectors and genome-wide libraries for CRISPR screening. Nat. Methods 11, 783-784.

64. Seashore-Ludlow, B., Rees, M. G., Cheah, J. H., Cokol, M., Price, E. V., Coletti, M. E., Jones, V., Bodycombe, N. E., Soule, C. K., Gould, J., et al. (2015). Harnessing Connectivity in a Large-Scale Small-Molecule Sensitivity Dataset. Cancer Discov. 5, 1210-1223.

65. Shen, J. P., Zhao, D., Sasik, R., Luebeck, J., Birmingham, A., Bojorquez-Gomez, A., Licon, K., Klepper, K., Pekin, D., Beckett, A. N., et al. (2017). Combinatorial CRISPR-Cas9 screens for de novo mapping of genetic interactions. Nat. Methods 14, 573-576.

66. Shimamura, T., Chen, Z., Soucheray, M., Carretero, J., Kikuchi, E., Tchaicha, J. H., Gao, Y., Cheng, K. A., Cohoon, T. J., Qi, J., et al. (2013). Efficacy of BET bromodomain inhibition in Kras-mutant non-small cell lung cancer. Clin. Cancer Res. Off. J. Am. Assoc. Cancer Res. 19.

67. Smyth, L. M., Zhou, Q., Nguyen, B., Yu, C., Lepisto, E. M., Arnedos, M., Hasset, M. J., Lenoue-Newton, M. L., Blauvelt, N., Dogan, S., et al. (2020). Characteristics and Outcome of AKTIE17K-Mutant Breast Cancer Defined through AACR Project GENIE, a Clinicogenomic Registry. Cancer Discov. 10, 526-535.

68. Subramanian, A., Tamayo, P., Mootha, V. K., Mukherjee, S., Ebert, B. L., Gillette, M. A., Paulovich, A., Pomeroy, S. L., Golub, T. R., Lander, F. S., et al. (2005). Gene set enrichment analysis: a knowledge-based approach for interpreting genome-wide expression profiles. Proc. Natl. Acad. Sci. U.S.A. 102, 15545-15550.

69. Suzuki, S., Horinouchi, T., and Furusawa. C. (2014). Prediction of antibiotic resistance by gene expression profiles. Nat. Commun. 5, 1-12.

70. Topol, E. J. (2019). High-performance medicine: the convergence of human and artificial intelligence. Nat. Med. 25, 44-56.

71. Turner, R. M., Park, B. K., and Pirmohamed, M. (2015). Parsing interindividual drug variability: an emerging role for systems pharmacology. Wiley Interdiscip. Rev. Syst. Biol. Med. 7, 221-241.

72. Wainberg, M., Merico, D., Delong, A., and Frey, B. J. (2018). Deep learning in biomedicine. Nat. Biotechnol. 36, 829-838.

73. Wang, Y., Zhang, S., Li, F., Zhou, Y., Zhang, Y., Wang, Z., Zhang, R., Zhu, J., Ren, Y., Tan, Y., et al. (2020). Therapeutic target database 2020: enriched resource for facilitating research and early development of targeted therapeutics. Nucleic Acids Res. 48, D1031-D1041.

74. Wong, C. H., Siah, K. W., and Lo, A. W. (2019). Estimation of clinical trial success rates and related parameters. Biostatistics 20, 273-286.

75. Yang, J. H., Wright, S. N., Hamblin, M., McCloskey, D., Alcantar, M. A., Schrübbers, L., Lopatkin, A. J., Satish, S., Nili, A., Palsson, B. O., et al. (2019). A White-Box Machine Learning Approach for Revealing Antibiotic Mechanisms of Action. Cell 177, 1649-1661.e9.

76. Yang, L., Ainali, C., Tsoka, S., and Papageorgiou, L. G. (2014). Pathway activity inference for multiclass disease classification through a mathematical programming optimisation framework. BMC Bioinformatics 15, 390.

77. Yang. W., Soares, J., Greninger, P., Edelman, E. J., Lightfoot, H., Forbes, S., Bindal, N., Beare, D., Smith, J. A., Thompson, I. R., et al. (2013). Genomics of Drug Sensitivity in Cancer (GDSC): a resource for therapeutic biomarker discovery in cancer cells. Nucleic Acids Res. 47, D955-D961.

78. Yeh, P. J., Hegreness, M. J., Aiden, A. P., and Kishony, R. (2009). Drug interactions and the evolution of antibiotic resistance. Nat. Rev. Microbiol. 7, 460-466.

79 Yin, Y., Sun, M., Zhan, X., Wu, C., Geng, P., Sun, X., Wu, Y., Zhang, S., Qin, J., Zhuang, Z., et al. (2019). EGFR signaling confers resistance to BET inhibition in hepatocellular carcinoma through stabilizing oncogenic MYC. J. Exp. Clin. Cancer Res. 38, 83.

80. Yu, M. K., Ma, J., Fisher, J., Kreisberg, J. F., Raphael, B. J., and Ideker, T. (2018). Visible Machine Learning for Biomedicine. Cell 173, 1562-1565.

81. Zeng, X., Zhu, S., Liu, X., Zhou, Y., Nussinov, R., and Cheng, F. (2019). deepDR: a network-based deep learning approach to in silico drug repositioning. Bioinformatics 35, 5191-5198.

82. Zhang, N., Wang, H., Fang, Y., Wang, J., Zheng, X., and Liu, X. S. (2015). Predicting Anticancer Drug Responses Using a Dual-Layer Integrated Cell Line-Drug Network Model. PLOS Comput. Biol. 11, e1004498.

83. Zhavoronkov, A., Ivanenkov, Y. A., Aliper, A., Veselov, M. S., Aladinskiy, V. A., Aladinskaya, A. V., Terenticv. V. A., Polykovskiy, D. A., Kuznetsov, M. D., Asadulaev, A., et al. (2019). Deep learning enables rapid identification of potent DDR1 kinase inhibitors. Nat. Biotechnol. 37, 1038-1040.

What is claimed is:

1. A system for predicting one or more effects of administration of a compound to a living tissue of a subject, comprising:

one or more processors; and memory storing execution instructions that, as a result of execution by the one or more processors, cause the one or more processors to:

determine genotype information of the living tissue;

provide the genotype information to a first portion of one or more neural networks, wherein the first portion comprises a visible neural network (VNN), wherein the VNN further comprises:

a plurality of neurons are organized into a plurality of subsystems that corresponds to known or putative molecular subsystems; and a plurality of connections, wherein a connection between a first subsystem and a second subsystem of the VNN corresponds to a known or putative molecular pathway, wherein a weight of the connection is determined during training of the one or more neural networks and corresponds to how predictive the connection is to a drug response;

receive, from the VNN, a first embedding vector representing cell genotype information;

provide a molecular fingerprint of the compound to a second portion of the one or more neural networks, wherein the second portion comprises an artificial neural network (ANN) that determines canonical vector representations of compounds;

receive, from the ANN, a second embedding vector representing compound structure information of the compound; and provide the first embedding vector and the second embedding vector to a third portion of the one or more neural networks, wherein the third portion comprises one or more layers of neurons trained to predict a response of the compound based on the genotype information; and receive, from the third portion, a prediction of whether the subject will respond to the administration of the compound.

2. The system of claim 1, wherein Relative Local Improvement in Predictive Power metric (RLIPP) scoring is used to identify subsystems of the plurality of subsystems that are most predictive of a response to the compound.

3. The system of claim 1, wherein the third portion of the one or more neural networks comprises a single layer of neurons that are integrated to generate a predicted effect of a given genotype to the compound.

4. The system of claim 1, wherein the genotype information comprises mutation statuses of a plurality of genes.

5. The system of claim 1, wherein the predication predicts the effects of the compound on a genotypically defined cancer tissue.

6. The system of claim 1, wherein the instructions include further instructions that, as a result of execution by the one or more processors, further causes the one or more processors:

presenting a graphical interface comprising a visualization of the plurality of subsystems mediating the response.

7. The system of claim 6, wherein the visualization provides an indication one or more metabolic pathways.

8. The system of claim 1, wherein the compound comprise a chemotherapeutic, a targeted therapy, or a combination thereof.

9. The system of claim 1, wherein:

the VNN is organized into a plurality of layers;

a first layer of the plurality of layers that receives the genotype information represents genes; and one or more subsequent layers of the plurality of layers represent molecular subsystems of greater complexity and/or scale.

10. The system of claim 1, wherein the VNN comprises six layers.

11. The system of claim 1, wherein the ANN comprises a fully connected network.

12. The system of claim 1, wherein the third portion of the one or more neural networks comprises a single layer of neurons that integrates the first embedding and second embedding to generate the prediction of whether the subject will respond to the administration of the compound.

13. A method for predicting one or more effects of administration of a compound to a living tissue of a subject, comprising:

determining genotype information of the living tissue;

providing the genotype information to a first portion of one or more neural networks, wherein the first portion comprises a visible neural network (VNN), wherein the VNN further comprises:

a plurality of neurons are organized into a plurality of subsystems that corresponds to known or putative molecular subsystems; and a plurality of connections, wherein a connection between a first subsystem and a second subsystem of the VNN corresponds to a known or putative molecular pathway, wherein a weight of the connection is determined during training of the one or more neural networks and corresponds to how predictive the connection is to a drug response; receiving, from the VNN, a first embedding vector representing cell genotype information;

providing a molecular fingerprint of the compound to a second portion of the one or more neural networks, wherein the second portion comprises an artificial neural network (ANN) that determines canonical vector representations of compounds;

receiving, from the ANN, a second embedding vector representing compound structure information of the compound; and providing the first embedding vector and the second embedding vector to a third portion of the one or more neural networks, wherein the third portion comprises one or more layers of neurons trained to predict a response of the compound based on the genotype information; and receiving, from the third portion, a prediction of whether the subject will respond to the administration of the compound.

14. The method of claim 13, wherein Relative Local Improvement in Predictive Power metric (RLIPP) scoring is used to identify subsystems of the plurality of subsystems that are most predictive of a response to the compound.

15. The method of claim 13, wherein the third portion of the one or more neural networks comprises a single layer of neurons that are integrated to generate a predicted effect of a given genotype to the compound.

16. The method of claim 13, wherein the genotype information comprises mutation statuses of a plurality of genes.

17. The method of claim 13, wherein the predication predicts the effects of the compound on a genotypically defined cancer tissue.

18. The method of claim 13, further comprising:

presenting a graphical interface comprising a visualization of the plurality of subsystems mediating the response.

19. The method of claim 18, wherein the visualization provides an indication one or more metabolic pathways.

20. The method of claim 13, wherein the compound comprise a chemotherapeutic, a targeted therapy, or a combination thereof.

21. The method of claim 13, wherein:

the VNN is organized into a plurality of layers;

a first layer of the plurality of layers that receives the genotype information represents genes; and one or more subsequent layers of the plurality of layers represent molecular subsystems of greater complexity and/or scale.

22. The method of claim 13, wherein the VNN comprises six layers.

23. The method of claim 13, wherein the ANN comprises a fully connected network.

24. The method of claim 13, wherein the third portion of the one or more neural networks comprises a single layer of neurons that integrates the first embedding and second embedding to generate the prediction of whether the subject will respond to the administration of the compound.

25. A method for combinatorial drug design, comprising:

determining one or more subsystems mediating sensitivity of a living tissue to a first drug based at least in part on one or more neural networks comprising a visible neural network (VNN) that models the living tissue and an artificial neural network (ANN) that models the first drug;

wherein the VNN comprises:

a plurality of nodes are organized into a plurality of subsystems that corresponds to known or putative molecular subsystems; and a plurality of connections, wherein a connection between a first subsystem and a second subsystem of the VNN corresponds to a known or putative molecular pathway, wherein a weight of the connection is determined during training of the one or more neural networks and corresponds to how predictive the connection is to a drug response; wherein the ANN comprises a plurality of layers that are trained to determine structure information of the first drug;

determining a set of genes based on membership in at least a portion of the one or more subsystems;

determining a set of secondary drugs that target at least one of the set of target genes; and determining, based at least in part on the VNN and the ANN, at least one synergistic combination of the first drug and a second drug selected from the set of secondary drugs, wherein the at least one synergistic combination has greater predicted effectiveness than the first drug alone and the second drug alone.

26. A method of claim 25, wherein the at least one synergistic combination further comprises a third drug selected from the set of secondary drugs, and the at least one synergistic combination has greater predicted effectiveness than the third drug alone.

27. A method of claim 25, further comprising:

determining Relative Local Improvement in Predictive Power metric (RLIPP) scores for the plurality of subsystems;

ranking the plurality of subsystems based on the RLIPP scores; and selecting the one or more subsystems as highest-ranking subsystems based on the RLIPP scores.

28. A method of claim 25, wherein:

the first drug alone is determined to have a first effectiveness that is less than a threshold, indicating a resistance to the first drug alone; and the at least one synergistic combination is determined to have a second effectiveness that is greater than the threshold, indicating a sensitivity to the at least one synergistic combination.

29. The method of claim 25, wherein the first drug comprise a chemotherapeutic, a targeted therapy, or a combination thereof.

30. The method of claim 25, wherein:

the VNN is organized into a plurality of layers;

a first layer of the plurality of layers receives genotype information of the living tissue and represents genes; and one or more subsequent layers of the plurality of layers represent molecular subsystems of greater complexity and/or scale.

31. The method of claim 25, wherein the VNN comprises six layers.

32. The method of claim 25, wherein the ANN comprises a fully connected network.

33. A method, comprising:

training one or more neural networks to predict a response of a living tissue to a compound using one or more neural networks, wherein the one or more neural networks comprises a first portion, a second portion, and a third portion, further wherein:

the first portion of the one or more neural networks comprises a visible neural network (VNN) trained to determine a first embedding vector representing cell genotype information of the living tissue, wherein the VNN further comprises:

a plurality of nodes are organized into a plurality of subsystems that corresponds to known or putative molecular subsystems; and a plurality of connections, wherein a connection between a first subsystem and a second subsystem of the VNN corresponds to a known or putative molecular pathway;

the second portion comprises an artificial neural network (ANN) that is trained to determine a second embedding vector representing structure information of the compound from a molecular fingerprint of the compound; and the third portion comprises at least one layer of neurons that receive the first embedding vector and the second embedding vectors and generate the predicted response.

34. The method of claim 33, wherein the genotype information comprises mutation statuses of a plurality of genes.

35. The method of claim 33, wherein the training comprises:

determining a Boolean logic circuit comprising a plurality of gates that approximates how the mutational status of the plurality of genes affects the predicted response.

36. The method of claim 33, wherein the training comprises:

determining weights of the plurality of connections based on how predictive a respective connection of the plurality is to the predicted response.

37. The method of claim 33, wherein the compound comprise a chemotherapeutic, a targeted therapy, or a combination thereof.

38. The method of claim 33, wherein:

the VNN is organized into a plurality of layers;

a first layer of the plurality of layers that receives the genotype information represents genes; and one or more subsequent layers of the plurality of layers represent molecular subsystems of greater complexity and/or scale.

39. The method of claim 33, wherein the VNN comprises six layers.

40. The method of claim 33, wherein the ANN comprises a fully connected network.

\* \* \* \* \*